(12) United States Patent
Buck et al.

(10) Patent No.: US 11,439,799 B2
(45) Date of Patent: Sep. 13, 2022

(54) SPLIT DILATOR ASPIRATION SYSTEM

(71) Applicant: Imperative Care, Inc., Campbell, CA (US)

(72) Inventors: Michael Buck, Menlo Park, CA (US); Julia Fox, San Carlos, CA (US); James Jacobs, Danville, CA (US)

(73) Assignee: Imperative Care, Inc., Campbell, CA (US)

( * ) Notice: Subject to any disclaimer, the term of this patent is extended or adjusted under 35 U.S.C. 154(b) by 0 days.

(21) Appl. No.: 17/357,672

(22) Filed: Jun. 24, 2021

(65) Prior Publication Data

US 2021/0316121 A1 Oct. 14, 2021

Related U.S. Application Data

(63) Continuation-in-part of application No. 17/125,723, filed on Dec. 17, 2020, now Pat. No. 11,065,018.
(Continued)

(51) Int. Cl.
*A61M 29/00* (2006.01)
*A61M 25/01* (2006.01)
(Continued)

(52) U.S. Cl.
CPC ........ *A61M 29/00* (2013.01); *A61M 25/0028* (2013.01); *A61M 25/0136* (2013.01);
(Continued)

(58) Field of Classification Search
CPC .. A61M 29/00; A61M 25/0028; A61M 25/02; A61M 25/09; A61M 25/0136;
(Continued)

(56) References Cited

U.S. PATENT DOCUMENTS

| 3,605,750 A | 9/1971 | Sheridan et al. |
| 3,884,242 A | 5/1975 | Bazell et al. |
(Continued)

FOREIGN PATENT DOCUMENTS

| CN | 110916768 | 3/2020 |
| DE | 8900059 | 5/1989 |
(Continued)

OTHER PUBLICATIONS

Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.
(Continued)

*Primary Examiner* — Amber R Stiles
(74) *Attorney, Agent, or Firm* — Knobbe Martens Olson & Bear, LLP

(57) ABSTRACT

A split dilator aspiration system is disclosed. The system includes a catheter, having an elongate, flexible tubular body with a proximal end, a distal end, a side wall defining a central lumen, and a handle on the proximal end. A dilator is advanceable through the central lumen, the dilator having an elongate body, cannulated to receive a guidewire, and an axially extending split along at least a portion of the elongate body, configured to allow removal of a portion of the dilator laterally from the guidewire.

47 Claims, 31 Drawing Sheets

Related U.S. Application Data

(60) Provisional application No. 63/064,273, filed on Aug. 11, 2020, provisional application No. 63/044,511, filed on Jun. 26, 2020, provisional application No. 62/950,058, filed on Dec. 18, 2019.

(51) Int. Cl.
*A61M 25/00* (2006.01)
*A61M 25/02* (2006.01)
*A61M 25/09* (2006.01)

(52) U.S. Cl.
CPC ............ *A61M 25/02* (2013.01); *A61M 25/09* (2013.01); *A61M 2025/024* (2013.01); *A61M 2025/0293* (2013.01); *A61M 2025/09116* (2013.01)

(58) Field of Classification Search
CPC .... A61M 2025/0293; A61M 2025/024; A61M 2025/09116
See application file for complete search history.

(56) References Cited

U.S. PATENT DOCUMENTS

| | | |
|---|---|---|
| 3,890,976 A | 6/1975 | Bazell et al. |
| 3,965,901 A | 6/1976 | Penny et al. |
| 4,030,503 A | 6/1977 | Clark, III |
| 4,319,580 A | 3/1982 | Colley et al. |
| 4,611,594 A | 9/1986 | Grayhack et al. |
| 4,617,019 A | 10/1986 | Fecht et al. |
| 4,619,274 A | 10/1986 | Morrison |
| 4,628,168 A | 12/1986 | Nebergall et al. |
| 4,762,129 A | 8/1988 | Bonzel |
| 4,762,130 A | 8/1988 | Fogarty et al. |
| 4,767,399 A | 8/1988 | Bollish |
| 4,810,582 A | 3/1989 | Gould et al. |
| 4,844,064 A | 7/1989 | Thimsen et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,217,705 A | 6/1993 | Reno et al. |
| 5,226,909 A | 7/1993 | Evans et al. |
| 5,234,416 A | 8/1993 | Macaulay et al. |
| 5,243,997 A | 9/1993 | Uflacker et al. |
| 5,261,916 A | 11/1993 | Engelson et al. |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A | 5/1995 | Wilk et al. |
| 5,423,846 A | 6/1995 | Fischell |
| 5,439,445 A | 8/1995 | Kontos |
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,549,119 A | 8/1996 | Solar |
| 5,569,178 A | 10/1996 | Henley |
| 5,569,277 A | 10/1996 | Evans et al. |
| 5,591,187 A | 1/1997 | Dekel |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,702,373 A | 12/1997 | Samson |
| 5,766,191 A | 6/1998 | Trerotola |
| 5,776,141 A | 7/1998 | Klein et al. |
| 5,827,242 A | 10/1998 | Follmer et al. |
| 5,843,103 A | 12/1998 | Wulfman |
| 5,873,882 A | 2/1999 | Straub et al. |
| 5,876,414 A | 3/1999 | Straub |
| 5,885,209 A | 3/1999 | Green |
| 5,891,114 A | 4/1999 | Chien et al. |
| 5,895,398 A | 4/1999 | Wensel et al. |
| 5,899,892 A | 5/1999 | Mortier et al. |
| 5,916,192 A | 6/1999 | Nita et al. |
| 5,935,112 A | 8/1999 | Stevens |
| 5,938,645 A | 8/1999 | Gordon |
| 5,951,539 A | 9/1999 | Nita |
| 6,007,530 A | 12/1999 | Dornhofer et al. |
| 6,056,837 A | 5/2000 | Lieber et al. |
| 6,059,745 A | 5/2000 | Gelbfish |
| 6,090,118 A | 7/2000 | McGuckin, Jr. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 | 1/2001 | Bates et al. |
| 6,197,014 B1 | 3/2001 | Samson et al. |
| 6,206,852 B1 | 3/2001 | Lee |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,267,783 B1 | 7/2001 | Letendre et al. |
| 6,285,903 B1 | 9/2001 | Rosenthal et al. |
| 6,355,027 B1 | 3/2002 | Le et al. |
| 6,394,976 B1 | 5/2002 | Winston et al. |
| 6,451,036 B1 | 6/2002 | Heitzmann et al. |
| 6,451,005 B1 | 9/2002 | Saitou et al. |
| 6,458,139 B1 | 10/2002 | Palmer et al. |
| 6,468,219 B1 | 10/2002 | Njemanze |
| 6,482,217 B1 | 11/2002 | Pintor et al. |
| 6,511,492 B1 | 1/2003 | Rosenbluth et al. |
| 6,524,303 B1 | 2/2003 | Garibaldi et al. |
| 6,520,934 B1 | 3/2003 | Lee et al. |
| 6,533,751 B2 | 3/2003 | Cragg et al. |
| 6,554,820 B1 | 4/2003 | Wendlandt et al. |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,666,874 B2 | 12/2003 | Heitzmann |
| 6,669,670 B1 | 12/2003 | Muni et al. |
| 6,719,717 B1 | 4/2004 | Johnson et al. |
| 6,776,770 B1 | 8/2004 | Trerotola |
| 6,805,692 B2 | 10/2004 | Muni et al. |
| 6,824,550 B1 | 11/2004 | Pintor et al. |
| 6,977,068 B1 | 12/2005 | Nair et al. |
| 7,004,954 B1 | 2/2006 | Voss et al. |
| 7,008,434 B2 | 3/2006 | Kurz et al. |
| 7,029,482 B1 | 4/2006 | Vargas et al. |
| 7,037,267 B1 | 5/2006 | Lipson et al. |
| 7,104,979 B2 | 9/2006 | Jansen et al. |
| 7,112,298 B2 | 9/2006 | Kampa et al. |
| 7,172,620 B2 | 2/2007 | Gilson |
| 7,175,653 B2 | 2/2007 | Gaber |
| 7,207,980 B2 | 4/2007 | Christian et al. |
| 7,223,274 B2 | 5/2007 | Vargas et al. |
| 7,229,461 B2 | 6/2007 | Chin et al. |
| 7,232,452 B2 | 6/2007 | Adams et al. |
| 7,235,088 B2 | 6/2007 | Pintor et al. |
| 7,250,042 B2 | 7/2007 | Kataishi et al. |
| 7,306,585 B2 | 12/2007 | Ross |
| 7,309,334 B2 | 12/2007 | von Hoffmann |
| 7,335,216 B2 | 2/2008 | Bender et al. |
| 7,491,210 B2 | 2/2009 | Dubrul et al. |
| 7,507,229 B2 | 3/2009 | Hewitt et al. |
| 7,537,568 B2 | 5/2009 | Moehring |
| 7,558,622 B2 | 7/2009 | Tran |
| 7,601,138 B2 | 10/2009 | Goebel et al. |
| 7,678,100 B2 | 3/2010 | Chin et al. |
| 7,713,227 B2 | 5/2010 | Wholey et al. |
| 7,763,196 B2 | 7/2010 | Goebel et al. |
| 7,771,358 B2 | 8/2010 | Moehring et al. |

(56) References Cited

U.S. PATENT DOCUMENTS

| | | |
|---|---|---|
| 7,803,136 B2 | 9/2010 | Schatz |
| 7,837,692 B2 | 11/2010 | Mulholland et al. |
| 7,842,055 B2 | 11/2010 | Pintor et al. |
| 7,850,623 B2 | 12/2010 | Griffin et al. |
| 7,905,891 B2 | 3/2011 | Self |
| 7,931,659 B2 | 4/2011 | Bose et al. |
| 7,938,820 B2 | 5/2011 | Webster et al. |
| 7,947,012 B2 | 5/2011 | Spurchise et al. |
| 7,988,646 B2 | 8/2011 | Taber |
| 8,021,351 B2 | 9/2011 | Boldenow et al. |
| 8,048,032 B2 | 11/2011 | Root et al. |
| 8,057,497 B1 | 11/2011 | Raju et al. |
| 8,062,316 B2 | 11/2011 | Patel et al. |
| 8,070,694 B2 | 12/2011 | Galdonik et al. |
| 8,084,246 B2 | 12/2011 | Hoon et al. |
| 8,114,106 B2 | 2/2012 | Straub |
| 8,142,413 B2 | 3/2012 | Root et al. |
| 8,114,032 B2 | 4/2012 | Ferry et al. |
| 8,157,792 B2 | 4/2012 | Dolliver et al. |
| 8,211,023 B2 | 7/2012 | Swan et al. |
| 8,235,968 B2 | 8/2012 | Tremaglio |
| 8,246,641 B2 | 8/2012 | Osborne et al. |
| 8,292,850 B2 | 10/2012 | Root et al. |
| 8,298,591 B2 | 10/2012 | Srivastava et al. |
| 8,308,655 B2 | 11/2012 | Grigoryants |
| 8,361,095 B2 | 1/2013 | Osborne |
| 8,366,735 B2 | 2/2013 | Bose et al. |
| 8,382,739 B2 | 2/2013 | Walak et al. |
| 8,394,078 B2 | 3/2013 | Torrance et al. |
| 8,403,912 B2 | 3/2013 | McFerran et al. |
| 8,460,312 B2 | 6/2013 | Bose et al. |
| 8,485,969 B2 | 7/2013 | Grayzel et al. |
| 8,517,955 B2 | 8/2013 | Keast et al. |
| 8,535,293 B2 | 9/2013 | Faherty et al. |
| 8,568,432 B2 | 10/2013 | Straub |
| 8,608,754 B2 | 12/2013 | Wensel et al. |
| 8,609,426 B2 | 12/2013 | Silver |
| 8,663,259 B2 | 3/2014 | Levine et al. |
| 8,682,411 B2 | 3/2014 | Kassab et al. |
| 8,684,963 B2 | 4/2014 | Qiu et al. |
| 8,696,698 B2 | 4/2014 | Chomas et al. |
| 8,702,680 B2 | 4/2014 | Jimenez et al. |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,814,892 B2 | 8/2014 | Galdonik et al. |
| 8,864,792 B2 | 10/2014 | Eckhouse et al. |
| 8,876,854 B2 | 11/2014 | Christiansen et al. |
| 8,900,257 B2 | 12/2014 | Straub et al. |
| 8,932,320 B1 | 1/2015 | Janardhan et al. |
| RE45,380 E | 2/2015 | Root et al. |
| 8,968,383 B1 | 3/2015 | Johnson et al. |
| 8,974,411 B2 | 3/2015 | McKinnon |
| 8,992,506 B2 | 3/2015 | Gulachenski |
| 8,996,095 B2 | 3/2015 | Anderson et al. |
| 8,998,946 B2 | 4/2015 | Morero |
| 9,014,786 B2 | 4/2015 | Carmeli et al. |
| 9,017,309 B2 | 4/2015 | Tanikawa et al. |
| 9,023,070 B2 | 5/2015 | Levine et al. |
| 9,039,715 B2 | 5/2015 | Diamant et al. |
| 9,079,000 B2 | 7/2015 | Hanson et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,199,064 B2 | 12/2015 | Morero |
| 9,238,124 B2 | 1/2016 | Grayzel et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,345,856 B2 | 5/2016 | Witte |
| 9,351,993 B2 | 5/2016 | Cruise et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,421,328 B2 | 8/2016 | Brueckner et al. |
| 9,439,791 B2 | 9/2016 | Vong et al. |
| 9,440,018 B2 | 9/2016 | Levin et al. |
| 9,446,216 B2 | 9/2016 | Olesky et al. |
| 9,451,884 B2 | 9/2016 | Palovich et al. |
| 9,451,963 B2 | 9/2016 | Cruise et al. |
| 9,463,006 B2 | 10/2016 | Forde et al. |
| 9,480,813 B2 | 11/2016 | Fukuoka et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,597,212 B2 | 3/2017 | Thompson et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,707,380 B2 | 7/2017 | Qiu et al. |
| 9,717,500 B2 | 8/2017 | Tieu et al. |
| 9,724,103 B2 | 8/2017 | Cruise et al. |
| 9,724,491 B2 | 8/2017 | Solar et al. |
| 9,764,111 B2 | 9/2017 | Gulachenski |
| 9,770,251 B2 | 9/2017 | Bowman et al. |
| 9,775,730 B1 | 10/2017 | Waltzman |
| 9,789,242 B2 | 10/2017 | Criado et al. |
| 9,789,283 B2 | 10/2017 | Richter et al. |
| 9,801,643 B2 | 10/2017 | Hansen et al. |
| 9,803,043 B2 | 10/2017 | Cruise et al. |
| 9,808,610 B2 | 11/2017 | Li et al. |
| 9,820,761 B2 | 11/2017 | Garrison et al. |
| 9,827,047 B2 | 11/2017 | Fudaba et al. |
| 9,855,072 B2 | 1/2018 | Moberg et al. |
| 9,861,783 B2 | 1/2018 | Garrison et al. |
| 9,877,731 B2 | 1/2018 | Cruise et al. |
| 9,878,076 B2 | 1/2018 | Gülcher et al. |
| 9,883,885 B2 | 2/2018 | Hendrick et al. |
| 9,907,880 B2 | 3/2018 | Cruise et al. |
| 9,913,960 B2 | 3/2018 | Blanchard et al. |
| 9,987,028 B2 | 6/2018 | Lowinger et al. |
| 9,999,355 B2 | 6/2018 | Kirenko |
| 10,010,698 B2 | 7/2018 | Watanabe et al. |
| 10,028,854 B2 | 7/2018 | Tatalovich et al. |
| 10,039,906 B2 | 8/2018 | Kume et al. |
| 10,070,878 B2 | 9/2018 | Ma |

(56) References Cited

U.S. PATENT DOCUMENTS

| | | |
|---|---|---|
| 10,086,169 B2 | 10/2018 | Grayzel et al. |
| 10,105,154 B1 | 10/2018 | Green |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,207,077 B2 | 2/2019 | Griggin et al. |
| 10,213,582 B2 | 2/2019 | Garrison et al. |
| 10,226,277 B2 | 3/2019 | Smith et al. |
| 10,238,833 B2 | 3/2019 | Christian et al. |
| 10,258,452 B2 | 4/2019 | Eckhouse et al. |
| 10,265,086 B2 | 4/2019 | Vale |
| 10,271,864 B2 | 4/2019 | Greenhalgh et al. |
| 10,278,678 B2 | 5/2019 | Peliks |
| 10,278,816 B2 | 5/2019 | Miller |
| 10,327,790 B2 | 6/2019 | Garrison et al. |
| 10,335,186 B2 | 7/2019 | Rosenbluth et al. |
| 10,342,570 B2 | 7/2019 | Richter et al. |
| 10,383,691 B2 | 8/2019 | Hendrick et al. |
| 10,384,034 B2 | 8/2019 | Garrison et al. |
| 10,420,581 B2 | 9/2019 | Hehrlein |
| 10,441,745 B2 | 10/2019 | Yang et al. |
| 10,456,552 B2 | 10/2019 | Goyal |
| 10,471,233 B2 | 11/2019 | Garrison et al. |
| 10,524,814 B2 | 1/2020 | Chang et al. |
| 10,531,883 B1 | 1/2020 | Deville et al. |
| 10,537,706 B2 | 1/2020 | Kanemasa et al. |
| 10,569,049 B2 | 2/2020 | Garrison et al. |
| 10,610,668 B2 | 4/2020 | Burkholz et al. |
| 10,646,239 B2 | 5/2020 | Garrison et al. |
| 10,653,426 B2 | 5/2020 | Yang et al. |
| 10,653,434 B1 | 5/2020 | Yang et al. |
| 10,661,053 B2 | 5/2020 | Yang et al. |
| 10,668,192 B2 | 6/2020 | Raney et al. |
| 10,695,159 B2 | 6/2020 | Hauser |
| 10,716,880 B2 | 7/2020 | Culbert et al. |
| 10,716,915 B2 | 7/2020 | Ogle et al. |
| 10,722,251 B2 | 7/2020 | Garrison et al. |
| 10,722,253 B2 | 7/2020 | Deville et al. |
| 10,722,683 B2 | 7/2020 | Solar et al. |
| 10,743,893 B2 | 8/2020 | Garrison et al. |
| 10,786,270 B2 | 9/2020 | Yang et al. |
| 10,835,272 B2 | 11/2020 | Yang et al. |
| 10,835,711 B2 | 11/2020 | Yang et al. |
| 10,856,898 B2 | 12/2020 | Matsushita et al. |
| 10,888,280 B2 | 1/2021 | Newberry |
| 10,905,850 B2 | 2/2021 | Christian et al. |
| 11,020,030 B2 | 6/2021 | Tao et al. |
| 11,065,018 B2 | 7/2021 | Buck et al. |
| 11,076,876 B2 | 8/2021 | Vale |
| 11,197,683 B1 | 12/2021 | Teigen et al. |
| 11,207,096 B2 | 12/2021 | To et al. |
| 11,207,497 B1 | 12/2021 | Yee et al. |
| 2001/0031980 A1 | 10/2001 | Wensel et al. |
| 2001/0031981 A1 | 10/2001 | Evans et al. |
| 2001/0049486 A1 | 12/2001 | Evans et al. |
| 2002/0016565 A1 | 2/2002 | Zadno-Azizi et al. |
| 2002/0026145 A1 | 2/2002 | Bagaoisan et al. |
| 2002/0074276 A1 | 6/2002 | Nakashima |
| 2002/0091372 A1 | 7/2002 | Cragg et al. |
| 2002/0156459 A1 | 10/2002 | Ye et al. |
| 2002/0156460 A1 | 10/2002 | Ye et al. |
| 2002/0169467 A1 | 11/2002 | Heitzmann et al. |
| 2002/0177899 A1 | 11/2002 | Eum et al. |
| 2002/0188314 A1 | 12/2002 | Anderson et al. |
| 2003/0088266 A1 | 5/2003 | Bowlin |
| 2003/0135193 A1 | 7/2003 | Hilgers et al. |
| 2003/0135198 A1 | 7/2003 | Berhow et al. |
| 2003/0153874 A1 | 8/2003 | Tal |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0138693 A1 | 7/2004 | Eskuri et al. |
| 2004/0153049 A1 | 8/2004 | Hewitt et al. |
| 2004/0199201 A1 | 10/2004 | Kellett et al. |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0055047 A1 | 3/2005 | Greenhalgh |
| 2005/0059957 A1 | 3/2005 | Campbell et al. |
| 2005/0103332 A1 | 5/2005 | Gingles et al. |
| 2005/0137680 A1 | 6/2005 | Ortiz et al. |
| 2005/0182386 A1 | 8/2005 | Aggerholm |
| 2006/0030835 A1 | 2/2006 | Sherman et al. |
| 2006/0064036 A1 | 3/2006 | Osborne et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0217664 A1* | 9/2006 | Hattier ............... A61M 29/00 604/164.1 |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2008/0064984 A1 | 3/2008 | Pflueger et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234715 A1 | 9/2008 | Pesce |
| 2008/0262350 A1 | 10/2008 | Unger |
| 2008/0300544 A1 | 12/2008 | Palm et al. |
| 2008/0312639 A1 | 12/2008 | Weber |
| 2009/0030400 A1 | 1/2009 | Bose et al. |
| 2009/0043330 A1 | 2/2009 | To |
| 2009/0182370 A1 | 7/2009 | Volobuyev et al. |
| 2009/0187143 A1 | 7/2009 | Vreeman |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264865 A1 | 10/2009 | Kawai |
| 2009/0270888 A1 | 10/2009 | Patel et al. |
| 2009/0275974 A1 | 11/2009 | Marchand et al. |
| 2009/0312699 A1 | 12/2009 | Pudelko |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0125253 A1 | 5/2010 | Olson et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009875 A1 | 1/2011 | Grandfield et al. |
| 2011/0034986 A1 | 2/2011 | Chou |
| 2011/0054504 A1 | 3/2011 | Porter |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0152998 A1 | 6/2011 | Berez et al. |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0238041 A1 | 9/2011 | Lim et al. |
| 2011/0295217 A1 | 12/2011 | Tanaka et al. |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0143237 A1 | 6/2012 | Cam et al. |
| 2012/0150147 A1 | 6/2012 | Leynov et al. |
| 2012/0290067 A1 | 11/2012 | Cam et al. |

(56) References Cited

U.S. PATENT DOCUMENTS

| | | |
|---|---|---|
| 2012/0330196 A1 | 12/2012 | Nita |
| 2013/0006225 A1 | 1/2013 | Cucin |
| 2013/0018318 A1 | 1/2013 | Ravichandran et al. |
| 2013/0018359 A1 | 1/2013 | Coyle |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0116701 A1 | 5/2013 | Wang et al. |
| 2013/0131641 A1 | 5/2013 | Jimenez et al. |
| 2013/0131710 A1 | 5/2013 | Carmeli et al. |
| 2013/0158578 A1 | 6/2013 | Ghodke et al. |
| 2014/0025043 A1 | 1/2014 | Wang et al. |
| 2014/0074144 A1 | 3/2014 | Shrivastava et al. |
| 2014/0114287 A1 | 4/2014 | Beasley et al. |
| 2014/0121746 A1 | 5/2014 | Kusleika et al. |
| 2014/0155932 A1 | 6/2014 | Bose et al. |
| 2014/0155980 A1 | 6/2014 | Turjman et al. |
| 2014/0163367 A1 | 6/2014 | Eskuri |
| 2014/0228808 A1 | 8/2014 | Webster et al. |
| 2014/0243882 A1 | 8/2014 | Ma |
| 2014/0249508 A1 | 9/2014 | Wang et al. |
| 2014/0271718 A1 | 9/2014 | Alvarez |
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276167 A1 | 9/2014 | Dasgupta et al. |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0309533 A1 | 10/2014 | Yamashita et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2015/0005704 A1 | 1/2015 | Heisei et al. |
| 2015/0046148 A1 | 2/2015 | Oh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0157772 A1 | 6/2015 | Li et al. |
| 2015/0173782 A1 | 6/2015 | Garrison et al. |
| 2015/0174363 A1 | 6/2015 | Sutermeister et al. |
| 2015/0257659 A1 | 9/2015 | Broers et al. |
| 2015/0290390 A1 | 10/2015 | Ring et al. |
| 2015/0335288 A1 | 11/2015 | Toth et al. |
| 2015/0335857 A1 | 11/2015 | Ishikawa |
| 2015/0359547 A1 | 12/2015 | Vale et al. |
| 2015/0366518 A1 | 12/2015 | Sampson |
| 2016/0000443 A1 | 1/2016 | Lilburn et al. |
| 2016/0008572 A1 | 1/2016 | Di Capriov |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney et al. |
| 2016/0206216 A1 | 7/2016 | Kirenko |
| 2016/0206322 A1 | 7/2016 | Fitz et al. |
| 2016/0213396 A1 | 7/2016 | Dowell et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0354532 A1 | 12/2016 | Olesky et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0043124 A1 | 2/2017 | Vreeman |
| 2017/0056061 A1 | 3/2017 | Ogle et al. |
| 2017/0071624 A1 | 3/2017 | McGuckin et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1 | 6/2017 | Kleshinski et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0246014 A1 | 8/2017 | Rapaport et al. |
| 2017/0252057 A1* | 9/2017 | Bonnette .......... A61B 17/32037 |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0303949 A1 | 10/2017 | Jacobi et al. |
| 2017/0340867 A1* | 11/2017 | Accisano, III ........ A61M 29/00 |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |

(56) References Cited

U.S. PATENT DOCUMENTS

| | | |
|---|---|---|
| 2018/0036155 A1 | 2/2018 | Tieu et al. |
| 2018/0042623 A1 | 2/2018 | Batiste |
| 2018/0055364 A1 | 3/2018 | Pierro |
| 2018/0055516 A1 | 3/2018 | Bagaoisan et al. |
| 2018/0104390 A1 | 4/2018 | Kilcran |
| 2018/0200478 A1 | 7/2018 | Lorenzo et al. |
| 2018/0207395 A1 | 7/2018 | Bulman et al. |
| 2018/0207399 A1 | 7/2018 | Chou et al. |
| 2018/0228502 A1 | 8/2018 | Shaffer et al. |
| 2018/0242962 A1 | 8/2018 | Walen et al. |
| 2018/0242980 A1 | 8/2018 | Lubock et al. |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2018/0263642 A1 | 9/2018 | Nita |
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2018/0338770 A1 | 11/2018 | Mogi et al. |
| 2018/0353194 A1 | 12/2018 | Shaffer et al. |
| 2019/0022363 A1 | 1/2019 | Grayzel et al. |
| 2019/0029825 A1 | 1/2019 | Fitterer et al. |
| 2019/0070387 A1 | 3/2019 | Goyal |
| 2019/0105477 A1 | 4/2019 | Heilman et al. |
| 2019/0105478 A1 | 4/2019 | Malek et al. |
| 2019/0108540 A1 | 4/2019 | Look et al. |
| 2019/0167124 A1 | 6/2019 | Verkruijsse et al. |
| 2019/0175030 A1 | 6/2019 | Verkruijsse et al. |
| 2019/0200871 A1 | 7/2019 | De Haan |
| 2019/0239910 A1 | 8/2019 | Brade et al. |
| 2019/0275290 A1 | 9/2019 | Yamashita et al. |
| 2019/0290884 A1 | 9/2019 | Kanemasa et al. |
| 2019/0329003 A1 | 10/2019 | Watanabe |
| 2019/0336142 A1 | 11/2019 | Torrie |
| 2019/0336727 A1 | 11/2019 | Yang et al. |
| 2019/0351182 A1 | 11/2019 | Chou et al. |
| 2019/0366041 A1 | 12/2019 | Yang et al. |
| 2020/0001046 A1 | 1/2020 | Yang et al. |
| 2020/0008820 A1 | 1/2020 | Aboytes et al. |
| 2020/0009301 A1 | 1/2020 | Yee |
| 2020/0009350 A1 | 1/2020 | Goyal |
| 2020/0022712 A1 | 1/2020 | Deville et al. |
| 2020/0023160 A1 | 1/2020 | Chou et al. |
| 2020/0046368 A1 | 2/2020 | Merritt et al. |
| 2020/0046937 A1 | 2/2020 | Nakagawa et al. |
| 2020/0170521 A1 | 6/2020 | Gupta et al. |
| 2020/0171276 A1 | 6/2020 | Onozuka |
| 2020/0171277 A1 | 6/2020 | Garrison et al. |
| 2020/0188630 A1 | 6/2020 | Fujita et al. |
| 2020/0025845 A1 | 7/2020 | Yang et al. |
| 2020/0205845 A1 | 7/2020 | Yang et al. |
| 2020/0276411 A1 | 9/2020 | Ogle et al. |
| 2020/0289136 A1 | 9/2020 | Chou |
| 2020/0297362 A1 | 9/2020 | Deville et al. |
| 2020/0297972 A1 | 9/2020 | Yee et al. |
| 2020/0306501 A1 | 10/2020 | Yee et al. |
| 2020/0323535 A1 | 10/2020 | Yang et al. |
| 2020/0337716 A1 | 10/2020 | Garrison et al. |
| 2020/0345979 A1 | 11/2020 | Loh et al. |
| 2021/0001141 A1 | 1/2021 | Pfiffner |
| 2021/0045758 A1 | 2/2021 | Garrison et al. |
| 2021/0052296 A1 | 2/2021 | Garrison |
| 2021/0068852 A1 | 3/2021 | Spence |
| 2021/0093336 A1 | 4/2021 | Roue |
| 2021/0106238 A1 | 4/2021 | Strasser |
| 2021/0106792 A1 | 4/2021 | Rafiee |
| 2021/0128182 A1 | 5/2021 | Teigen et al. |
| 2021/0146094 A1 | 5/2021 | Christian et al. |
| 2021/0153744 A1 | 5/2021 | Pierro |
| 2021/0186537 A1 | 6/2021 | Buck et al. |
| 2021/0186542 A1 | 6/2021 | Buck et al. |
| 2021/0187244 A1 | 6/2021 | Buck et al. |
| 2021/0315596 A1 | 10/2021 | Buck et al. |
| 2021/0315597 A1 | 10/2021 | Buck et al. |
| 2021/0315598 A1 | 10/2021 | Buck et al. |
| 2021/0316127 A1 | 10/2021 | Buck et al. |
| 2021/0361909 A1 | 11/2021 | Cottone et al. |
| 2021/0378527 A1 | 12/2021 | Strasser et al. |
| 2021/0378696 A1 | 12/2021 | Yang et al. |
| 2022/0047849 A1 | 2/2022 | Yee et al. |

FOREIGN PATENT DOCUMENTS

| | | |
|---|---|---|
| DE | 10 2010 053111 | 6/2012 |
| DE | 10 2012 112732 | 6/2014 |
| EP | 0 330 843 | 12/1993 |
| EP | 0 582 533 | 2/1994 |
| EP | 0 309 471 | 8/1996 |
| EP | 1 349 486 | 3/2008 |
| EP | 2 069 528 | 3/2013 |
| EP | 2937 108 | 10/2015 |
| EP | 2 928 360 | 1/2017 |
| EP | 2 211 732 | 5/2018 |
| EP | 3 539 486 | 9/2019 |
| EP | 3 698 740 | 8/2020 |
| GB | 2077132 | 12/1981 |
| JP | 2002-535049 | 10/2002 |
| JP | 2003-527925 | 9/2003 |
| JP | 2006-102222 | 4/2006 |
| JP | 2006-521881 | 9/2006 |
| JP | 2008-502378 | 1/2008 |
| JP | 2013-504388 | 2/2013 |
| JP | 2014-515670 | 7/2014 |
| JP | 2015-504327 | 2/2015 |
| WO | WO 95/009659 | 4/1995 |
| WO | WO 2000/000100 | 1/2000 |
| WO | WO 2009/054968 | 4/2009 |
| WO | WO 2009/132218 | 10/2009 |
| WO | WO 2010/126786 | 11/2010 |
| WO | WO 2014/151209 | 9/2014 |
| WO | WO 2014/203336 | 12/2014 |
| WO | WO 2017/025775 | 2/2017 |
| WO | WO 2018/121363 | 7/2018 |
| WO | WO 2019/178165 | 9/2019 |
| WO | WO 2019/222518 | 11/2019 |
| WO | WO 2019/246583 | 12/2019 |
| WO | WO 2020/145928 | 7/2020 |
| WO | WO 2021/016213 | 1/2021 |
| WO | WO 2021/064955 | 4/2021 |
| WO | WO 2021/090821 | 5/2021 |
| WO | WO 2021/105658 | 6/2021 |
| WO | WO 2021/242734 | 12/2021 |

OTHER PUBLICATIONS

GUIDEZILLA Guide Extension Catheter, Boston Scientific 510k Submission, Feb. 20, 2017.

International Search Report and Written Opinion dated May 7, 2021 in application No. PCT/US20/65349.

Invitation to Pay Additional Fees for International Application No. PCT/US20/65349 dated Feb. 24, 2021.

Merit Medical Systems Acquired Distal Access's SPINR Platform, Jul. 15, 2015, Digital Access, LLC; Merit Medical Systems, 5 pages.

Simon et al., *Exploring the efficacy of cyclic vs. static aspiration in a cerebral thrombectomy model: an initial proof of concept study*, J. NeuroIntervent Surg 2014, 6 pp. 677-683.

Simon et al., *Hydrodynamic comparison of the Penumbra system and commonly available syringes in forced—suction thrombectomy*, J. NeuroIntervent Surg 2014, 6, pp. 205-211.

Spiotta et al., Evolution of thrombectomy approaches and devices for acute stroke: a technical review, J. NeuroIntervent Surg 2015, 7, pp. 2-7.

U.S. Appl. No. 15/443,874 (U.S. Pat. No. 10,835,711), filed Feb. 27, 2017 (Nov. 17, 2020), Telescoping Neurovascular Catheter With Enlargeable Distal Opening.

U.S. Appl. No. 15/443,877 (U.S. Pat. No. 10,183,146), filed Feb. 27, 2017 (Jan. 22, 2019), Method of Making an Enhanced Flexibility Neurovascular Catheter.

Korpelainen et al., 1995, Asymmetrical skin temperature in ischemic stroke, Stroke, 26(9):1543-1547.

(56) References Cited

OTHER PUBLICATIONS

U.S. Appl. No. 15/862,488 (U.S. Pat. No. 10,653,426), filed Jan. 4, 2018 (May 19, 2020), Thromboresistant Coatings for Aneurysm Treatment Devices.
U.S. Appl. No. 15/442,393 (U.S. Pat. No. 10,183,145), filed Feb. 24, 2017 (Jan. 22, 2019), Enhanced Flexibility Neurovascular Catheter.
U.S. Appl. No. 15/443,874 (U.S. Pat. No. 10,835,711), filed Feb. 27, 2017 (Nov. 17, 2020), Telescoping Neurovascular Catheter With Enlargeable.
U.S. Appl. No. 15/443,841 (U.S. Pat. No. 10,661,053), filed Feb. 27, 2017 (May 26, 2020), Method of Pulsatile Neurovascular Aspiration With Telescoping Catheter.
U.S. Appl. No. 15/443,838 (U.S. Pat. No. 10,179,224), filed Feb. 27, 2017 (Jan. 15, 2019), Enhanced Flexibility Neurovascular Catheter With Tensile Support.
U.S. Appl. No. 15/443,877 (U.S. Pat. No. 10,183,146), filed Feb. 27, 2017 (Jan. 22, 2019), Method of Making an Enhanced Flexibility Neurovascular.
U.S. Appl. No. 15/443,948 (U.S. Pat. No. 10,441,745), filed Feb. 27, 2017 (Oct. 15, 2019), Neurovascular Catheter With Enlargeable Distal End.
U.S. Appl. No. 16/542,657 (U.S. Pat. No. 11,147,949), filed Aug. 16, 2019 (Oct. 19, 2021), Method of Making an Enhanced Flexibility Neurovascular Catheter.
U.S. Appl. No. 15/444,038 (U.S. Pat. No. 10,183,147), filed Feb. 27, 2017 (Jan. 22, 2019), Neurovascular Catheter Extension Segment.
U.S. Appl. No. 16/398,626 (U.S. Pat. No. 10,835,272), filed Apr. 30, 2019 (Nov. 17, 2020), Devices and Methods for Removing Obstructive Material From an Intravascular Site.
U.S. Appl. No. 16/400,263 (U.S. Pat. No. 11,123,090), filed May 1, 2019 (Sep. 21, 2021), Neurovascular Catheter Having Atraumatic Angled Tip.
U.S. Appl. No. 16/683,718 (U.S. Pat. No. 10,653,434), filed Nov. 14, 2019 (May 19, 2020), Devices and Methods for Removing Obstructive Material From an Intravascular Site.
U.S. Appl. No. 16/704,330 (U.S. Pat. No. 10,786,270), filed Dec. 5, 2019 (Sep. 29, 2020), Neurovascular Aspiration Catheter With Elliptical Aspiration Port.
U.S. Appl. No. 17/070,832 (U.S. Pat. No. 11,134,859), filed Oct. 14, 2020 (Oct. 5, 2021), Systems and Methods for Multivariate Stroke Detection.
U.S. Appl. No. 17/125,723 (U.S. Pat. No. 11,065,018), filed Dec. 17, 2020 (Jul. 20, 2021), Methods and Systems for Advancing a Catheter to a Target Site.
U.S. Appl. No. 17/357,672, filed Jun. 24, 2021, Split Dilator Aspiration System.
U.S. Appl. No. 17/343,004 (U.S. Pat. No. 11,207,497), filed Jun. 9, 2021 (Dec. 28, 2021), Catheter With Enhanced Tensile Strength.
U.S. Appl. No. 15/862,488, filed Jan. 4, 2018, Thromboresistant Coatings for Aneurysm Treatment Devices.
U.S. Appl. No. 16/863,723, filed Apr. 30, 2020, Thromboresistant Coatings for Aneurysm Treatment Devices.
U.S. Appl. No. 17/574,907, filed Jan. 13, 2022, Thromboresistant Coatings for Aneurysm Treatment Devices.
U.S. Appl. No. 15/442,393, filed Feb. 24, 2017, Enhanced Flexibility Neurovascular Catheter.
U.S. Appl. No. 15/443,874, filed Feb. 27, 2017, Telescoping Neurovascular Catheter With Enlargeable Distal Opening.
U.S. Appl. No. 15/443,841, filed Feb. 27, 2017, Method of Pulsatile Neurovascular Aspiration With Telescoping Catheter.
U.S. Appl. No. 15/443,838, filed Feb. 27, 2017, Enhanced Flexibility Neurovascular Catheter With Tensile Support.
U.S. Appl. No. 15/443,877, filed Feb. 27, 2017, Method of Making an Enhanced Flexibility Neurovascular Catheter.
U.S. Appl. No. 15/443,948, filed Feb. 27, 2017, Neurovascular Catheter With Enlargeable Distal End.
U.S. Appl. No. 16/542,657, filed Aug. 16, 2019, Method of Making an Enhanced Flexibility Neurovascular Catheter.
U.S. Appl. No. 17/502,389, filed Oct. 15, 2021, Neurovascular Catheter With Enlargeable Distal End.
U.S. Appl. No. 15/444,038, filed Feb. 27, 2017, Neurovascular Catheter Extension Segment.
U.S. Appl. No. 16/833,585, filed Mar. 28, 2020, Enhanced Flexibility Neurovascular Catheter.
U.S. Appl. No. 16/503,899, filed Jul. 5, 2019, Sealed Neurovascular Extendable Catheter.
U.S. Appl. No. 16/802,317, filed Feb. 26, 2020, Catheter With Seamless Flexibility Transitions.
U.S. Appl. No. 16/503,886, filed Jul. 5, 2019, Vacuum Transfer Tool for Extendable Catheter.
U.S. Appl. No. 16/398,626, filed Apr. 30, 2019, Devices and Methods for Removing Obstructive Material From an Intravascular Site.
U.S. Appl. No. 16/400,263, filed May 1, 2019, Neurovascular Catheter Having Atraumatic Angled Tip.
U.S. Appl. No. 16/570,084, filed Sep. 13, 2019, Enhanced Flexibility Neurovascular Catheter With Tensile Support.
U.S. Appl. No. 16/683,718, filed Nov. 14, 2019, Devices and Methods for Removing Obstructive Material From an Intravascular Site.
U.S. Appl. No. 16/704,330, filed Dec. 5, 2019, Neurovascular Aspiration Catheter With Elliptical Aspiration Port.
U.S. Appl. No. 17/410,162, filed Aug. 24, 2021, Neurovascular Catheter Having Angled Tip.
U.S. Appl. No. 16/589,563, filed Oct. 1, 2019, Devices and Methods for Removing Obstructive Material From an Intravascular Site.
U.S. Appl. No. 17/036,258, filed Sep. 29, 2020, Embolic Retrieval Catheter.
U.S. Appl. No. 17/070,832, filed Oct. 14, 2020, Systems and Methods for Multivariate Stroke Detection.
U.S. Appl. No. 17/407,852, filed Aug. 20, 2021, Systems and Methods for Multivariate Stroke Detection.
U.S. Appl. No. 16/728,469, filed Dec. 27, 2019, Neurovascular Access With Dynamic Assistance.
U.S. Appl. No. 17/125,723, filed Dec. 17, 2020, Methods and Systems for Advancing a Catheter to a Target Site.
U.S. Appl. No. 17/125,217, filed Dec. 17, 2020, Methods and Systems for Treating a Pulmonary Embolism.
U.S. Appl. No. 17/125,743, filed Dec. 17, 2020, Systems for Accessing a Central Pulmonary Artery.
U.S. Appl. No. 17/125,742, filed Dec. 17, 2020, Methods and Systems for Accessing and Retrieving Thrombo-Emboli.
U.S. Appl. No. 17/357,490, filed Jun. 24, 2021, Catheter System for Treating Thromboemb Olic Disease.
U.S. Appl. No. 17/357,558, filed Jun. 24, 2021, Aspiration System With Accelerated Response.
U.S. Appl. No. 17/357,643, filed Jun. 24, 2021, Hemostasis Valve.
U.S. Appl. No. 17/357,715, filed Jun. 24, 2021, Methods of Placing Large Bore Aspiration Catheters.
U.S. Appl. No. 17/475,202, filed Sep. 14, 2021, Enhanced Flexibility Neurovascular Catheter.
U.S. Appl. No. 17/343,004, filed Jun. 9, 2021, Catheter With Enhanced Tensile Strength.
U.S. Appl. No. 17/398,244, filed Aug. 10, 2021, Catheter With a Preset Curve.
U.S. Appl. No. 29/811,884, filed Oct. 18, 2021, Inline Fluid Filter.
U.S. Appl. No. 17/527,393, filed Nov. 16, 2021, Catheter Drive System for Supra-Aortic Access.
U.S. Appl. No. 17/527,379, filed Nov. 16, 2021, Rob Otically Driven Interventional Device.
U.S. Appl. No. 17/527,460, filed Nov. 16, 2021, Sterile Packaging Assembly for Robotic Interventional Device.
U.S. Appl. No. 17/527,452, filed Nov. 16, 2021, Method of Robotically Performing a Neurovascular Procedure.
U.S. Appl. No. 17/527,456, filed Nov. 16, 2021, Multi Catheter Method of Performing a Robotic Neurovascular Procedure.
Bernava et al., Sep. 23, 2019, Direct trhomboaspiration efficacy for mechanical thrombectomy is related to the angle of interaction between the catheter and the clot, J. NeuroIntervent Surg., 0:1-6, doi:10.1136/neurintsurg-2019-015113.

* cited by examiner

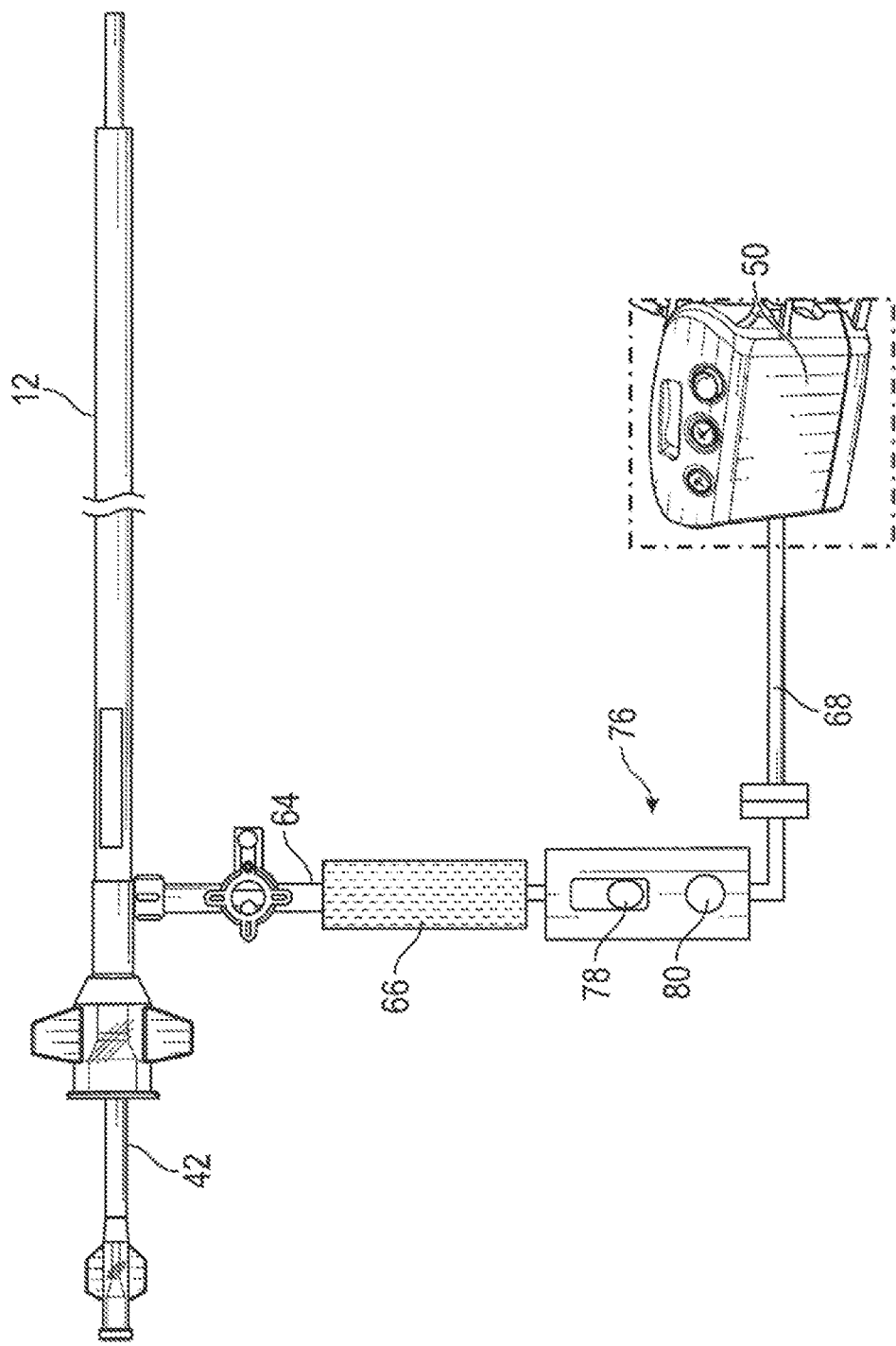

SPLIT DILATOR ASPIRATION SYSTEM

CROSS-REFERENCE TO RELATED APPLICATIONS

This application claims the priority benefit under 35 U.S.C. § 119(e) of U.S. Provisional Patent Application No. 63/044,511, filed Jun. 26, 2020, the entirety of which is hereby incorporated by reference herein. This application is a continuation-in-part of U.S. patent application Ser. No. 17/125,723, filed Dec. 17, 2020, which claims the priority benefit under 35 U.S.C. § 119(e) of U.S. Provisional Patent Application No. 62/950,058, filed Dec. 18, 2019 and U.S. Provisional Patent Application No. 63/064,273, filed Aug. 11, 2020, the entireties of which are hereby incorporated by reference herein.

BACKGROUND OF THE INVENTION

Thrombotic restrictions and occlusions within a patient's blood vessels are a significant medical problem and often require intervention to remove these restrictions and blockages to restore health to patients. While applicable to a wide range of vascular applications in both the arterial and venous systems, including a variety of small vessels, the following background illuminates the problems primarily through the example of patients suffering with Pulmonary Embolisms.

Venous thromboembolic disease (VTE) is a worldwide crisis. There are over 10 million cases of deep vein thrombosis (DVT) and pulmonary embolism (PE) diagnosed globally per year, with 1 million cases occurring in the United States and over 700,000 in France, Italy, Germany, Spain, Sweden, and the United Kingdom combined each year. There are approximately 60,000 to 100,000 deaths from PE in the United States each year. DVT and PE are part of the same continuum of disease, with over 95% of emboli originating in the lower extremities. When PE occurs, the severity depends on the embolic burden and its effect on the right ventricle as well as underlying cardiopulmonary comorbidities. Death can result from the acute increase in pulmonary artery (PA) pressure with increased right ventricular (RV) afterload and dysfunction.

Patients with high-risk pulmonary embolism (PE) were treated primarily with thrombolytic therapy delivered systemically or more locally through Catheter Directed Thrombolytics. These approaches result in multiple catheterization lab visits, lengthy hospital stays and often lead to bleeding complications. Newer approaches to PE treatment include single session thrombectomy treatments without the use of thrombolytics. These thrombectomy treatments include delivering a catheter into the PA to remove the thrombus through aspiration, and secondary tools may also macerate or disrupt the thrombus prior to aspiration. While thrombectomy results in fewer bleeding complications and reduced hospital stays compared to thrombolytics, there is much to be improved upon given the challenges of the procedure itself, including the ability to capture a broad spectrum of thrombus types and reduce the total volume of blood loss during the procedure.

The thrombectomy catheter is introduced through an introducer puncture in a large diameter vein. A flexible guide wire is passed through the introducer into the vein and the introducer is removed. The flexible guidewire provides a rail for a flexible guide catheter to be advanced through the right atrium into the right ventricle and into the pulmonary artery. The flexible guidewire is removed and replaced with a stiff guidewire. The large diameter thrombectomy catheter with support dilator is then advanced over the stiff guidewire to the pulmonary artery and the dilator is removed. If the large diameter thrombectomy catheter is not successful in accessing or aspirating thrombus in a more distal portion of the vessel, a smaller diameter catheter may be inserted through the large diameter catheter.

In addition, peripheral arterial occlusive (PAO) disease occurs in more than 4% of individuals over age 40 and markedly increases in incidence after the age of 70. Acute PAO is usually due to thrombosis of the peripheral vasculature and is associated with a significant risk of limb loss. In order to preserve the limb, therapy for acute PAO centers on the rapid restoration of arterial patency and blood flow such as through mechanical thrombectomy in procedures similar to those described above.

Clot aspiration using certain commercial vacuum-assisted thrombectomy systems may sometimes need to be terminated due to the risk of excessive blood loss by the patient, especially when using large aspiration catheters. During aspiration thrombectomy, when the catheter tip falls out of contact with the thrombus or other occlusive material, the tip is exposed to healthy blood and full flow of blood through the catheter ensues. Under such conditions, the total volume of blood loss is excessive, and in some cases, may result in premature termination of the procedure. For example, during a procedure when the catheter enters healthy blood and full aspiration flow ensues, the blood loss rate can be on the order of 30-40 cc per second with a 24 French size catheter. With a maximum tolerable blood loss on the order of about 500 mL, the catheter cannot run in unrestricted mode for more than approximately 10 to 15 seconds. The aggregate blood loss may reach an unacceptable level before sufficient clot is removed.

SUMMARY OF THE INVENTION

There is provided in accordance with one aspect of the present invention a first vacuum aspiration system, such as for aspirating a target material such as an obstruction from the vascular system. The system comprises a housing, a fluid flow path extending through the housing, and a chamber for capturing and storing removed material. A first catheter is in fluid communication with the flow path, and a connector is configured to place a source of aspiration (vacuum) in communication with the flow path. A flow regulator is configured to regulate fluid flow through the flow path. One or two or more operator actuated controls are configured to toggle the flow regulator in response to the operator's initiation, between a default, low flow mode, and a momentary, operator initiated high flow mode. The same control or a separate control may be provided to toggle aspiration between an off mode and an on mode.

The system further comprises a side wall containing the flow path, and an optically transparent window in the side wall. At least a portion of the side wall may be in the form of an optically transparent tube.

The flow regulator may comprise a variable sized constriction in the flow path. The flow regulator may comprise a flexible flow path side wall or tube and an actuator configured to compress the flexible tube. Alternatively, the flow regulator may comprise an adjustable aperture such as an iris or a valve, or a valve that toggles the flow path between a low flow (e.g. low diameter) path and a high flow (e.g. high diameter) path. Alternatively, the flow regulator may comprise tubing having a length and inside diameter selected to achieve a desired flow regulation.

The housing may further comprise a port, in communication with the first catheter, to guide a second, smaller catheter through the housing and into and through the first catheter. A hemostasis valve may be carried by the housing, in communication with the port.

The system may further comprise a reservoir for receiving thrombus and blood retrieved through the first catheter. The reservoir includes a filter for separating clot from blood, and a window to allow visual observation of the clot that has accumulated on the outside surface or inside surface of the filter. In one implementation, the filter comprises a tubular membrane spaced radially inwardly from an outer transparent tubular wall, to define an annular clot receiving chamber therebetween. Fluid flow during aspiration may be in the direction from the clot receiving chamber radially inwardly through the membrane. At least a portion of the reservoir may be releasably carried by the housing.

The housing may additionally be provided with an infusion port, for providing communication with an infusion lumen extending axially through the first catheter to an effluent port at the distal end of the catheter. The infusion lumen may be used to infuse a volume of an active medium such as a thrombolytic drug, or introduction of contrast agent to enable fluoroscopic visualization of the vasculature. Alternatively, the infusion lumen may be used to infuse a volume of saline, to facilitate flushing the catheter and/or dilute the contrast agent, and/or to dilute the aspirated blood thereby minimizing the total blood loss as a result of the procedure. The lumen can also be utilized to measure blood pressure at the distal end of the catheter.

The system may additionally be provided with a reinfusion circuit for directing filtered blood from the reservoir through a reinfusion pathway through the housing and into communication with a reinfusion port. The reinfusion port is configured to communicate with a reinfusion lumen extending axially through a separate reinfusion catheter which may be positioned within a reinfusion site in the patient, or with a reinfusion lumen on the access catheter which terminates at an infusion exit port. The exit port may be an end port, or a side port on the first catheter, spaced apart proximally from the distal end of the catheter.

During blood aspiration in the absence of thrombus, the second, low flow mode may aspirate fluid at a rate of no more than about 20 cc/second, generally no more than about 10 cc/second, and typically within the range of from about 1-5 cc/second. The third, high flow mode aspirates fluid at a rate of at least about 10 cc/second, generally at least about 15 cc/second and in one execution of the invention approximately 20 cc/second. Generally, the high flow mode aspiration rate will be no more than about 40 cc/second in an unobstructed aspiration. The low flow rate is typically within the range of from about 10% to about 75%, in some implementations between about 20% and 30% of the high flow mode aspiration rate.

A second vacuum aspiration system may be provided, via a Y connector in the tubing (not a separate second pump and cannister) for cooperation with the first vacuum aspiration system as may be desired depending upon the clinical situation. The second vacuum aspiration system may have all of the features and options described in connection with the first vacuum aspiration system except that the outside diameter of the second catheter on the second vacuum aspiration system is smaller than the inside diameter of the flow path through the first catheter, and the length of the second catheter is longer than the length of the first catheter.

If a clot is unable to be reached or aspirated by the first vacuum aspiration system, the second catheter may be distally advanced through the first catheter and distally beyond the distal end of the first catheter, enabling an additional opportunity to retrieve the clot.

In one implementation of the invention, the first catheter may be 24 French and having a length within the range of from about 80 cm to about 110 cm. The complementary second catheter may be 16 French with a length within the range of from about 110 cm and about 130 cm. Typically, the second catheter will have a length that is at least about 10 cm and in some implementations at least about 20 cm longer than the length of the first catheter.

In accordance with another aspect of the present invention, there is provided a vacuum aspiration catheter and control system. The system comprises a housing; a fluid flow path extending through the housing; a first catheter in fluid communication with the flow path and a connector configured to place a source of aspiration in communication with the flow path; and a flow regulator, configured to regulate fluid flow through the flow path. At least a first operator actuated control is provided, configured to toggle the flow regulator between a default, low flow mode, and a momentary, operator initiated high flow override mode. The system may additionally comprise a second operator actuated on-off control which toggles between an off mode and the low flow mode. The first and second controls may be carried by the housing.

A secondary catheter port may be provided on the housing, in communication with the first connector to guide a secondary catheter through the housing and into and through the first, large diameter catheter. A hemostasis valve may be carried by the housing, in communication with the secondary catheter port.

The flow path is defined within a tubular side wall having an inside diameter, and any clinically material changes in the inside diameter in the direction from the first catheter to the clot collection chamber are an increase. At least a portion of the side wall may be optically transparent, to provide a viewing window of the contents of the flow path. In one implementation, the window is located between the flow control regulator and the first catheter, such as between the housing and the first catheter, or incorporated into the housing or first catheter.

The system may be placed in combination with a reservoir for receiving thrombus and blood retrieved through the first catheter as has been discussed. A filter may be disposed in the reservoir, and material trapped by the filter is viewable through a viewing window in a sidewall defining the reservoir. The sidewall may be releasably connected to the housing allowing removal of the reservoir and filter from the housing.

The housing may be integrated into a proximal hub of the first catheter. The housing may be provided with additional controls, depending upon the desired functionality. For example, one or two or more pull wires may extend axially through the catheter for the purposes of steering the distal end of the catheter. The proximal ends of the pull wires may be connected to a steering control, such as a lever, slider switch or rotary control. The pull wires extend distally through the catheter to a steering zone. A single pull wire implementation permits lateral deflection in a single direction within a single plane. A two wire implementation may allow lateral deflection in opposite directions within the single plane, or deflection in two different planes without rotating the catheter or housing.

In accordance with another aspect of the present invention, there is provided a method of removing a vascular obstruction. The method comprises the steps of transvascularly advancing a distal end of an aspiration catheter into proximity with an obstruction, and activating a low flow, detection mode of aspiration through the catheter. If in the detection mode the actual flow rate drops to substantially below the expected flow rate, indicating the detection of a clot, the method may additionally comprise the step of manipulating a momentary control to activate a high flow, bolus aspiration mode of operation to more aggressively draw obstructive material into the distal end of the catheter. Activating a momentary control step may enlarge a restriction in a flow path between the thrombus container and a source of vacuum. The operator may thereafter deactivate (e.g., release) the override control, and the system will default to the second, low flow mode. Alternatively, a spike in negative pressure may be achieved at the distal end of the catheter using a dual vacuum chamber system, described in greater detail below.

Blood and thrombus aspirated during the procedure may be directed into a collection chamber and/or through a filter to separate clot from blood. Filtered blood may be directed back into the patient.

Proximal retraction of the thrombus through the first catheter may be facilitated with the use of a second catheter advanced through the first catheter.

The method may comprise advancing the distal end of the first or second catheter into proximity with a pulmonary embolism, into proximity with a deep vein thrombosis, or into proximity with a peripheral arterial or venous occlusion.

In accordance with another aspect of the invention, there is provided a flow control for large bore thrombo-emboli aspiration systems. The control comprises a housing, defining a central cavity, and having a patient port, a manifold port and a filter port. A movable gate is provided within the housing, having a flow path and configured to selectively place the patient port in communication with the filter port, the patient port in communication with the manifold port. The same flow control or separate control may also optionally place the manifold port in communication with the filter port.

The movable gate may comprise a cylindrical body having a first port in communication with a second port by a flow path through the body. The first port, the second port and a solid side wall may be spaced between about 120 degrees and 180 degrees apart around the circumference of the gate.

There is also provided a system including a catheter and a hemostasis valve. The catheter comprises an elongate, flexible tubular body, having a proximal end, a distal end and a central lumen. The hemostasis valve may be provided in a housing on the proximal end of the catheter. The hemostasis valve comprises a collapsible tubular sidewall defining a valve lumen in communication with the central lumen of the catheter. A filament is formed into a loop around the tubular sidewall, the filament having at least a first tail portion extending away from the loop and connecting to a first lever. A first spring is configured to move the first lever in a direction that pulls the first tail portion away from the tubular side wall, reducing the diameter of the valve lumen in response to reducing the diameter of the loop.

The filament may further comprise a second tail portion extending between the loop and a second lever. The first and second levers may be biased in a direction that places the first and second tail portions under sufficient tension to reduce the diameter of the central lumen and provide a seal around a secondary device extending through the valve. The first and second levers may additionally be biased to place the first and second tail portions under sufficient tension to close the valve in the absence of a secondary device extending therethrough.

The inside diameter of the tubing may be continuously controlled from the collapsible valve lumen's original fully opened inside diameter to fully closed, sufficiently to clinically eliminate leakage of blood or other fluid flow through the valve with or without a dilator, guide wire(s), and/or a catheter in the valve lumen. This enables the hemostasis valve to function with no leaking of air or liquid at any state between fully closed and fully open as needed. More than one device may extend side by side through the hemostasis valve (e.g., a guidewire alongside a catheter).

The hemostasis valve may be shipped with a retention feature such as a pin or clip to keep the valve open between production and use. In addition, in some clinical situations it may be desirable to hold the valve open for one or more steps such as to reduce friction with a dilator as it is being advanced or retracted through the valve. A retention feature or clip or control on the housing, which may be in the form of a handle, may be provided to permit selective, temporary locking of the valve open during the procedure as may be desired.

There is also provided an aspiration catheter placement system, comprising a catheter, having an elongate, flexible tubular body with a proximal end, a distal end, a side wall defining a central lumen, and a handle on the proximal end; and a dilator, advanceable through the central lumen. The dilator has an elongate body, cannulated to receive a guidewire, and an axially extending split extending along the entire length or a partial length of the elongate body, configured to allow partial or complete removal of the dilator laterally from the guidewire.

The handle may have a first engagement surface, and the dilator may have a proximal hub with a second engagement surface configured to engage the first engagement surface to releasably secure the dilator within the catheter. The handle may also have a clot container and may also have a hemostasis valve.

There is also provided a method of placing a catheter. The method comprises advancing a catheter and cannulated dilator over a guidewire to an intravascular site, and removing the dilator while leaving the catheter and guidewire in place. The removing step comprises pulling the dilator laterally off of the guidewire as the guidewire progressively passes through an axially extending split in the side wall of the dilator. The method may additionally comprise the step of unlocking the dilator from the catheter prior to the removing step.

In accordance with a further aspect of the present invention, there is provided an aspiration system with accelerated response. The system includes an aspiration pump in communication with a first aspiration pump chamber. An aspiration catheter may be placed in fluid communication with the first chamber by way of an elongate aspiration tube. A second clot collection chamber is in between the aspiration tube and the catheter, and a valve is between the clot collection chamber and the aspiration catheter. Upon opening of the valve, resistance to fluid flow between the clot collection chamber and the distal end of the catheter is less than the resistance to fluid flow between the clot collection chamber and the aspiration pump chamber.

A proximal handle may be provided on the aspiration catheter, and the second chamber may be carried by the handle. The aspiration tube may be at least about 50 inches or at least about 75 inches or 100 inches long.

The valve may be provided with a spring-loaded actuation for momentary valve opening (e.g., by pressing a button or trigger) and automatic closing, or a control such as a switch, lever, or other mechanism that does not automatically close to enable a more sustained open status.

A first control may be provided on the handle for opening the valve. The valve may be normally closed and actuation of the control opens the valve. A second control may be provided for activating the pump.

The second chamber may be configured to capture clot aspirated by the catheter. At least a portion of the second chamber may be removably carried by the handle. The second chamber may comprise a filter membrane spaced apart from a transparent wall. The aspiration system may additionally comprise a filter membrane, spaced apart from a transparent outer chamber wall. The filter and the chamber wall may be tubular.

The aspiration system may further comprise an operator actuated control, configured to toggle a flow regulator between a default low flow mode, and a momentary, operator initiated high flow override mode. The aspiration system may additionally comprise a hemostasis valve carried by the handle.

BRIEF DESCRIPTION OF THE DRAWINGS

FIG. 7A is a schematic view of an alternate configuration of the fluid management system.

DETAILED DESCRIPTION OF THE PREFERRED EMBODIMENT

Figure 1:
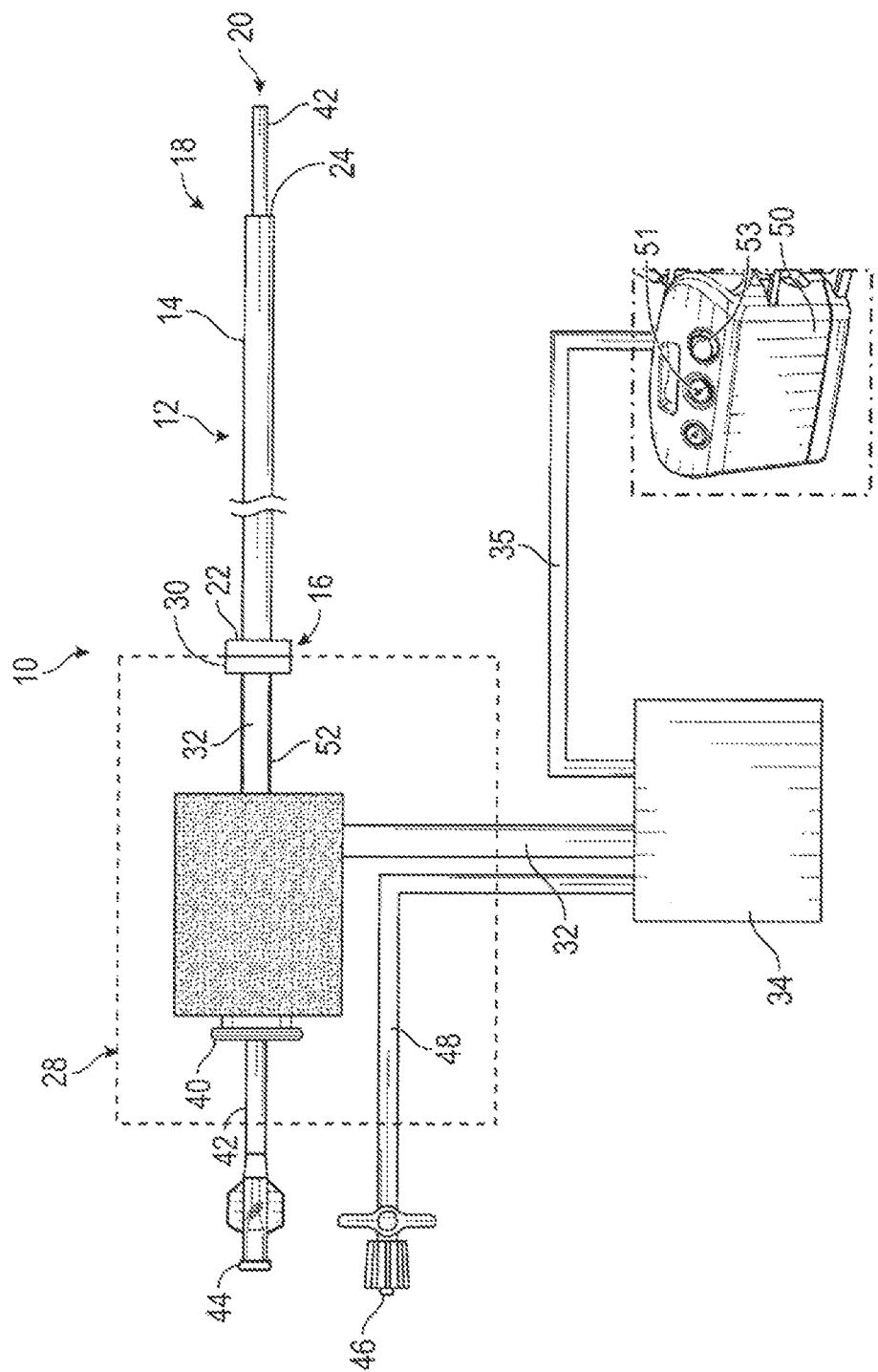
FIG. 1 is a schematic view of a fluid management system in accordance with the present invention.

Referring to FIG. 1, there is illustrated a fluid management system for large bore aspiration procedures. The system 10 includes a large diameter first thrombectomy catheter 12, having an elongate tubular body 14 extending between the proximal end 16 and a distal end 18. A central lumen 20 extends between a proximal catheter connector 22 and a distal port 24 on the distal end 18.

In the illustrated embodiment, the catheter 12 is releasably connectable to a flow control module 28 by way of a complementary module connector 30. Module connector 30 provides a releasable connection to complementary catheter connector 22, and may include an opener (not illustrated) for opening a hemostasis valve in the hub of the large bore catheter (not illustrated).

The flow control module 28 includes a fluid flow path 32 extending between the module connector 30 and the flow control module 28. The fluid flow path 32 continues to extend between the flow control module 28 and a reservoir 34, which contains a filter for thrombus collection and/or evaluation and a chamber for filtered fluid chamber (not illustrated). In an alternate implementation of the invention, the flow control module 28 is integrally formed within the hub of thrombectomy catheter 12 to which the catheter may be non-removably attached. In addition, the flow path between the flow control module 28 and the reservoir 34 may be contained within a continuous integral tubing, or may be contained within two or more tubing components releasably connectable via complementary Luer locks or other connectors.

Flow control module 28 may include a flow regulator for regulating flow through the flow path 32. The flow regulator is configured to provide a reversible restriction in the flow path, such as by an expandable or contractible iris, a ball valve or other rotary core valve, leaf valve, a pinch tubing, or others known in the art.

In one implementation, the flow regulator comprises a collapsible portion of the tubular wall defining the flow path, such as a section of polymeric tubing. An actuator positioned adjacent the tubing is movable between a first position where it compresses the tubing, thereby restricting flow to the low flow rate, and a second position where it has moved away from the tubing, allowing the tubing to resume its full inside diameter and allow the high flow rate. The actuator may be spring biased or have other default driver in the direction of the first (restricted) position, and only movable into the second position in the presence of an affirmative mechanical force or electrical signal that actuates the high flow override. Upon removal of the momentary override command, the actuator automatically resumes the first, position, producing the low flow mode.

The actuator may be driven by a mechanical control such as a lever or rotatable knob, or an electrically driven system such as a solenoid, operated by any of a variety of buttons, levers, triggers, foot pedals or other switches known in the art, depending upon the desired functionality.

In another implementation, the fluid flow may be selectively directed through a low flow regulator such as a small diameter orifice or tube, and a high flow regulator such as a larger diameter orifice or tube. A mechanically actuated or electromechanically actuated valve can momentarily divert flow from the low flow to the high flow regulator in response to actuating a control.

Flow control module 28 thus includes one or more controls, for controlling the operation of the system. One control may be provided for toggling the system between a no flow (off) mode and a low flow mode. The same or a different control may be provided for momentarily toggling the flow regulator between the low flow mode and a momentary operator initiated high flow override mode. Release of the momentary override control causes the regulator to revert to off or low flow mode.

The low flow mode enables the first catheter 12 to approach and engage the clot with a relatively low volume of blood aspiration. Once the clot is engaged, the momentary high flow control may be activated to generate a bolus of high flow vacuum to draw the clot into the catheter 12. High flow may be at least about 10 cc/second, and preferably at least about 15 cc/sec but typically no more than about 25 cc/sec. In one construction the high flow rate is about 20 cc/sec, with all of the foregoing flow rates in an unobstructed aspiration of blood. Low flow as used herein is no more than about 50%, no more than about 35% or no more than about 25% of the high flow rate. Low flow is generally less than about 10 cc/sec or 7 cc/sec, and is often in the range of from about 1-5 cc/sec.

The flow control module 28 may be provided with a second catheter port 40 in communication with central lumen 20 via a hemostasis valve (e.g., Tuohy Borst valve) (not illustrated) within the module 28. This allows introduction of a second aspiration catheter 42 through the access catheter 12 and extending to the treatment site. The second catheter 42 may be a smaller diameter aspiration catheter, with or without clot agitation or mechanical grasping capabilities, drug delivery catheter, a mechanical disrupter or other accessory device that may be useful in the clot retrieval process. In one implementation, the second catheter including its hand piece and controls may be identical in material respects to the first aspiration catheter except the second catheter is smaller diameter and longer than the first catheter.

If desired, the second catheter 42 may be connected via a proximal connector 44 to a complementary connector 46 which is in communication with the reservoir 34 via aspiration line 48. Alternatively, aspiration line 48 may be connected to a separate aspiration and collection system (not illustrated).

The clot may be removable through the first catheter 12 under vacuum without additional assistance. However, if desired, the secondary clot grasping catheter 42 may be introduced to provide additional attachment and/or mechanical disruption of the clot to facilitate removal. Removal may be assisted by the application of vacuum to the grasping catheter 42 as well as to the first catheter 12 in sequence or simultaneously depending upon the desired clinical performance.

Aspiration pump 50 may include a vacuum pump, and may also include a vacuum gauge 51, and an optional a pressure adjustment control 53. The vacuum gauge 51 is in fluid communication with the vacuum pump and indicates the vacuum pressure generated by the pump. The pressure adjustment control 53 allows the user to set to a specific vacuum pressure. Any of a variety of controls may be utilized, including switches, buttons, levers, rotatable knobs, and others which will be apparent to those of skill in the art in view of the disclosure herein. Aspiration pump 50 may alternatively be a manually activated pump such as a syringe.

Reservoir 34 is in fluid communication with the aspiration pump 50 via vacuum line 35 and acts to transfer vacuum from the air filled side of the system to the liquid side of the system, and also to collect aspirated blood and debris. Vacuum line 35 may be used as a flow restriction. Reservoir 34 thus includes a collection canister in fluid communication with flow path 32 and collects aspirated debris. The collection canister may include a filter that collects clot, which may be visually observed or accessed through a window to monitor progress of the procedure and/or used for pathologic diagnosis. The vacuum chamber and collection canister may be separate components that are in fluid communication with each other or merged within a single housing. The flow direction through the system may also be reversed to allow the blood to flow through the filter while the clot is collected outside (now downstream) of the filter, e.g., between the filter and the outer transparent window or container.

The flow path 32 extends throughout the length of the first catheter 12, through the control module 28 and into the reservoir 34. A transparent window 52 may be provided to enable direct visualization of the contents of the flow path 32. In the illustrated embodiment, the window 52 is in the form of a transparent section of tubing between the proximal end of the access catheter 12 and the flow module 28, and within the sterile field so that the clinician can directly visualize debris as it exits the proximal end of the access catheter 12 and before it reaches the reservoir 34 which may be outside of the sterile field. The actual length of the transparent tubing is preferably at least about two or four or 6 cm long and generally less than about 30 or 20 cm long. In some implementations, the length of the transparent tube is within the range of about 5 cm to about 15 cm. In an alternate implementation, the transparent window may be carried by the proximal hub of the access catheter 12, or may be a proximal portion of the catheter shaft, distally of the hub.

Figure 2:
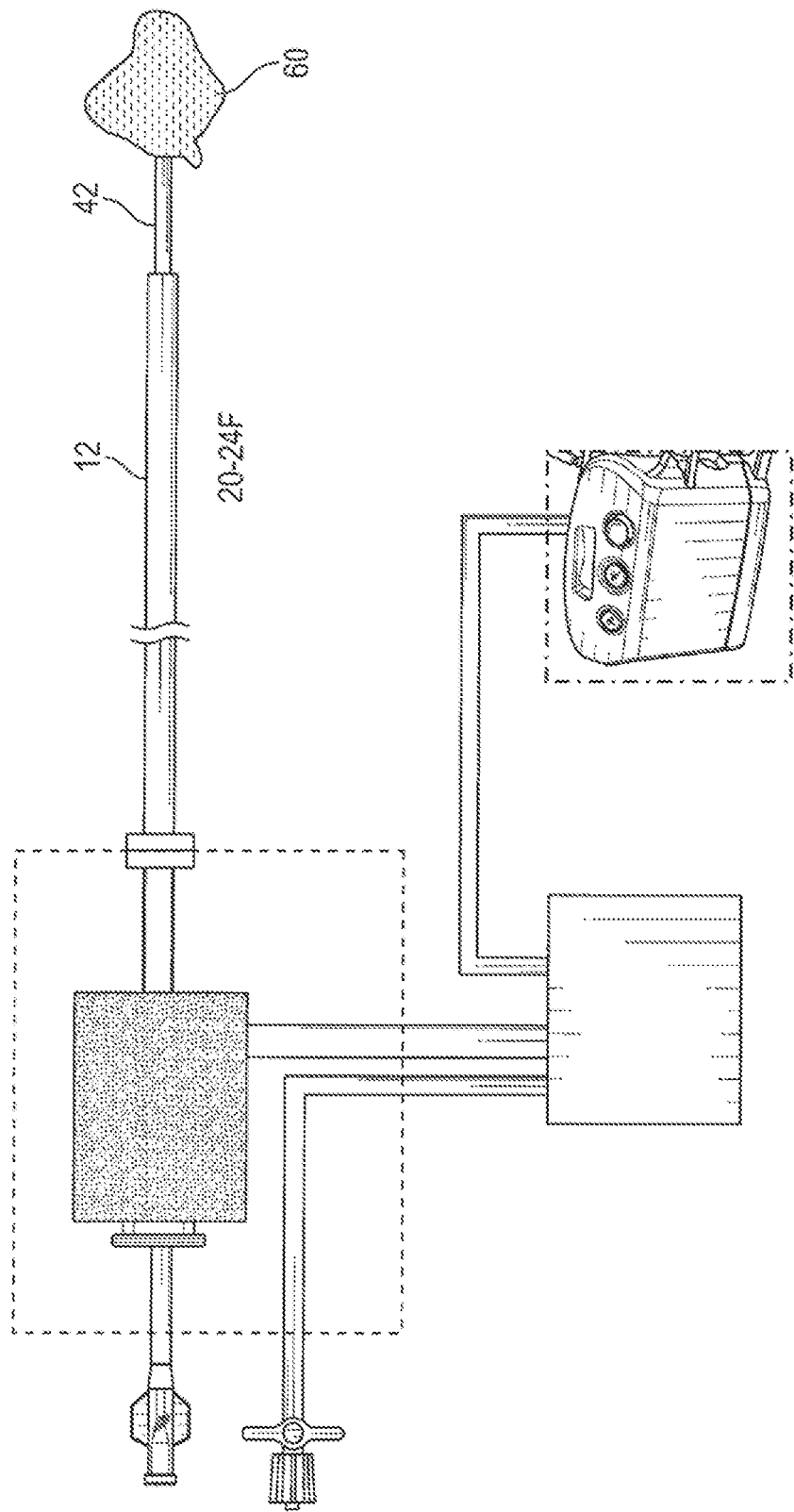
FIG. 2 is a schematic view as in FIG. 1, with a clot attached to a grasping catheter which extends through a large diameter catheter.

Referring to FIG. 2, the secondary catheter is in the form of a second aspiration catheter 42 which has been distally advanced through the access catheter 12 and through the vasculature into proximity with a clot 60. The clot 60 may be grasped by the second catheter 42 in any of a variety of ways such as by mechanical attachment or suction, or both.

Figure 3:
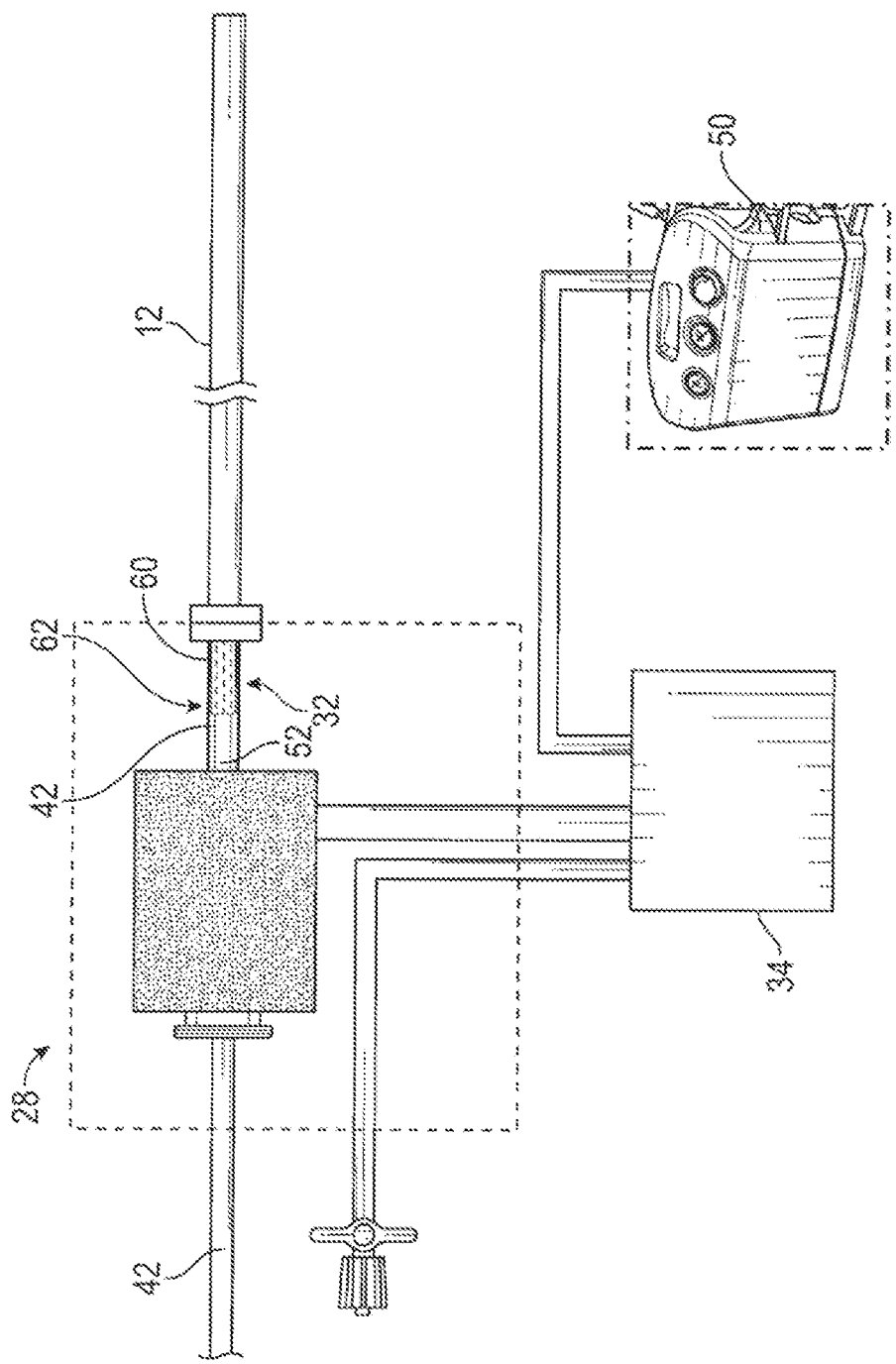
FIG. 3 is a schematic view as in FIG. 2, with the clot drawn into a transparent viewing tube on the large diameter access catheter.

Referring to FIG. 3, the second catheter 42 has been partially proximally retracted, drawing the clot 60 into the first catheter 12 such that the clot 60 becomes visible through the window 52. This may be facilitated by applying vacuum through both the grasping catheter 42 and the access catheter 12.

Continued proximal retraction of the grasping catheter 42 brings an interface 62 between the grasping catheter 42 and the clot 60 into view through the window 52. This enables the clinician to visually confirm that a clot has been captured.

Figure 4:
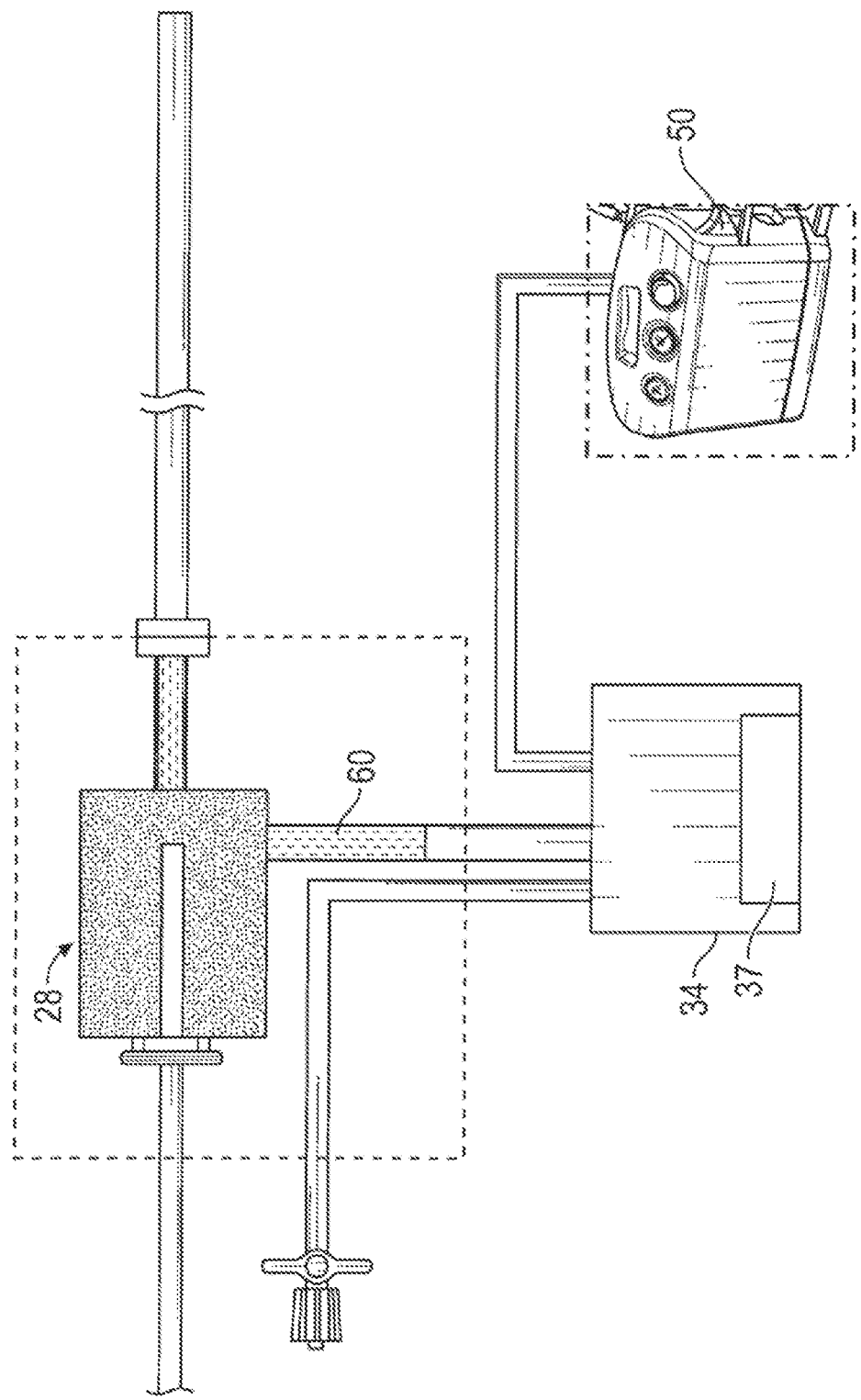
FIG. 4 is a schematic view as in FIG. 3, with the clot advancing towards a thrombus collection chamber.
Figure 5:
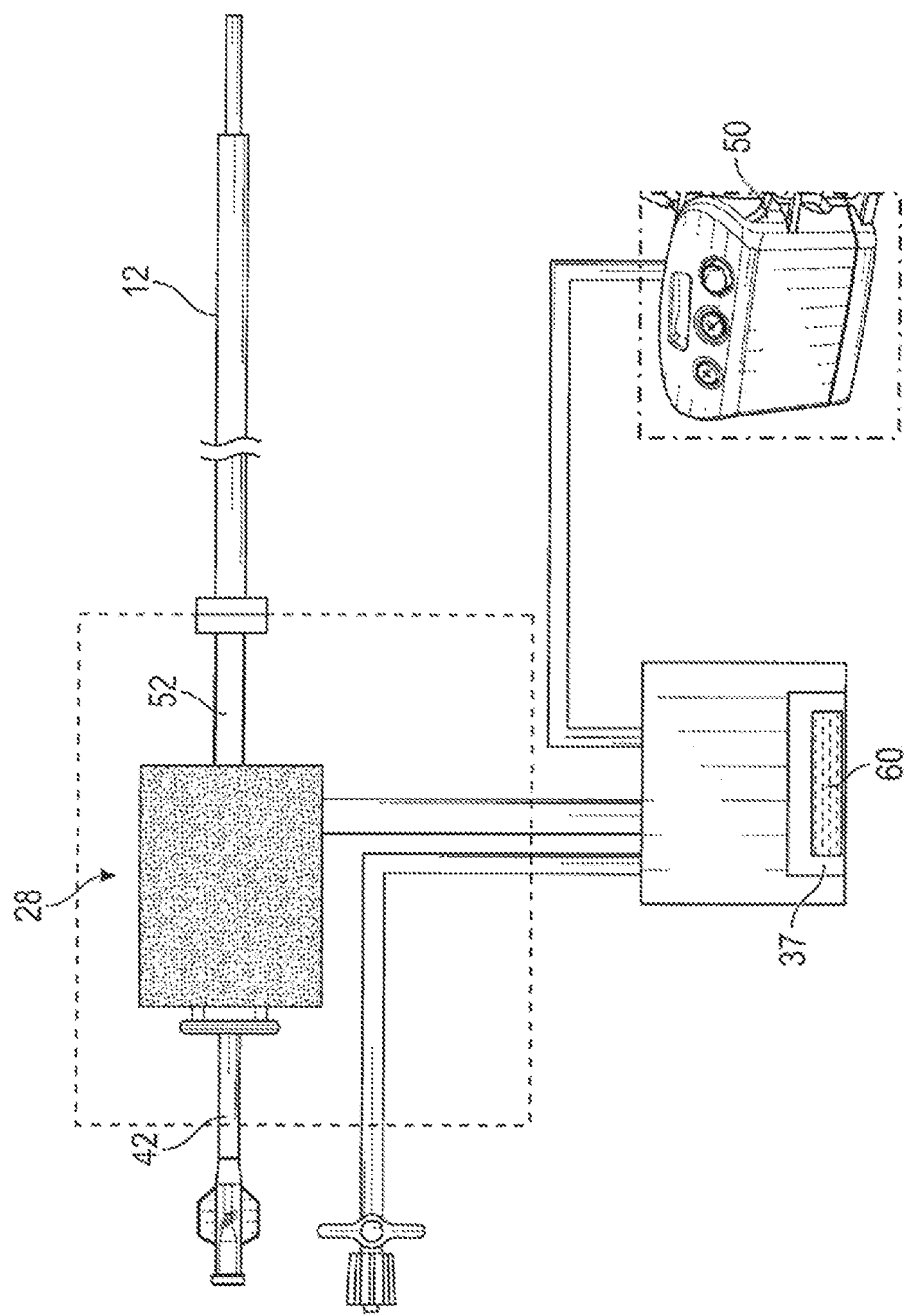
FIG. 5 is a schematic view as in FIG. 4, with the clot deposited in a transparent thrombus collection chamber.

Referring to FIG. 4, further proximal retraction of the grasping catheter 42 allows the clot 60 to be drawn through the flow path 32 in the direction of the reservoir 34. The clot 60 is there after drawn by vacuum into the collection chamber within reservoir 34, where it may be captured by a filter and viewed through a transparent sidewall or window 37 on the collection chamber.

Figure 6:
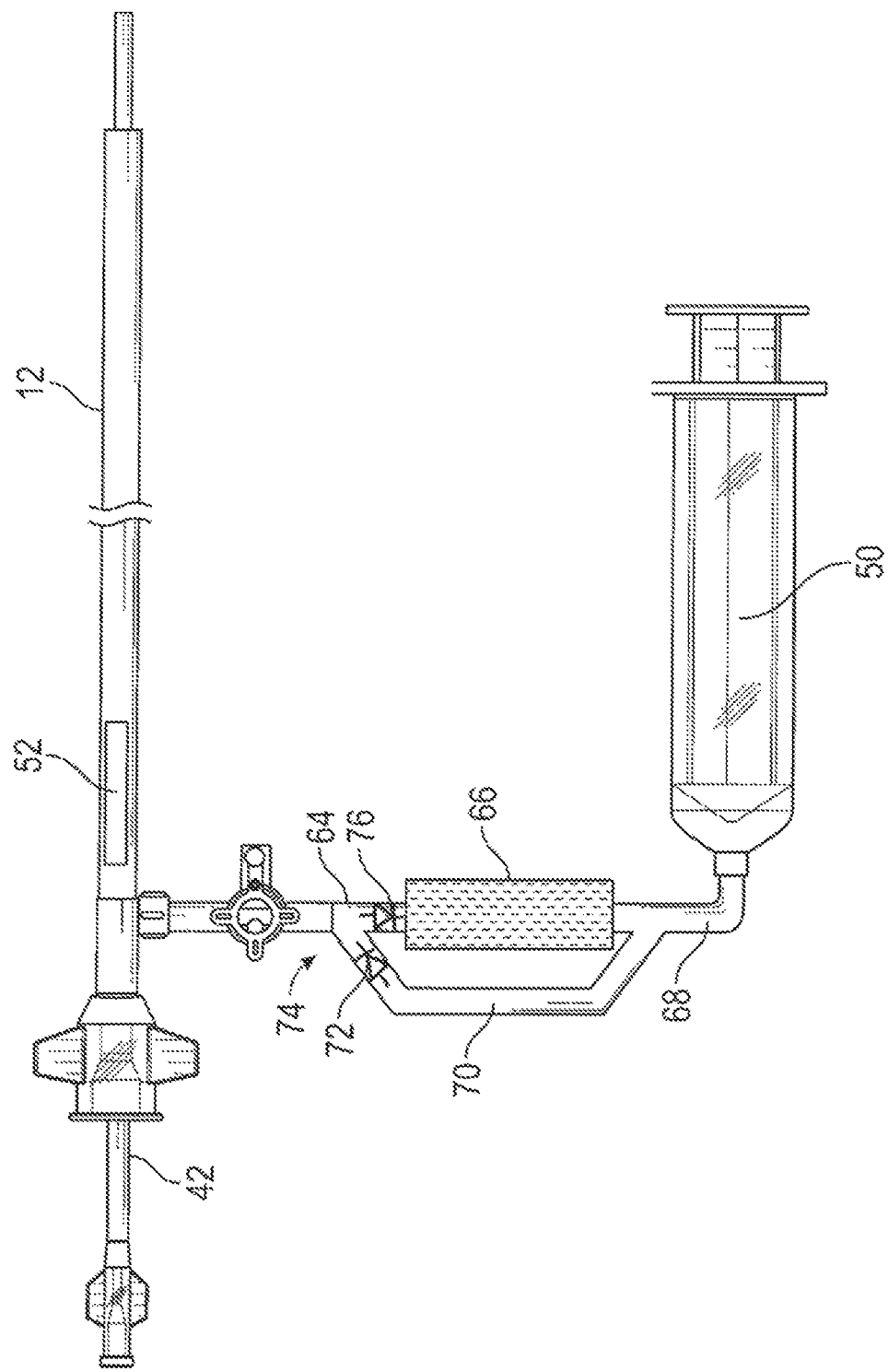
FIG. 6 is a schematic view of a thrombectomy system configured to re-infuse filtered aspirated blood back into a patient.

Another aspect of fluid management during the thrombectomy procedure is illustrated in FIG. 6. In this implementation, an aspiration line 64 places the first catheter 12 in communication with a thrombus filter 66. The thrombus filter 66 is further in communication with a pump such as a syringe aspiration pump 50 by way of aspiration line 68. Actuation of the pump 50, such as by proximally retracting the plunger, draws thrombus through the access catheter 12 and into the thrombus filter 66 where thrombus and thrombus particles having a size greater than a predetermined threshold will be entrapped. The thrombus filter 66 may be provided with a transparent window for a visual confirmation, as has been discussed.

Blood drawn into the syringe 50 will therefore be filtered, with the debris remaining in the thrombus filter 66. Blood in the pump 50 or other reservoir downstream from the filter may be re-infused into the patient. In the illustrated configuration this may be accomplished by reversing the pump (pushing the plunger) and pushing filtered blood via a bypass tube 70 which merges with the flow path 32 on the patient side of the filter 66 and back into the patient. A valve assembly 74 is preferably provided to direct thrombus containing blood from the patient into the filter 66 but ensure that only filtered blood can be pumped through bypass 70 and back into communication with the flow path 32 and into the patient.

In the illustrated implementation, the valve assembly 74 comprises a first valve 72 in the bypass tube 70 which permits flow of filtered blood in the direction of the patient but blocks the flow of unfiltered blood through the bypass tube 70 in the direction of the pump 50. The second valve 76 is provided to permit flow of unfiltered blood in the direction of the filter 66 but prevent the flow of blood from the filter back in the direction of the patient. In one execution of the invention, the first valve 72 and second valve 76 are one way flapper valves that open or close in response to blood flow direction.

A further configuration of the fluid management system is schematically illustrated in FIG. 7A. Aspiration line 64 places the first aspiration catheter 12 in communication with the thrombus filter 66. The thrombus filter 66 is in communication with the aspiration pump 50 by way of aspiration line 68. Aspiration line 68 includes a flow control 76. Flow control 76 includes an off/on control such as a switch 78. Activation of the switch 78 to the 'on' configuration places the system in a low flow vacuum mode as has been discussed. Activation of a momentary full flow control such as a button 80 changes the system to the high flow mode.

Figure 7B:
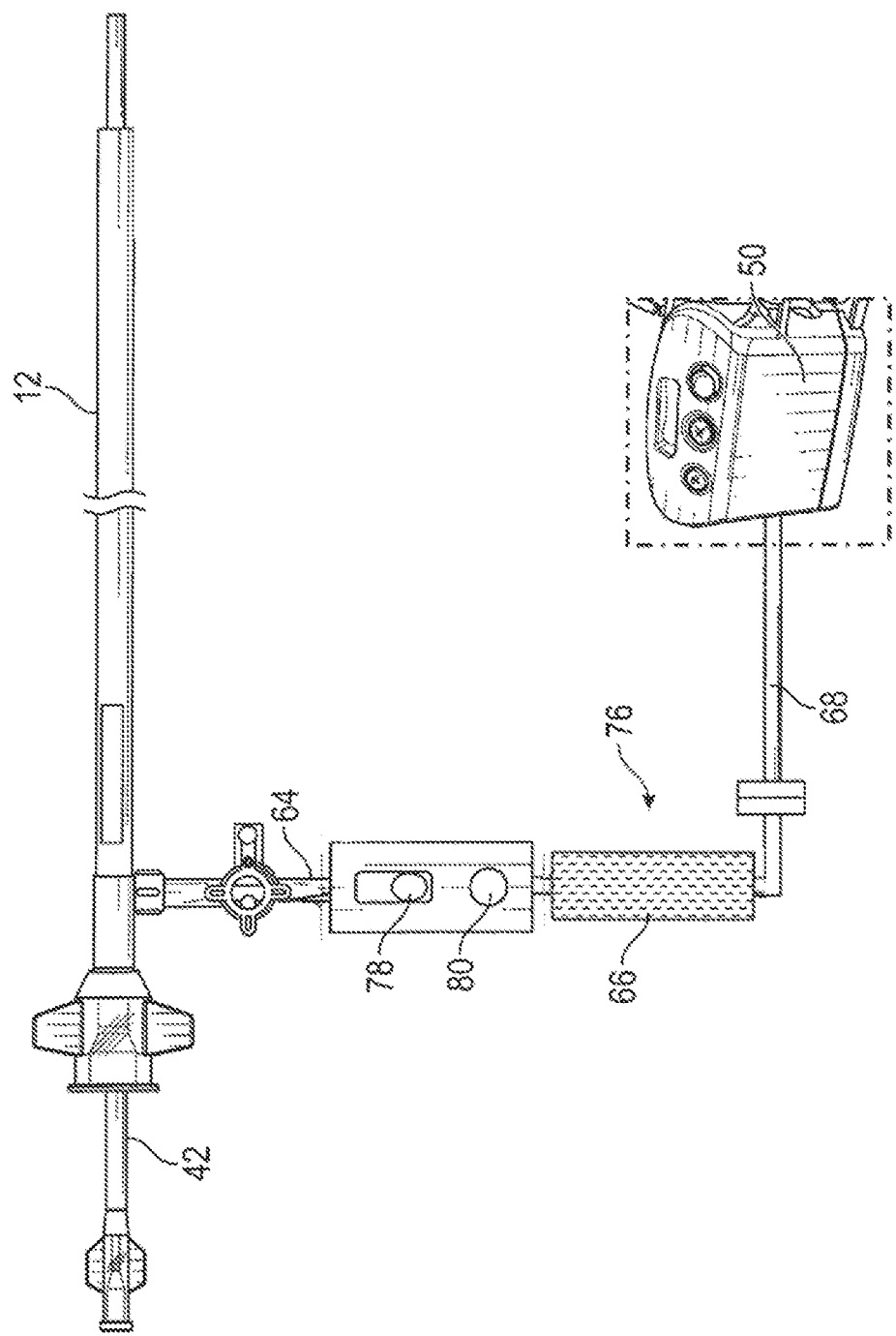
FIG. 7B is a schematic view of an alternate configuration of the fluid management system.

In an alternate configuration illustrated in FIG. 7B, the flow control 76 is moved from between the aspiration pump 50 and thrombus filter 66 to in between the catheter and the thrombus filter 66. This allows the negative pressure in the chamber of thrombus filter 66 to reach equilibrium with the canister in the aspiration pump 50 when the valve in flow control 76 is closed. When the valve is subsequently opened, the relatively short distance between the thrombus filter and the patient allows a rapid drop in negative pressure at the distal end of the catheter as is discussed in greater detail in connection with FIG. 11B. The flow control 76 my additionally be provided with an optional vent to atmosphere, or to no vacuum, or vent to a source of vacuum at a milder vacuum than that experienced in the cannister of the aspiration pump 50.

Figure 8:
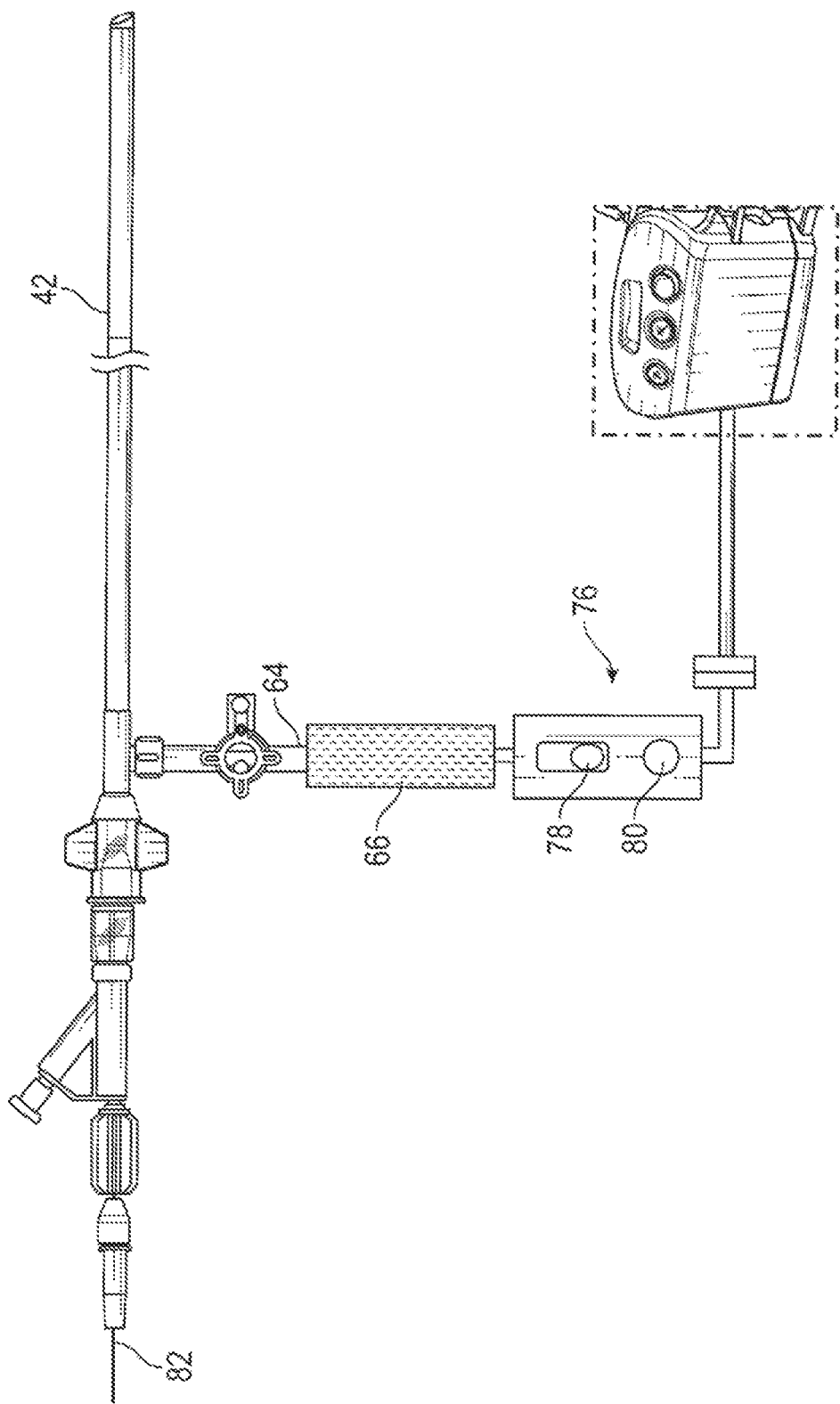
FIG. 8 is a schematic view of a grasping catheter configured to apply suction to a clot.

FIG. 8 illustrates a second, smaller aspiration catheter 42 such as a 16 French catheter, configured for the application of suction to facilitate grasping a clot. In a typical configuration, the second catheter 42 will be extended through a first, larger catheter 12 (not illustrated) as has been discussed. As with any of the second catheters disclosed herein, a mechanical agitator 82 may be axially movably positioned within a central lumen of the grasping catheter 42. See also FIGS. 16A-18B. Additional details of one suitable mechanical agitator 82 are disclosed in U.S. Pat. No. 10,653, 434 to Yang, et al., entitled Devices and Methods for Removing Obstructive Material from an Intravascular Site, the entirety of which is hereby expressly incorporated herein by reference. Additional details of the mechanical agitator 82 are disclosed in U.S. patent application Ser. No. 15/443, 874, filed Feb. 27, 2017, entitled Telescoping Neurovascular Catheter with Enlargeable Distal Opening, and U.S. patent application Ser. No. 16/398,626, filed Apr. 30, 2019, entitled Devices for Removing Obstructive Material from an Intravascular Site, the entireties of which are hereby expressly incorporated herein by reference.

Figure 9:
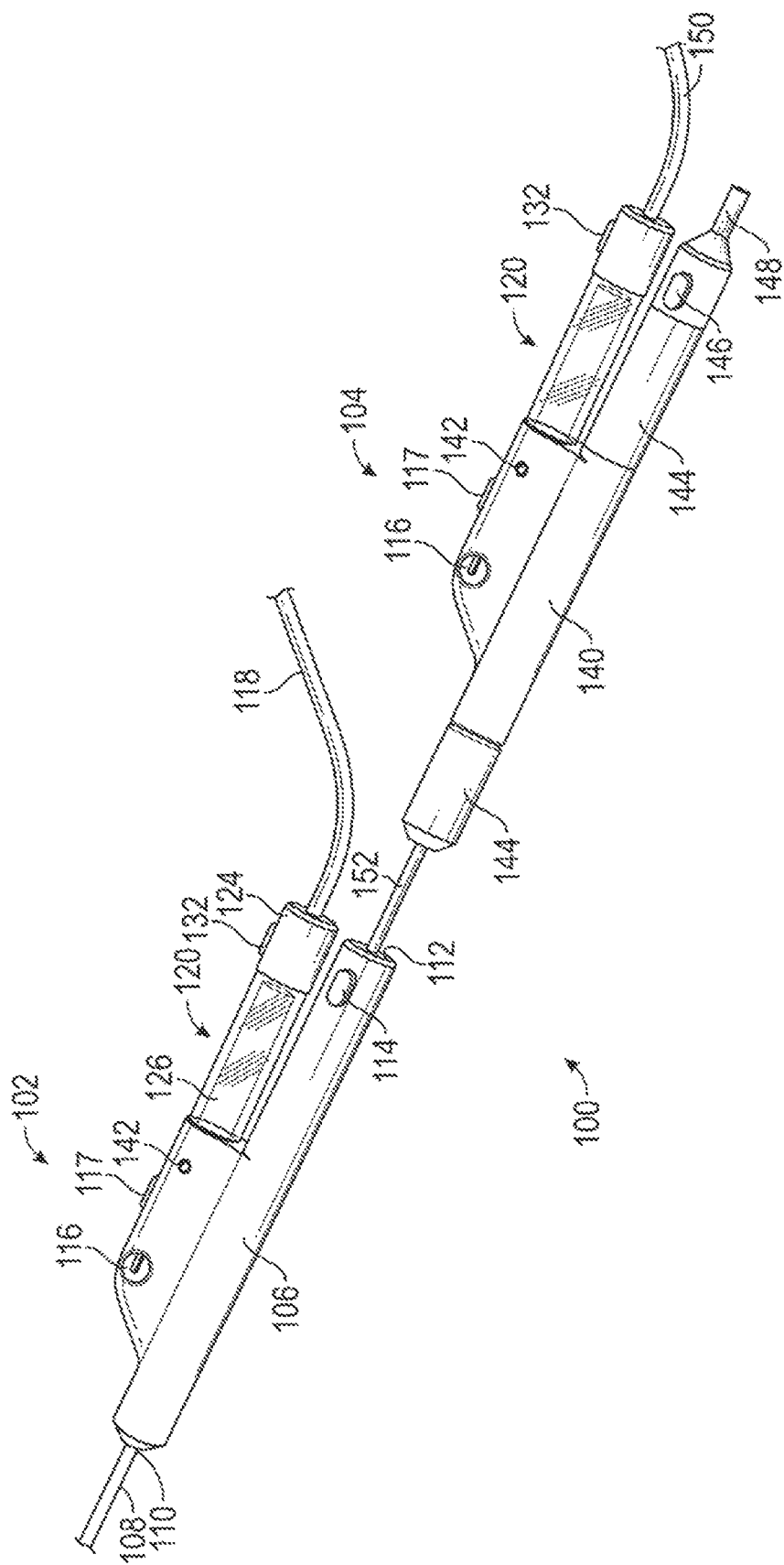
FIG. 9 is a schematic view of an alternative aspiration system in accordance with the present invention, having a first thrombectomy catheter and a second thrombectomy catheter extending therethrough.
Figure 10A:
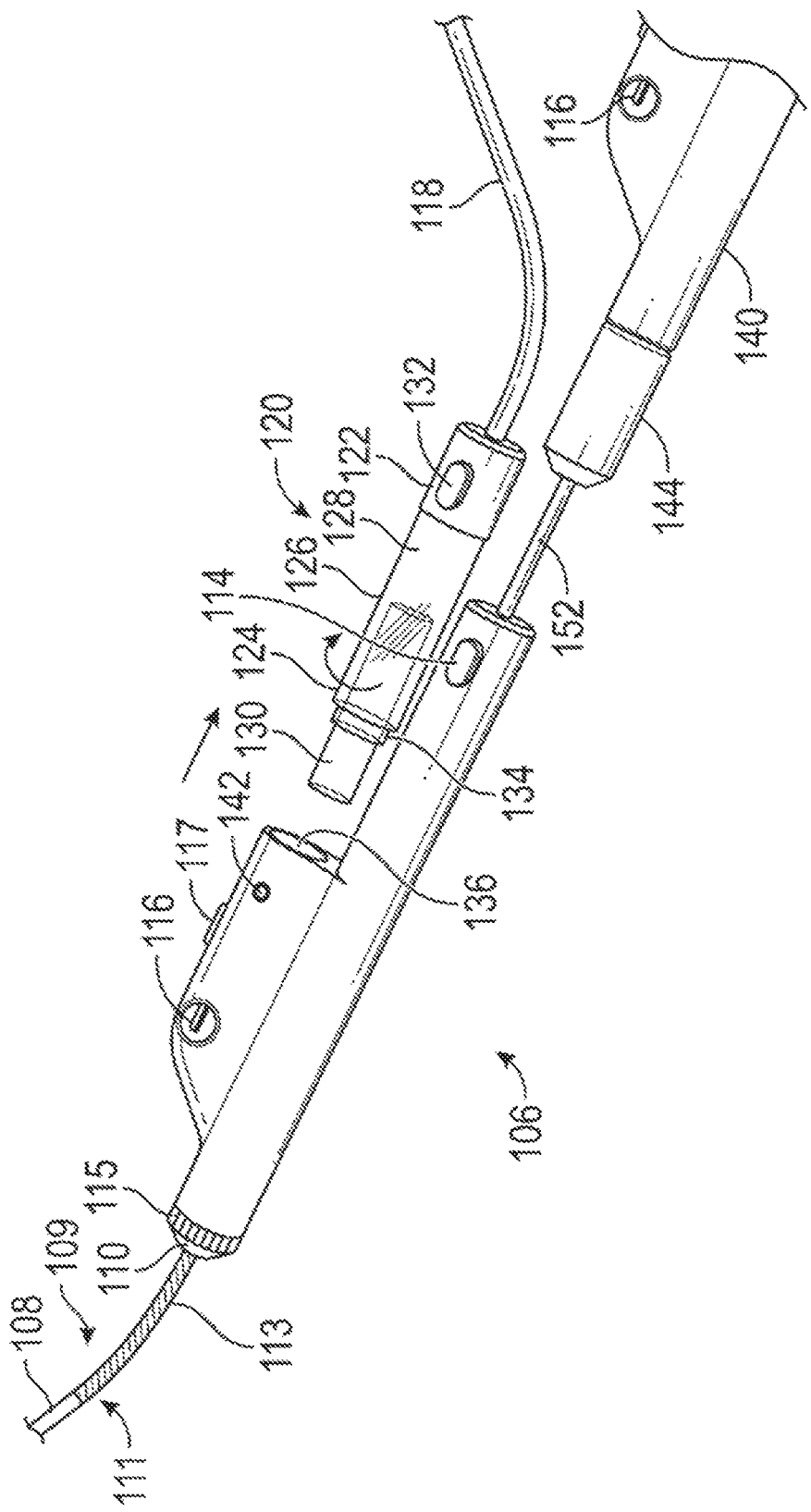
FIG. 10A is a schematic view of the hand piece for the first thrombectomy catheter of FIG. 9.

Referring to FIGS. 9 and 10A, there is illustrated a further implementation of an aspiration system 100. The system includes a first thrombectomy catheter 102, such as a large bore aspiration catheter, and a second aspiration catheter 104 which is optionally advanceable through the first thrombectomy catheter 102 as has been discussed, or used by itself.

Thrombectomy catheter 102 comprises a proximal handle 106 having an elongate flexible tubular catheter body 108 extending distally therefrom. The proximal end 110 of the tubular body 108 may be permanently carried by the proximal handle 106 or may be provided with a releasable connector for detachable connection to a complementary connector on the handle 106.

In one implementation of the invention, the tubular body 108 or 152 or both are provided with a flexible neck 109 extending between proximal end 110 and a transition 111. The flexible neck 109 has a greater flexibility than the adjacent portion of the tubular body 108 distal to the transition 111. The flexible neck 109 may have a length of at least about 2 cm and often at least about 4 cm, but generally no more than about 20 cm or 10 cm or less.

The sidewall of the catheter body 108 within flexible neck 109 includes a helical coil 113 having adjacent filars spaced apart to both improve flexibility, and also allow visualization between adjacent windings of the coil. At least the flexible neck 109 includes a sidewall window such as the spaces between adjacent coil windings which may be in the form of an optically transparent outer tubular layer, such as any of a variety of optically transparent shrink tubing polymers. This allows visualization of clot through the side wall as it passes through the neck 109 before it enters the proximal handle. The transparent window on the larger catheter 108 also allows visualization of the distal tip of the inner catheter 152 as it passes the window. This may be facilitated by placing a visual marker on the distal end of the inner catheter 152 such as a colored annular band.

For example, in an implementation having a 24 French tubular body 108, the smaller tubular body 152 (e.g., 16 French catheter) may be provided with a visual indicium such as a white tip on the distal end, that can be visualized through the sidewall window as it passes through the flexible neck 109. The flexible neck 109 may also be provided on the catheter shaft 152.

The spring coil 113 may extend distally to a point of termination within about one or 2 cm of the transition 111, and, and one implementation, at the transition 111. Distally of the transition, the sidewall of tubular body 108 may include a tubular braid, importing greater stiffness and higher push ability than the helical coil 113.

The proximal end of the catheter may be provided with a rotation control such as a rotatable knob 115 which may be rotationally fixed to the catheter and rotatable with respect to the handle housing. This facilitates relative rotation between the catheter and the housing for any of the large or small bore catheters disclosed herein.

A central lumen extending through the tubular catheter body 108 is in communication with a flow path extending through the proximal handle 106 to a proximal access port 112. The flow path between the tubular catheter body 108 and the proximal access port 112 is preferably linear, to axially movably receive the second catheter 104 which may or may not be utilized in a given procedure. To accommodate the absence of second catheter 104 and seal the port 112, the proximal handle 106 is preferably provided with a homeostasis valve 114 such as a Touhy-Borst valve.

A manifold switch 116 controls two way or three way a manifold valve (illustrated in FIG. 12) for selectively controlling fluid flow as discussed further below. An aspiration control 117 is provided to turn aspiration on and off. Alternatively, manifold switch 116 can be configured to turn aspiration one and off.

A filter assembly 120 includes housing 122 with a side wall 124, at least a portion of which includes a transparent window 126. Window 126 permits a viewing of the contents (e.g. aspirated clot) of a filter chamber 128, which contains a filter 130.

The filter assembly 120 is configured to place the filter 130 in the flow path between the tubular catheter body 108 and the aspiration tubing 118. Preferably the filter chamber can be closed to maintain negative pressure conveyed from a pump via aspiration tubing 118, or opened to permit insertion or removal of the filter 130. In the illustrated implementation, the filter assembly 120 is removably connected to the handle 106. A connector 134 such as a first thread on the housing 122 is releasably engageable with a complementary connector 136 such as a complementary thread on the handle 106. A vent (aperture) to atmosphere may be provided in communication with the filter chamber, to reduce foaming of blood in response to reduced pressure.

The present implementation of the invention includes an integrated flow control module in the proximal handle 106. Thus, an adjustable flow regulator (not illustrated) may be positioned in the flow path, to enable controllable toggling of the aspiration between a low flow mode and a high flow mode. In the illustrated implementation, optional flow regulator is positioned downstream of the filter 130, and contained within the housing 122 of the filter assembly 120. A flow regulator control 132 is provided, to control the flow rate. Preferably, as has been discussed, the flow regulator is configured to regulate fluid flow through the flow path at a default low flow rate. Activation of the flow control 132 adjust the flow to the high flow rate mode. Flow control 132 may be a momentary button, slider switch, trigger, knob or other structure that is preferably defaulted to the low flow mode.

In any of the catheters disclosed herein, carrying the filter chamber 128 on the catheter or at least spaced apart from the remote vacuum pump and vacuum cannister provides enhanced aspiration performance. The location of a conventional aspiration pump may be far enough away from the patient to require a length of aspiration tubing between the pump and the catheter to be as much as 50 inches or 100 inches or more. The pump typically includes an aspiration canister for blood collection. When aspiration is desired, a valve is opened to place the low pressure cannister in communication with the catheter by way of the aspiration tubing, to aspirate material from the patient. But the length of the aspiration tubing operates as a flow restrictor, causing a delay between the time of activating the vacuum button and actual application of suction to the clot.

In accordance with the present invention, the catheter handle 106 or 140 contains a filter chamber 128 for example, which is in communication with the vacuum cannister on the pump by way of elongate aspiration tubing 118. The momentary aspiration control 117 is in between the filter chamber 128 and the catheter, which, in the default off position, allows the entire length of the aspiration tubing 118 and the filter chamber 128 to reach the same low pressure as the aspiration cannister on the pump. The flow restriction between the pump cannister 129 and the filter chamber 128 is greater than the flow restriction between the filter chamber 128 and the patient.

In an alternate configurations, 117 may be a vent to atmosphere which allows the clot canister to be evacuated. Element 142 can alternatively be an injection port such as for injecting contrast media, saline, or drugs.

Thus, the only remaining flow restrictor between a source of vacuum (filter chamber 128) and the patient is the relatively short aspiration pathway between the valve in the handpiece and the distal end of the catheter. When the momentary aspiration control 117 is activated, the flow restriction and enclosed volume on the patient side of the filter chamber is low relative to the flow restriction and enclosed volume through aspiration tubing 118 on the pump side of the filter chamber 128.

This dual chamber configuration produces a rapid spike in negative pressure experienced at the distal end of the catheter upon activation of the aspiration control 117. The response time between activating the aspiration control 117 and realizing suction actually experienced at the clot is significantly faster and allows significantly higher initial flow than the response time realized in a conventional system having only a vacuum chamber located at the pump.

The spike of negative pressure experienced at the distal end of the catheter will fade as pressure equilibrium is reached between the filter chamber and canister. When the momentary aspiration control 117 is closed, the vacuum pump will gradually bring the pressure in the filter chamber 128 back down to the level in the vacuum cannister at the pump.

Figure 11A:
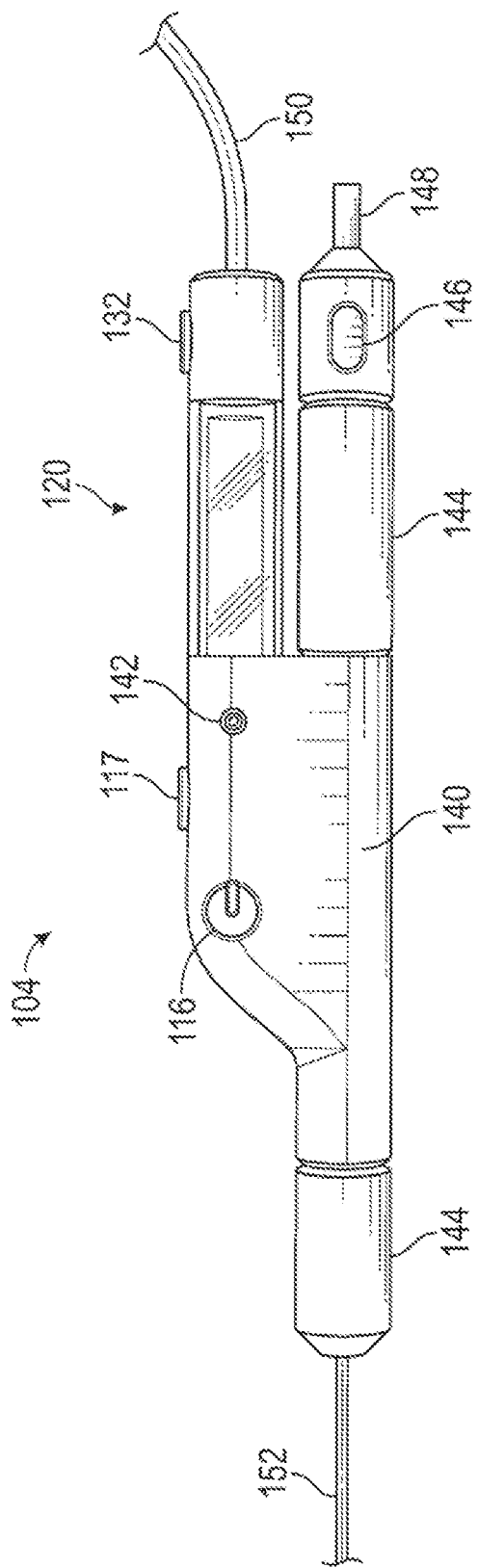
FIG. 11A is a schematic view of the handpiece for the second thrombectomy catheter of FIG. 9.
Figure 11B:
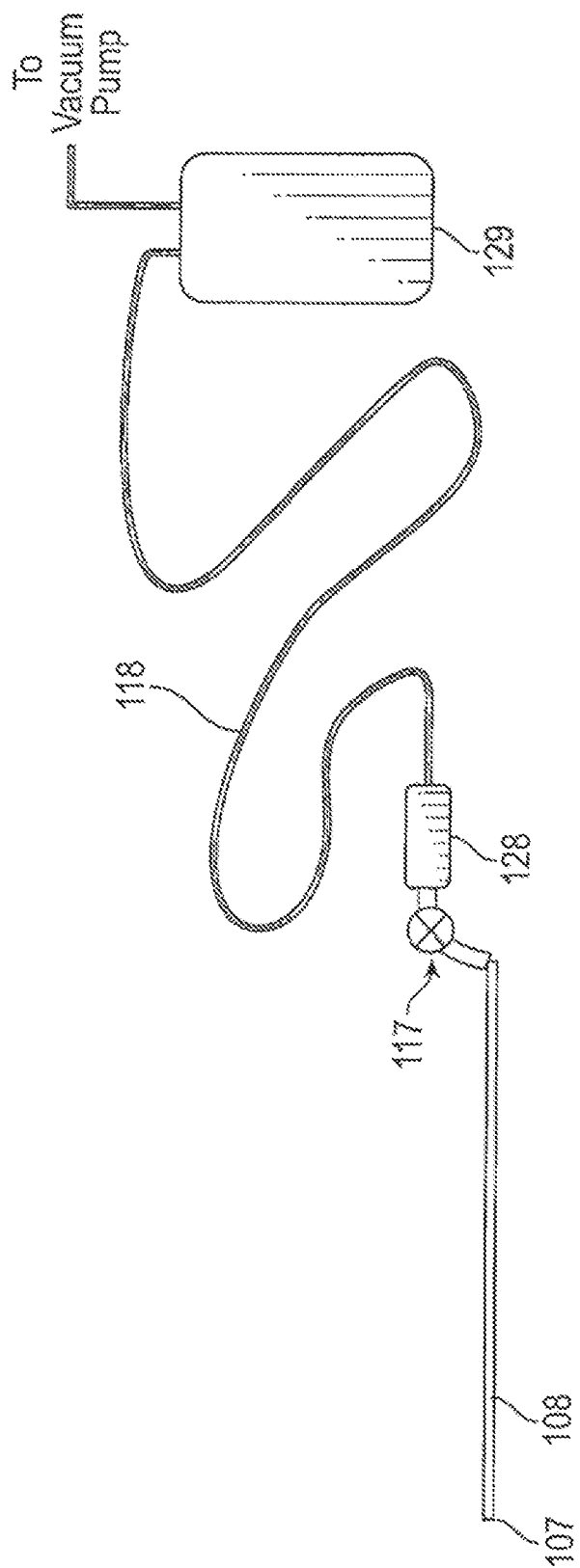
FIG. 11B is a simplified flow diagram of the dual vacuum chamber aspiration system.
Figure 11C:
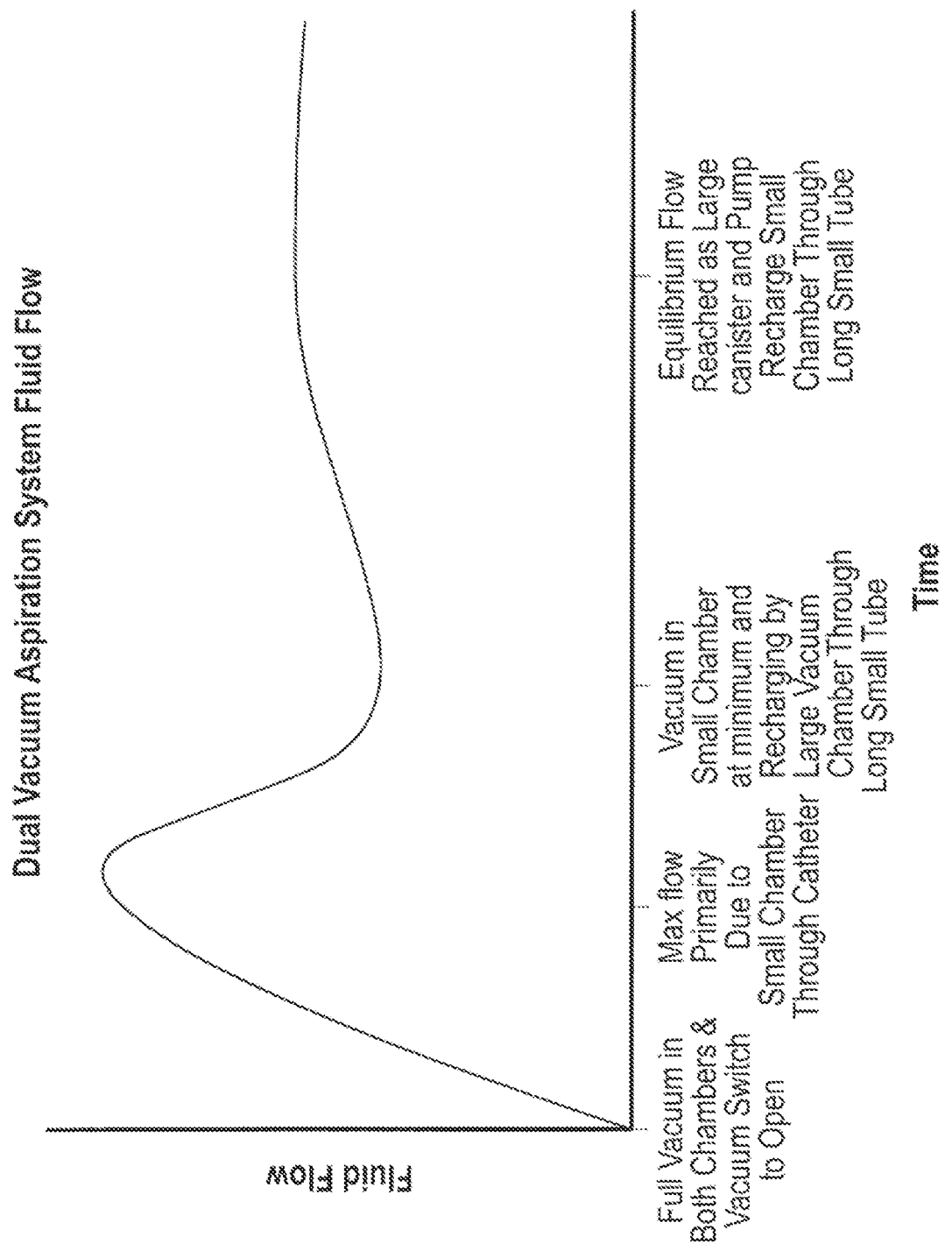
FIG. 11C is a qualitative fluid flow rate diagram at the catheter tip, following opening of the momentary vacuum control valve.

A simplified fluid flow diagram is illustrated in FIG. 11B, and a qualitative flow rate diagram is illustrated in FIG. 11C. The flow restriction between chamber 128 and the distal and 107 of catheter 108 is small relative to the flow restriction between the vacuum canister 129 and the vacuum chamber 128. This allows a negative pressure peak experienced at distal end 107 almost instantaneously upon activation of vacuum switch 117. The flow rate of material into the catheter 108 rapidly reaches a peak and subsides as vacuum chamber 128 fills with aspirated material. The vacuum in chamber 128 declines to a minimum, and slowly recharges by the large vacuum chamber 129 and associated pump through tubing 118. In use, a clinician may choose to allow the momentary vacuum switch 117 to close at or shortly following the maximum flow rate, just giving a short burst or spike of vacuum to facilitate aspiration of thrombus into the catheter 108.

Figure 10B:
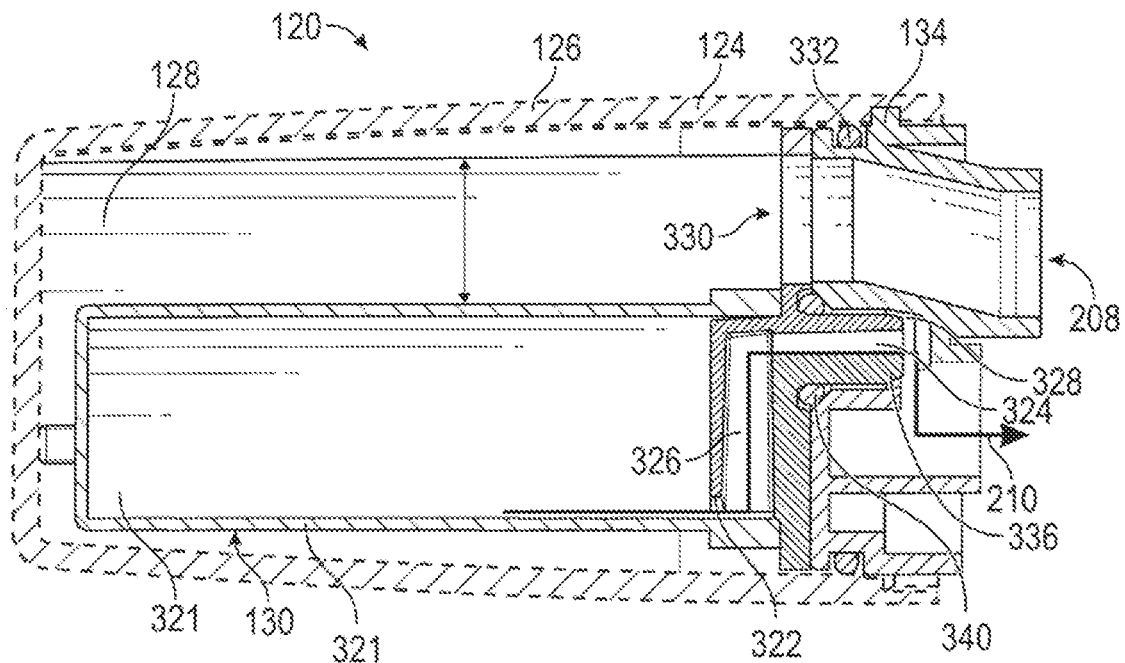
FIGS. 10B-10E illustrate interface details between a filter assembly and a handpiece.
Figure 10C:
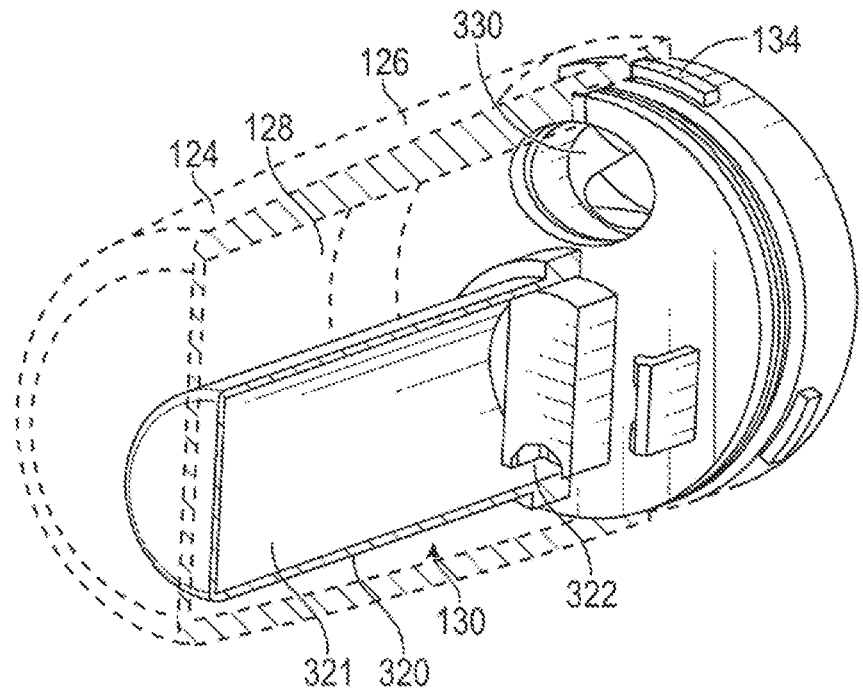

Additional details of the filter assembly and related structures are illustrated in FIGS. 10B to 10E. Referring to FIG. 10B, the filter assembly 120 includes a tubular sidewall 124 having a transparent window 126. In some implementations the entire tubular sidewall 124 can be a transparent window. The side wall 124 encloses a filter 130 as has been discussed. The filter 130 includes a tubular filter sidewall 320 defining an interior chamber 321 for filtered blood. Filtered blood is drawn in the direction of vacuum line 210 through a first vacuum aperture 322 and into a flow path 324 having a vertical offset 326 in the flow path 324. The vertical offset 326 allows removal of blood from the bottom of the chamber, through a flow path and out through a second vacuum aperture more centralized with respect to a central axis of the tubular sidewall 124 and in communication with vacuum line 210.

The filter 130 is displaced downward with respect to a central longitudinal axis of the tubular sidewall 124, leaving the filter chamber 128 having a chamber height 129 at least as great as the inside diameter of a filter line aperture 330 leading to filter line 208. This allows clot to move from filter line 208 into the filter chamber 128 without restriction, and optimizes the volume of filter chamber 128 on top of the filter 130 for viewing through the window 126.

A connector 134 may be carried by the filter assembly 120, such as in the form of a bayonet mount, or other releasable attachment to the handpiece housing. A first seal 332 such as an annular elastomeric ring may be provided between the tubular sidewall 124 and the complementary surface on the handpiece housing.

A second vacuum aperture 328 is in communication with the first vacuum aperture 322 by way of the flow path 324. Second vacuum aperture 328 may be carried on an axially extending tubular projection 336 which may be removably received within a complementary recess on the hand piece housing.

A second seal 340 such as an elastomeric ring may be provided surrounding the flow path 324, for providing a seal between the filter assembly and the handpiece. In the illustrated implementation, the second seal 340 surrounds the tubular projection 336 and is configured to seal against an adjacent complementary surface on the handpiece in the as mounted orientation.

Figure 10D:
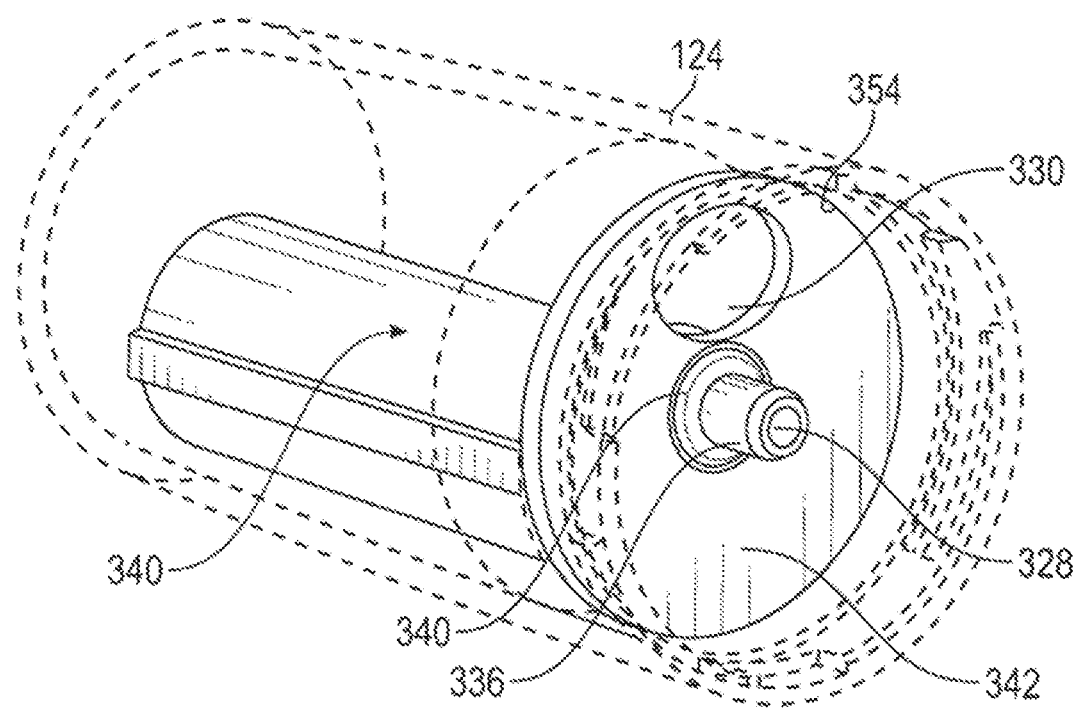
Figure 10E:
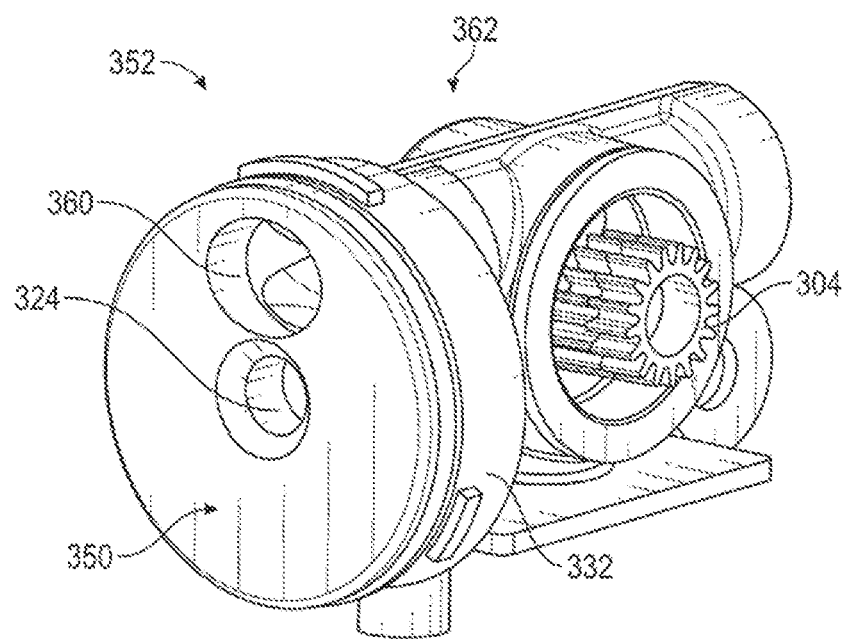

Referring to FIG. 10D, the filter assembly 120 additionally includes a filter base 342 through which filter line aperture 330 extends. The flow path 324 additionally extends through the filter base 342, and, in the illustrated implementation, exits the tubular projection 336 carrying the second vacuum aperture 328.

A complementary docking platform 350 is carried by the handpiece, having complementary connector to connector 134 for rapid attachment and detachment of the filter assembly 120 from the handpiece. In the illustrated embodiment, at least a first flange 352 may be received through an opening 354 on the filter assembly 120. Rotation of the filter assembly 120 moves the first flange into interference fit with a second flange 356 to secure the filter assembly 120 to the docking platform 350 on the handpiece. Two or three or four or more similar flange and complementary opening pairs may be provided around the periphery of the components. In the illustrated implementation, the circumferential arc length of the flange and corresponding opening on one of the three pairs is greater than the other two pairs to function as a key, so that the filter assembly can only be secured to the docking platform in a single rotational orientation.

The docking platform 350 includes a filter line aperture 360 for communicating with filter line 208, and a vacuum line aperture 362 for placing the filter 130 in communication with a source of vacuum. The docking platform 350 may be connected to a two way valve 362 or a three way valve as is discussed elsewhere herein depending upon the desired functionality. The valve may carry a rotatable drive gear 304 to rotate the interior rotatable valve gate as is discussed in additional detail below. Alternatively, a lever or other control on the housing may be configured to rotate a shaft directly coupled to the rotatable part of the valve.

A valved flow path may also be provided for venting the filter chamber 128 directly to atmosphere. The valve may be opened such as by depressing a momentary button, which is biased in the closed direction. This can create an abrupt change in pressure at the distal end of the catheter, which may facilitate clot aspiration. This can also be used to discharge vacuum.

Referring to FIG. 11A, additional details of the handle 140 of the second catheter 104 are disclosed. The handle 140 extends between a proximal end and a distal end. An elongate flexible tubular body 152 extends distally from the distal end of the handle 140 and is configured to advance distally through the proximal handle 106 and the tubular body 108 of thrombectomy catheter 102.

A steering dial 144 may be provided to place one or more steering wires under tension, to deflect a deflection zone near the distal end of the tubular body 152. A manifold switch 116 may be provided to control the flow of fluid as will be discussed below. The handle additionally comprises an aspiration control 117 such as a slider switch, for turning aspiration on or off. A max button 132 may be provided for delivering a momentary pulse of high aspiration rate as has been discussed.

Figure 12:
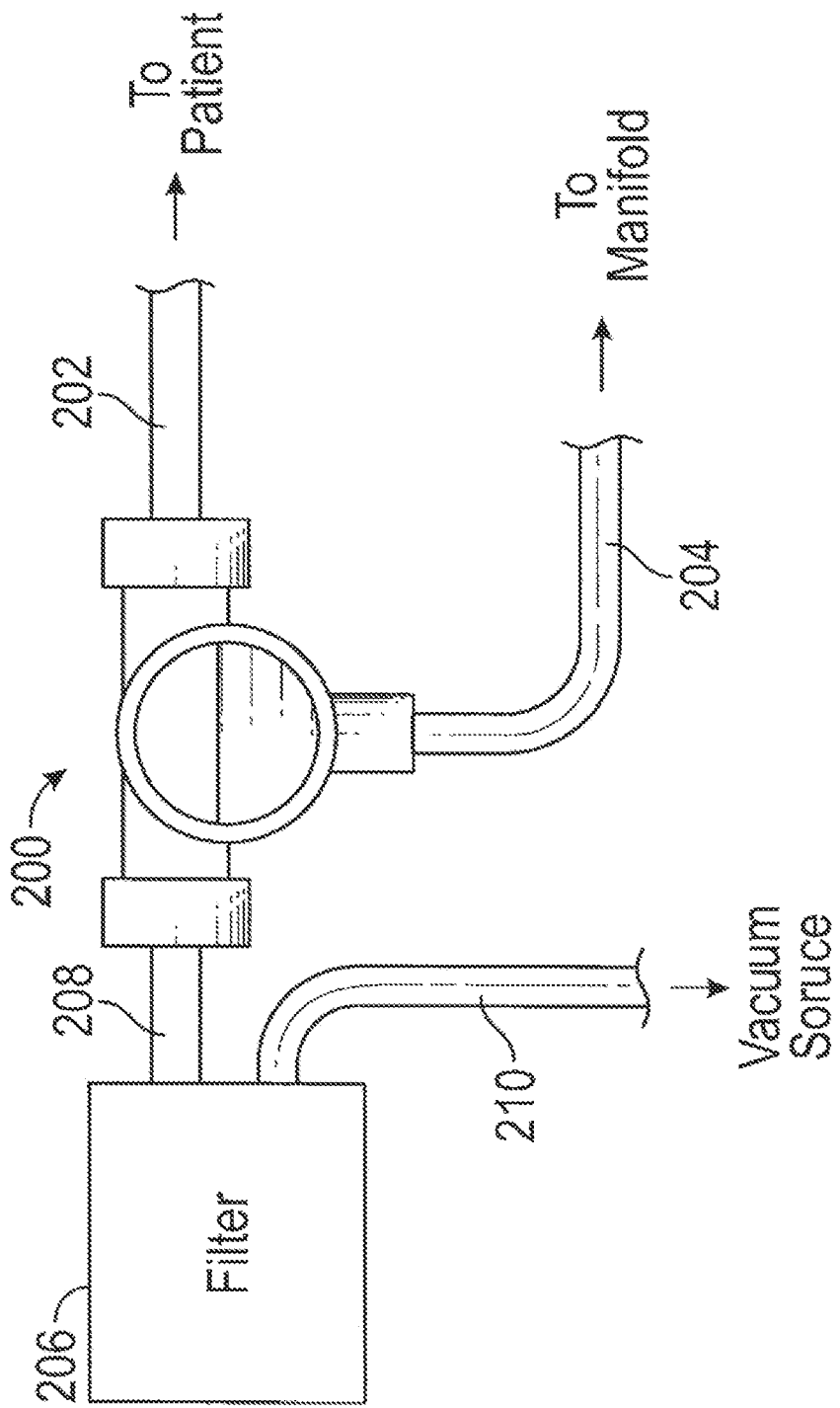
FIG. 12 is a schematic flow diagram for a three-way valve.

Fluid flow through the thrombectomy system is controlled by manifold switch 116 (see, e.g., FIG. 9), which may control a two way or three-way valve. Referring to FIG. 12, a schematic flow diagram for three-way valve 200 is provided. Patient line 202 can be placed in fluid communication with the patient, via a catheter such as a large diameter thrombectomy catheter 12 or second catheter 42.

Patient line 202 may be placed in communication with a manifold line 204 by advancing the three-way valve 200 to a first position, such as to allow delivery of medications, contrast media or saline to the patient.

Adjustment of the three-way valve 200 to a second position can isolate patient line 202 and place the manifold in communication with the filter 206 via filter line 208.

Activation of a vacuum pump will draw blood from the patient and through the filter 206 via vacuum line 210.

Further adjustment of the three-way valve 200 to a third position will place the manifold in communication with the vacuum line 210, such as to permit a saline flush of the filter 206. This third position may be eliminated depending upon the desired functionality.

Figure 13A:
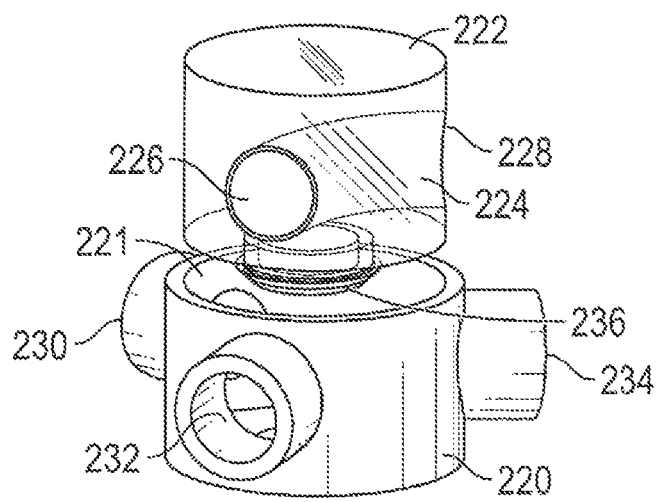
FIGS. 13A-13C illustrate three flow configurations for a three-way valve.
Figure 13B:
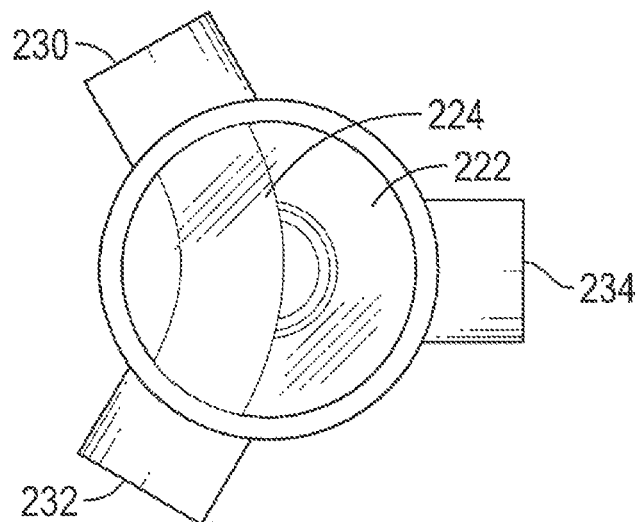
Figure 13C:
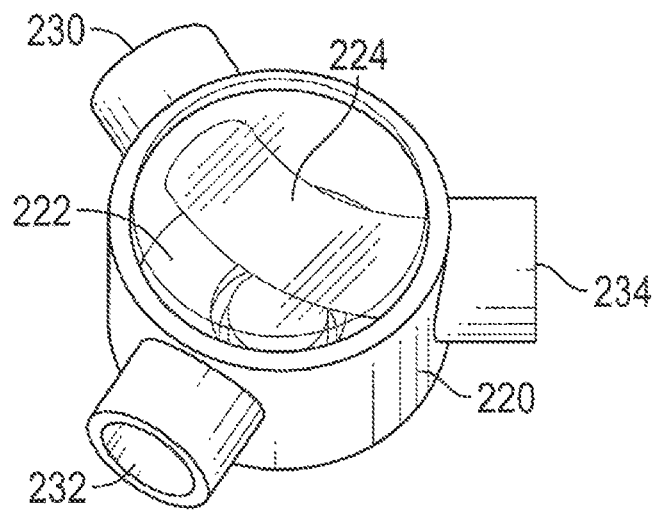

One implementation of a suitable three-way valve 200 is illustrated in FIGS. 13A through 13C. Referring to FIG. 13A, the valve 200 may comprise a housing 220 such as a cylindrical housing having a central cavity 221. A rotatable cylindrical gate 222 may be positioned in the central cavity 221, as illustrated in the exploded view of FIG. 13A. Rotatable gate 222 is provided with a flow path 224 extending between a first end 226 and a second end 228. In the illustrated implementation, the first end 226 and a second end 228 of the flow path are spaced apart around the circumference of the rotatable gate by approximately 120 degrees.

In the rotational orientation of the rotatable gate 222 illustrated in FIG. 13A, the first end 226 of the flow path 224 is in communication with a first port 232, and the second end 228 of the flow path 224 is in communication with a second port 234. This corresponds to the first position discussed previously, in which the patient is in fluid communication with the manifold.

FIG. 13B illustrates rotatable gate 222 in the second position where the flow path 224 places the first port 232 in communication with the third port 230 to place the filter 206 in communication with the manifold. The rotatable gate 222 may be toleranced within the cavity 221 such that the rotatable gate 222 seals the second port 234 thus isolating the patient from the flow path in this orientation. Similarly, in each of the other two orientations, two of the ports are placed in communication with the flow path, while the third port is isolated from the flow path.

The third position is illustrated in FIG. 13C, in which the flow path places the second port 234 in communication with the third port 230, placing the filter 206 in communication with the patient, and isolating the manifold from the flow circuit.

The foregoing selectivity may be achieved by spacing the three ports approximately 120 degrees apart around the circumference of the housing, to cooperate with the flow channel 224 end ports which are about 120 degrees apart around the circumference of the cylindrical gate 222. The gate 222 may be rotated within the housing 220 by a connector 236 extending through the housing 220 such as along the axis of rotation, and connected to a control 116 such as a rotatable knob, lever or slider switch with a rack and pinion drive assembly.

Each of the catheters disclose herein may be provided with a hemostasis valve on the proximal end, to allow selective closing of the central lumen to completely closed without any devices extending therethrough, from a sealed fit around devices of differing diameters such as a guide wire or a secondary catheter extending therethrough. One example of a suitable hemostasis valve is schematically illustrated in FIGS. 14A through 14C.

Figure 14A:
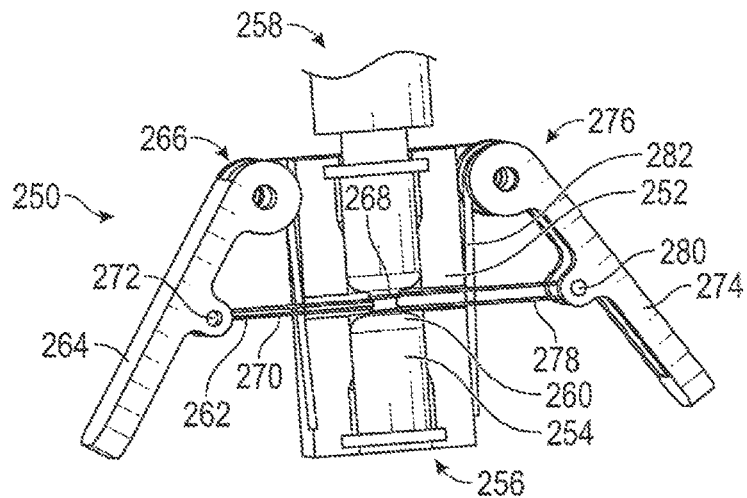
FIGS. 14A-14C illustrate operation of a hemostasis valve.
Figure 14B:
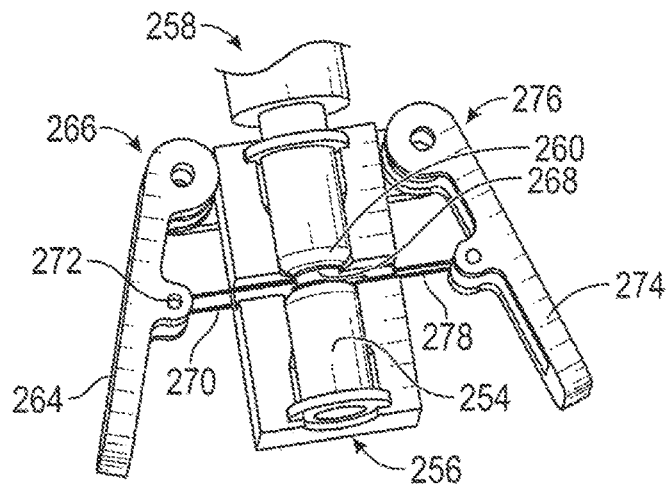
Figure 14C:
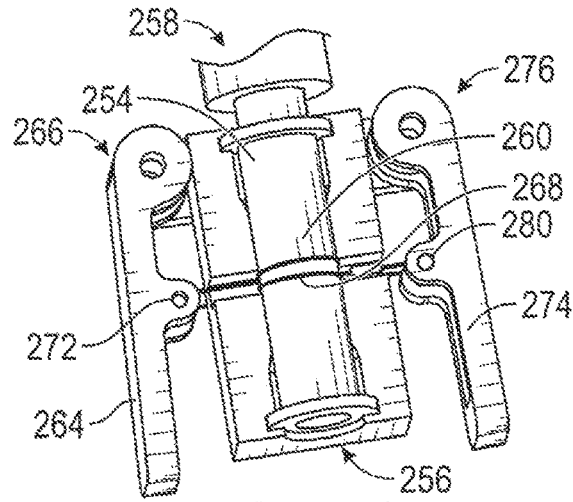

Referring to FIG. 14A, hemostasis valve 250 includes a frame 252 for supporting a flow path defined within a tubular sidewall 254. The frame 252 may be integrally formed with or mounted to the catheter handle or hub.

The flow path and tubular sidewall 254 extend between a first end 256 and a second end 258. First end 256 may be a port 112 (see, e.g., FIG. 9) on the proximal end of any of the catheters disclosed herein. Second end 258 may be in communication with the central lumen of the corresponding aspiration catheter, such that devices entering the first end 256 and advanced axially through the flow path can advance all the way to the distal end of the aspiration catheter and beyond.

At least a portion 260 of the sidewall 254 is collapsible in response to external pressure. That portion 260 and optionally the full length of the tubular sidewall within valve 250 may be comprise a collapsible elastic tube such as silicone tubing, which is biased into an open lumen tubular configuration when unconstrained. A compression element such as filament 262 is configured to apply compressive force against the sidewall 254 to reduce the inside diameter of the flow path to provide a seal against itself (when completely closed with no devices extending therethrough) or against a device such as a guidewire or catheter extending therethrough. In the illustrated implementation, the filament 262 forms a loop 268 around the collapsible portion 260 of tubular sidewall 254. Retraction of a first tail portion 270 of the filament 262 away from the sidewall 254 constricts the diameter of the loop 268 thereby collapsing the portion 260 of the tubular sidewall as illustrated in FIG. 14A.

In the illustrated implementation, the first tail portion 270 of the filament 262 may be retracted by at least a first lever 264. Lever 264 may be connected to the frame 252 by a first pivot 266 and is attached to the tail portion 270 at an attachment point 272. Advance of the lever in a first direction places the filament under tension and reduces the inside diameter of the valve. Releasing the lever removes the tension and the collapsible portion 260 of the sidewall rebounds to its unconstrained, open lumen configuration.

In the illustrated implementation, a second lever 274 is attached to the frame 252 at a second pivot 276, and is attached to a second tail portion 278 of the filament 262. Each of the first and second tail portions may comprise a single filament or two or three or more parallel filaments. In the two filament configuration as illustrated, the filaments may be immovably secured to the lever, or may be a continuous filament, looped around a fulcrum 280. The loop 268 may comprise one or two or three or more revolutions around the tubular sidewall, depending upon the desired performance.

At least one lever 264 is provided with a spring 282 to bias the lever away from the tubular sidewall, constricting the inside diameter of the collapsible portion 260 into sealing engagement with a device extending therethrough, or to a completely closed configuration in the absence of a device. As illustrated, a second lever 274 may also be biased using the same spring or a second spring.

As illustrated in FIG. 14C, compression of the levers in a medial direction towards the axis of the tubular sidewall 254 releases tension on the tail portions of the filament and allows the valve to open, such as to permit advance of a catheter through the valve. Releasing the levers allows the spring bias to retract the tail portions, reducing the diameter of the loop 268 and collapsing the collapsible portion 260 into sealing engagement with the outside surface of the secondary catheter, at an intermediate valve diameter as seen in FIG. 14B.

Retraction of the tail portion 270 of filament 262 may alternatively be accomplished by winding the tail portion 270 around a rotatable spool such as a shaft or drum. Rotation of a knob or advance of a lever causes the spool to take up filament and collapse the sidewall.

Figure 14D:
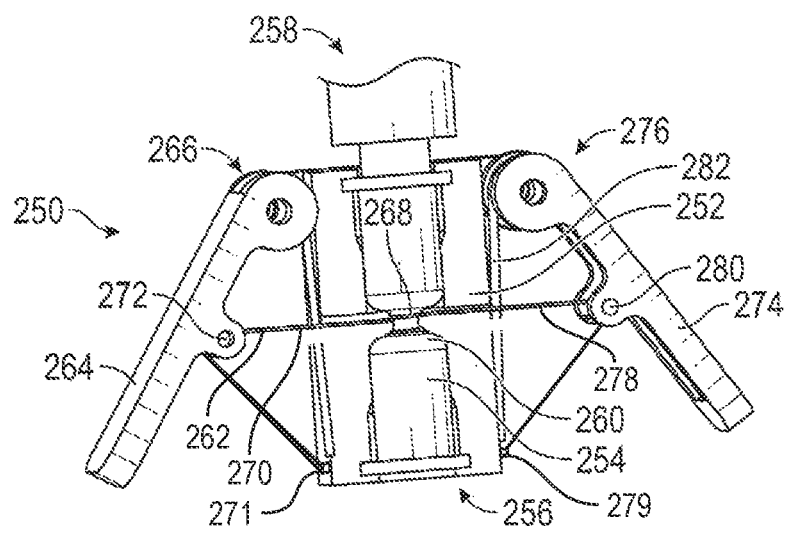
FIG. 14D illustrates an alternative filament configuration of the hemostasis valve.

An alternate configuration for the filament 262 is illustrated in FIG. 14D. In this implementation, the first tail portion 270 slidably extends around a first fulcrum at 272 and returns to attach to the housing at an attachment point 271. First tail portion 270 extends from the fulcrum to form a loop 268 around the collapsible tube. The filament 262 may make a single revolution or two or more revolutions around the collapsible tube before continuing on around a second fulcrum at 280, to a second point of attachment 279 to the housing.

Compression of the first lever 264 and second lever 274 loosens the loop 268, allowing the lumen to resume patency. Releasing the levers allows the spring bias to reduce the diameter of the loop 268 as the first tail portion 270 and second tail portion 278 slide away from each other around the left and right fulcrums. Preferably, friction between the filament 262 and fulcrums are minimized, as by providing a lubricious oil such as silicone oil around the fulcrums at 280 and 272, as well as using Teflon braided line for the filament 262.

Figure 15A:
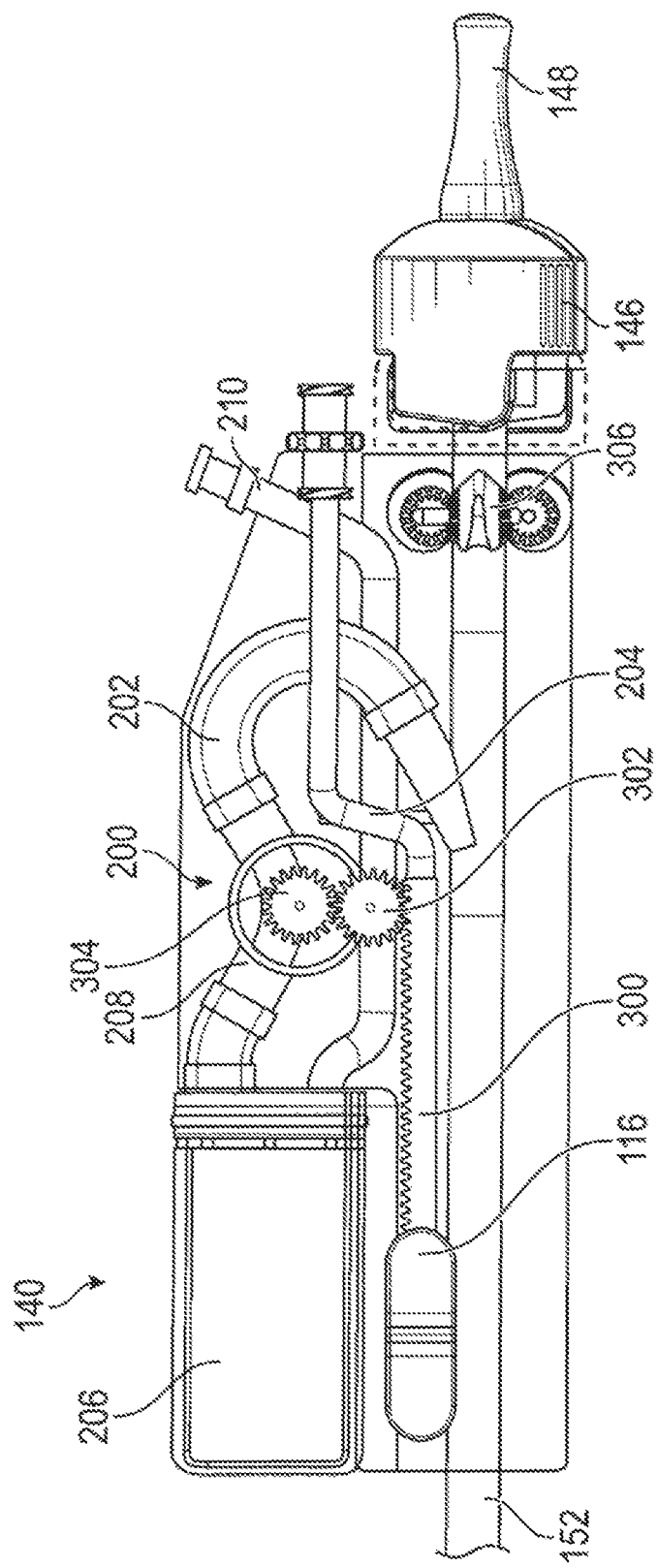
FIGS. 15A-15B are schematic layouts of the components of a proximal handle of an aspiration catheter.
Figure 15B:
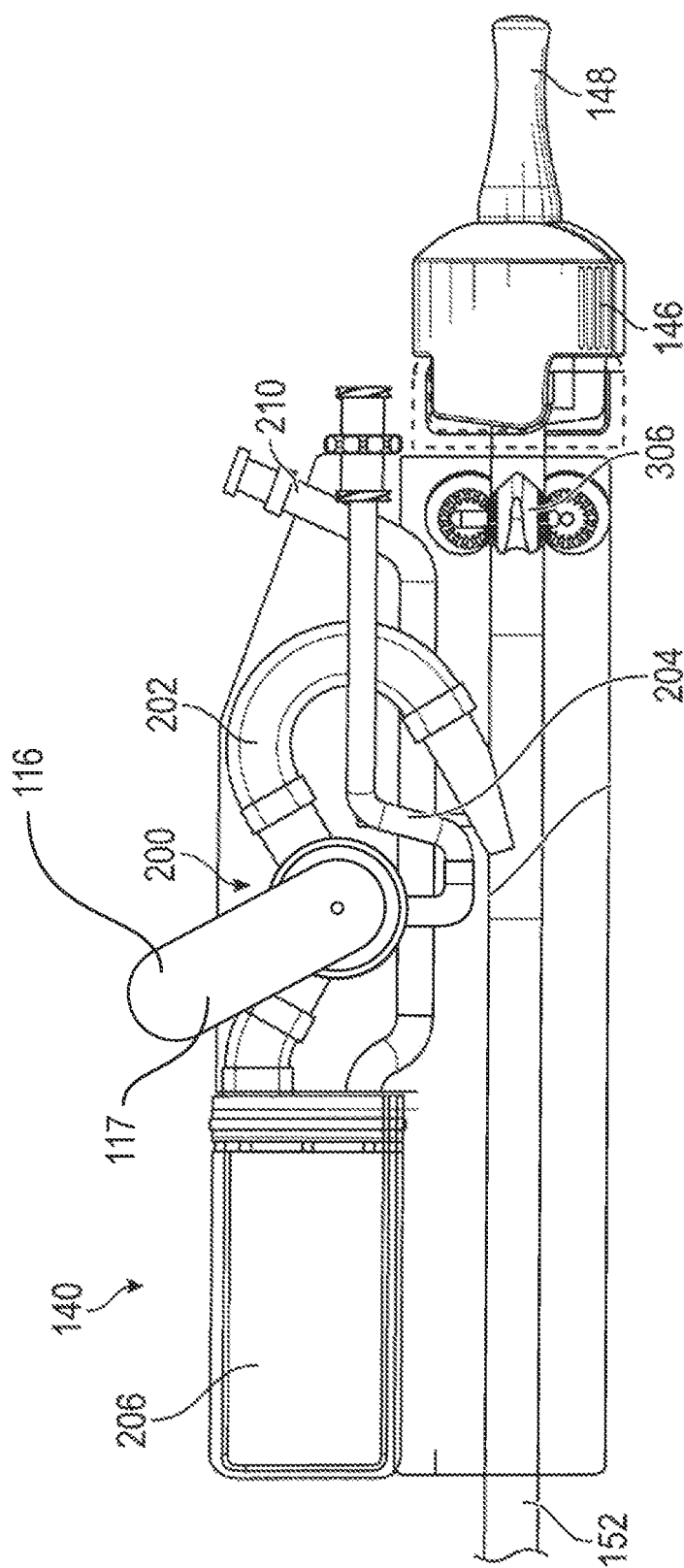

Various components of the aspiration system handle are schematically represented in context in FIG. 15A. The proximal handle 140 on a second catheter 104 includes a filter 206, a tubular body 152 and other features previously described. Two-way or three-way valve 200 selectively controls flow among the filter line 208, patient line 202 and manifold line 204. In this implementation, the three-way valve control 116 is in the form of the slider switch. The slider switch axially movably displaces a first linear rack gear 300. Rack gear 300 engages a pinion gear 302, which may either directly rotate the gate in the valve 200, or, as illustrated, drive a third gear 304 which rotates the rotatable gate within 200. An alternative valve control system is schematically illustrated in FIG. 15B. In this implementation, the slider switch, linear rack gear 300 and pinion gear 302 omitted. A valve control 116 in the form of a lever 117 is attached directly to a shaft which controls rotation of the valve gate. The lever may be advanced proximally or distally, to adjust the flow path through the valve as has been discussed.

A steering mechanism 306 is provided to permit steering of the second catheter 152. Manually rotatable knob 148 allows manual rotation of a core wire and distal helical tip as has been discussed. The core wire axially movably extends across hemostasis valve 146. Alternatively, the core wire and tip (e.g., thrombus engagement tool 400) may be coupled to a motorized drive unit at the proximal end of the catheter system.

In certain implementations of the invention, an aspiration catheter such as a 16 French catheter is advanced transvascularly over a wire and/or through a larger diameter (e.g., 24 French aspiration catheter) to the treatment site. If the application of vacuum is not able to aspirate the clot into the 16 French catheter, an elongate flexible thrombus engagement tool may be advanced through the 16 French aspiration catheter, to facilitate retrieval of the clot.

Figure 16A:
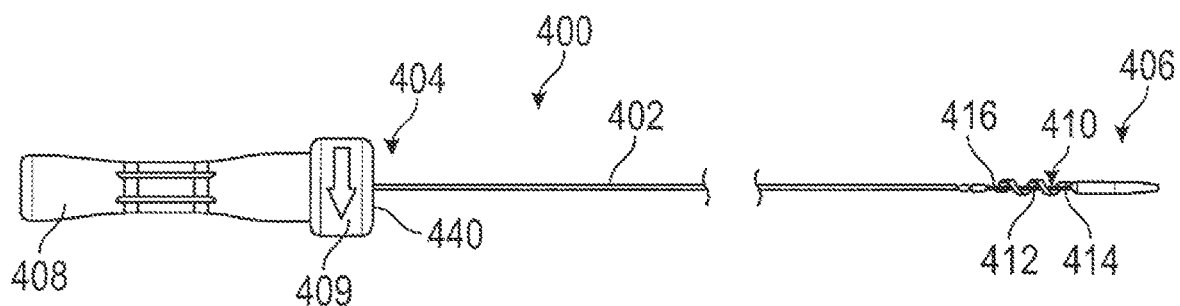
FIGS. 16A and 16B are different implementations of thrombus engagement tools.
Figure 16B:
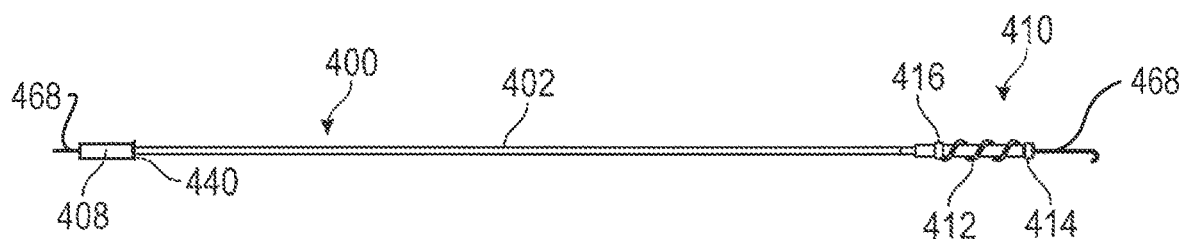

Referring to FIGS. 16A and 16B, the thrombus engagement tool 400 may comprise an elongate flexible shaft 402 having a proximal end 404 and a distal end 406. A proximal hand piece such as a handle 408 may be configured to be rotated by hand. Distal end 406 carries a clot engagement tip 410 which may include one or more radially outwardly extending structures such as a helical thread 412. The handle 408 may have an indicium of rotational direction such as a printed or molded arrow 109 which indicates the direction to rotate the handle 408 in order for the helical thread 412 to engage clot.

Figure 18A:
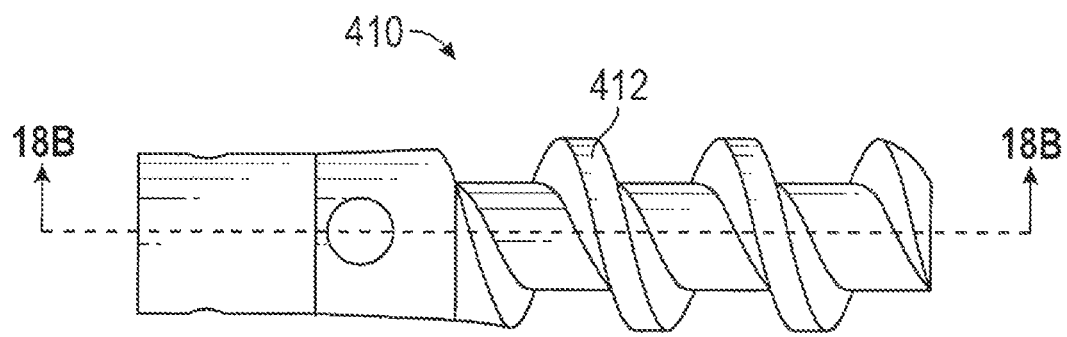
FIG. 18A is a side elevational view of an alternative thrombus engagement tip.
Figure 18B:
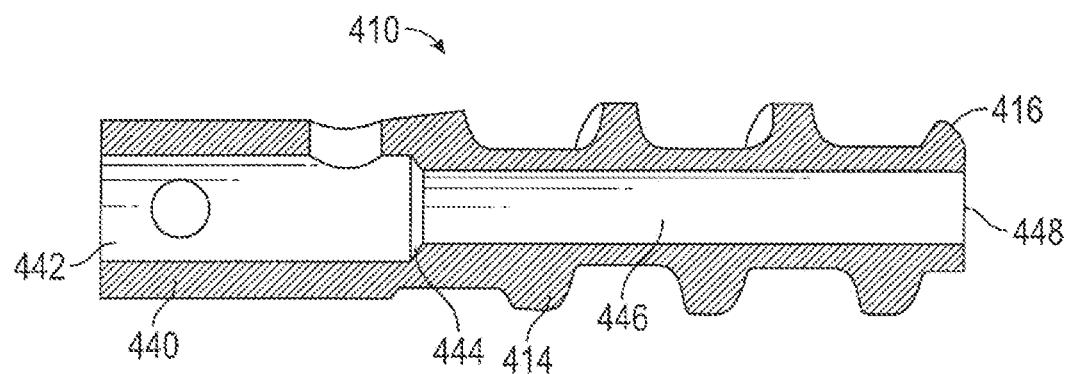
FIG. 18B is a longitudinal cross-section through the tip of FIG. 18A.

In one implementation illustrated in FIG. 16B, the thrombus engagement tool 400 carries a clot engagement tip 410 of the type illustrated in FIGS. 18A and 18B. The proximal end of the tip 410 is glued to the distal end of a braid-reinforced polyimide tube. The proximal end of the Microlumen has a cannulated torquing handle 408, and the whole assembly is cannulated so it can be delivered and function over a wire 468 such as an 0.035" wire. The 0.035" wire helps maintain space between the tip and the vessel wall, and the wire can be pulled back inside the working length of the flexible shaft 402 during rotation and engagement with the clot as needed.

Figure 17A:
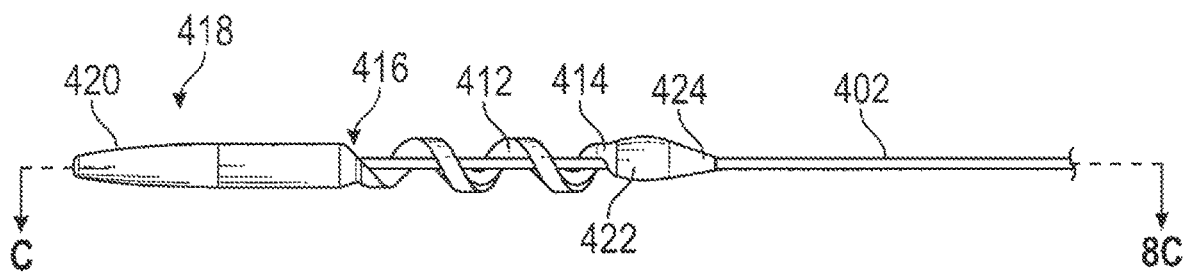
FIG. 17A is a side elevational view of one thrombus engagement tool tip.

Referring to FIG. 17A, the distal tip 410 includes a helical thread 412 extending from a distal end 414 to a proximal end 416 and supported by flexible shaft 402. The axial length of the distal tip 410 is at least about 2 mm or 5 mm or 10 mm and in some embodiments no more than about 30 mm or 20 mm measured along the flexible shaft 402. The helical thread 412 wraps around the axis at least about 1 or 2 or 4 or more full revolutions, but in some embodiments no more than about 10 or 6 revolutions. In some embodiments the axial length along the threaded portion of the tip is within the range of from about 1 to about 8 revolutions.

The helical thread 412 on this implementation may have a constant pitch throughout its length. The pitch may be within the range of from about 10 to about 20 threads per inch, or about 5 to about 10 threads per inch depending upon desired performance. Alternatively, the thread may have multiple pitches designed to engage, transport and grasp thrombus within the catheter lumen. A distal pitch may be less than a proximal pitch. The pitch may vary continuously along the length of the thread, or may step from a first, constant pitch in a proximal zone to a second, different pitch in a distal zone of the thread. The thread 412 may comprise a continuous single helical flange, or may have a plurality of discontinuities to produce a plurality of teeth or serrations, arranged helically around the core wire.

The side elevational profile or envelope scribed by the distal tip as it rotates may have a linear or nonlinear taper on one or both ends (e.g., football shaped) which provide varying diameter and thus clearance along its length from the generally cylindrical ID of the catheter lumen.

The maximum OD of the thread 412 is preferably smaller than the diameter of a sliding fit within the catheter lumen, and may generally be at least about 0.015 inches or 0.010 inches smaller than the catheter lumen ID. In some implementations, the Max OD of the tip may be significantly less than the inside diameter of the catheter lumen to allow more space for the thrombus, but still create significant grasping force via engagement of the helical threads with the thrombus. In one implementation, the maximum helical thread diameter is about 0.110 inches and the catheter lumen ID is about 0.275 inches (24F) (a 0.165 inch gap between the helical threads and catheter wall).

In certain applications, the Max OD of the tip is no more than about 35% or no more than about 40% or no more than about 60% of the ID of the catheter, to leave a substantial tip bypass flow path. Since this implementation does not have any centering structures for the tip 410 or shaft 402, the tip will normally be pushed to one side of the aspiration lumen. When a clot becomes lodged between the tip and the opposing wall of the catheter, manual rotation of the tip can engage the clot like a worm gear and either grasp the clot (e.g., by pinning it against the opposing catheter sidewall) for retraction or facilitate freeing the blockage and aid in ingestion of the clot into the catheter.

The profile of the tip 410 viewed along the axis of rotation may be circular, or may vary to create a non circular pattern around the axis of rotation. The tip as seen in an end elevational view thus exhibits a major diameter and a minor diameter. The minor diameter may be no more than about 95% or 90% or 80% or 70% of the major diameter, depending upon desired performance.

Figure 17B:
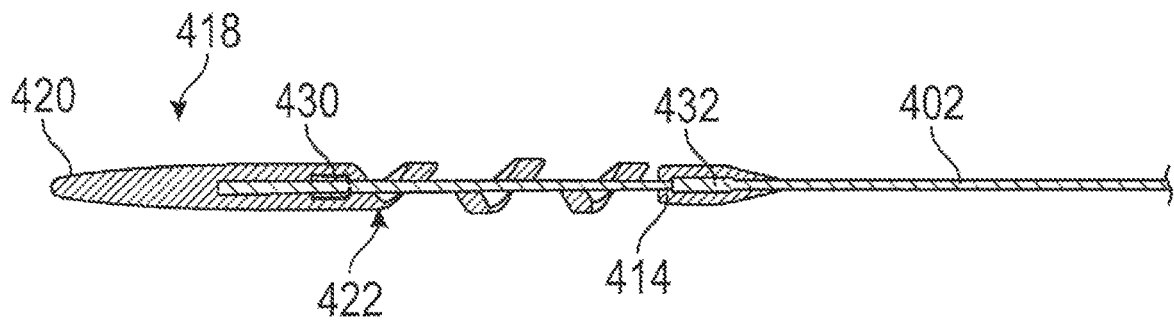
FIG. 17B is a longitudinal cross-section through the tip of FIG. 17A.

Referring to FIGS. 17A and 17B, the illustrated tip 410 includes a distal advance segment 418 extending between an atraumatic distal tip at 420 and a transition to the distal end 416 of the thread 412. Helical thread 412 extends proximally from the transition to a proximal end 414 of the helical thread 412. A trailing segment 422 extends between the proximal end 414 of the thread and the proximal end 424 of the tip.

The axial length of the advance segment 418 may be at least about 1 cm or 2 cm and in some implementations is within the range of from about 2 cm to about 4 cm. The axial length of the helical thread 412 along the longitudinal axis is typically within the range of from about 1 cm to about 5 cm and in certain implementations between about 2 cm and 3 cm.

The outside diameter of the advance segment 418 at distal tip 420 is generally less than about 0.024 inches, or less than about 0.020 inches and, in one implementation, is about 0.018 inches. The maximum outside diameter of the advance segment 418 and helical thread 412 may be within the range from about 0.020 to about 0.045 inches, and, in one implementation, is less than about 0.040 inches, such as about 0.035 inches. The advance segment, helical thread and trailing segment of the tip 410 may be molded over the flexible shaft 402 using any of a variety of polymers known in the catheter arts.

Referring to FIG. 17B, a first radiopaque marker 430 may be carried on the flexible shaft 402 beneath the advance segment 418. A second radiopaque marker 432 may be carried on the flexible shaft 402 within the trailing segment 422. Each radiopaque marker may comprise a radiopaque tube or a coil of radiopaque wire such as a platinum iridium alloy wire having a diameter about 0.002 inches, and wrapped around the flexible shaft 402 and soldered to the flexible shaft 402 to produce an RO coil having an outside coil diameter of less than about 0.020 inches, such as about 0.012 inches. The radiopaque markers may also function as an axial interference fit between the flexible shaft 402 and the molded advance segment 418 and trailing segment 422 to resist core wire pull out from the tip 410.

In one implementation, the maximum OD of the thread 412 exceeds the maximum OD of the advance segment 418 by at least about 15% or 25% or 30% or more of the OD of the advance segment 418, to facilitate crossing the clot with the advance segment 418 and engaging the clot with the thread 412. The thread pitch may be within the range of from about 0.75 to about 0.30, or within the range of from about 0.10 and about 0.20, such as about 0.14 inches.

Preferably, the maximum OD of the tip 410 is less than about 60% or less than about 40% of the aspiration catheter ID at the distal end of the catheter, and may be within the range of from about 35% to about 55% of the catheter ID. In certain implementations, the maximum OD of the tip 410 may be within the range of from about 0.044 inches to about 0.041 inches within a catheter having a distal end ID within the range from about 0.068 inches to about 0.073 inches.

Depending upon the clinical application, it may be desirable to control the extent to which, if any, the distal tip 410 can extend beyond the distal end of the catheter. For example, distal extension of the distal end of the helical tip beyond the distal end of the catheter may be limited in some implementations to no more than about 5 mm or 3 mm or 1.5 mm or 1.0 mm or less. In other clinical environments the distal tip 420 may be permitted to extend at least about 2 cm or 3 cm and preferably as much as 4 to 8 cm beyond the catheter, but generally will be limited to extend no more than a preset distance such as 12 cm or 8 cm or 5 cm beyond the catheter depending upon desired performance. In one implementation, distal advance of the tip 410 is limited so that the distal end is within 2 cm or within 1 cm or no more than 0.5 cm in either the distal or proximal direction from the distal end of the aspiration catheter.

Distal advance of the tip 420 may be limited by providing mechanical interference at the desired distal limit of travel. In one implementation, a distal stop surface 440 on the handle 408 provides an interference engagement with a complementary proximal surface carried by the aspiration catheter through which the thrombus engagement tool 400 is advanced. Alternatively, a distal engagement surface can be carried anywhere along the length of the thrombus engagement tool 400, for sliding engagement with a complementary proximally facing stop surface carried by the catheter. Additional details may be found in U.S. patent application Ser. No. 17/036,258 filed Sep. 29, 2020 and entitled Embolic Retrieval Catheter, which is hereby expressly incorporated in its entirety herein by reference.

The limit on distal advance of the helical tip may include a first configuration in which distal advance is limited to a first position proximate the distal end of the evacuation catheter to prevent injury to the vascular wall. Upon a user initiated adjustment, the helical tip may be advanced to a second position farther out of the distal end of the catheter such as for inspection and cleaning purposes. This adjustment of the limiting mechanism may be locked out following cleaning or inspection, to limit distal travel to the first position to prevent an undesired degree of exposure of the helical tip element when the system is within the patient's vasculature. Any of a variety of movable interference levers of pins may be engaged to limit travel to the first position, or disengaged to allow travel to the second position.

Referring to FIGS. 18A and 18B, a tip 410 includes a tubular sidewall 440 defining a hub having a connector such as a cavity 442 for coaxially receiving the distal end of a support shaft such as a braid reinforced polyamide tube. The inside diameter of the cavity 442 steps down at a distal end of the hub at a step 444 to a smaller diameter lumen 446 in communication with a distal opening 448. This provides a continuous lumen throughout the length of the micro lumen shaft and tip 410 so that the thrombus engagement tool can be introduced over the wire.

In general, the pitch of thread 412 may be within the range of from about 0.07 to about 0.11, and in one embodiment, is about 0.09. The width of the thread 412 measured along an axis that is perpendicular to a face of the thread may be within the range of from about 0.009 to about 0.04, and, in one embodiment, is about 0.02. The greatest major diameter of the thread 412 may be at least about 10%, or at least about 15%, or at least about 20% greater than the diameter of the proximal hub end of the tip 410 surrounding the cavity 442. In one implementation, the outside diameter of the proximal hub is about 0.090 inches and the outside diameter of the thread 412 is about 0.110 inches. The actual length of the tip 410 including the proximal hub may be within the range of from about 0.2 inches to about 0.8 inches and in some implementations within the range of from about 0.4 inches to about 0.6 inches.

The tip 410 may be manufactured in accordance with any of a variety of techniques known in the art, such as machining, etching, additive and/or subtractive processes. In one implementation, the tip 410 is molded from a polymer such as PEBAX, which may be a 55 D hardness. The PEBAX may include a radiopaque agent, such as bismuth sub carbonate, present in the range of from about 50% to about 70% by weight.

Any of the tip dimensions and configurations disclosed herein may be re-combined with any of the other tip dimensions, configurations, drive shafts and associated structures depending upon the desired clinical performance.

Referring to FIGS. 19A-19D, there is illustrated a split dilator system 450 which may be utilized with any of the catheters disclosed herein. The system includes a catheter 452 having an elongated tubular body 454 extending between a proximal end 456 and a distal end 458. Proximal end 456 is provided with a proximal hub or manifold 457 as has been discussed in connection with other catheters disclosed herein.

An elongate flexible dilator 460 has a length sufficient to extend throughout the entire length of the catheter 452. Dilator 460 extends between a proximal end 462 and a distal end 464 having a tapered distal tip 466. The dilator 460 is provided with a central lumen (not illustrated) so that it may be advanced over a guide wire 468. Proximal end 462 of the dilator is provided with a proximal hub 470.

A split 472 extends the length of the hub 470 and along the sidewall of the tubular dilator 460. The split may be in the form of a slot extending through the entire wall thickness of the dilator, a perforation line, a groove, or other weakening to allow the formation of a slit through the dilator side wall, and through which the guide wire 468 may be laterally removed as discussed further below. The longitudinal split 472 may extend the entire length of the dilator 460, or extend from the proximal end in a distal direction to an endpoint 473 within the range of from at least about 2 cm or 5 cm to no more than about 40 cm or 30 cm from the tapered tip 466.

Preferably, a first locking component carried by the hub 470 is releasably engageable with a complementary second locking component carried by the hub 457.

Figure 19A:
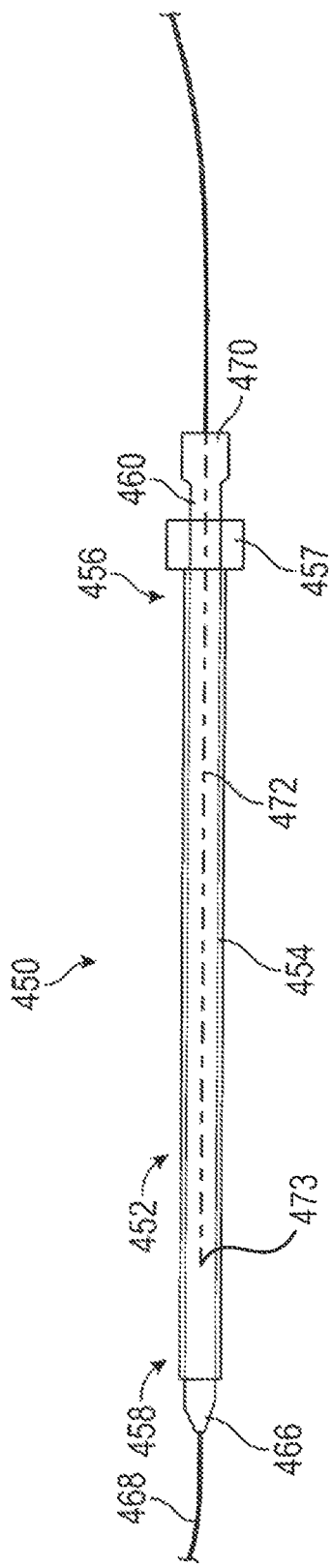
FIG. 19A is a side elevational view of a catheter and split dilator system in accordance with the present invention.
Figure 19B:
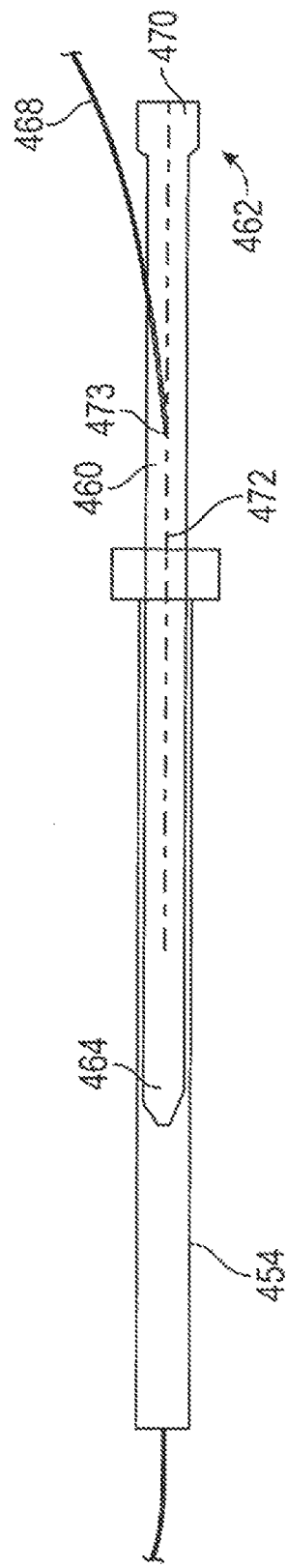
FIG. 19B shows the system of FIG. 19A, with the dilator partially retracted and peeled away from the guide wire with the guide wire progressively escaping from the dilator through an axially extending split.
Figure 19C:
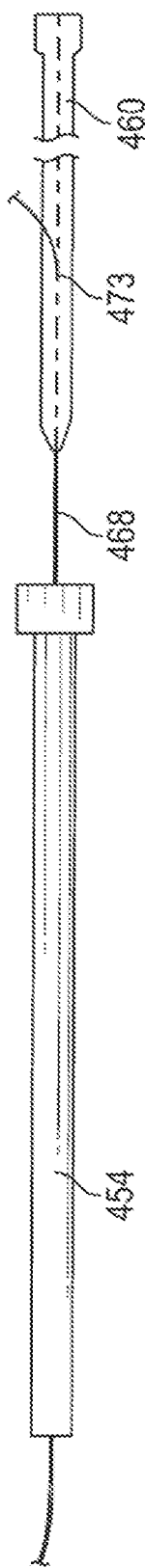
FIG. 19C shows the dilator fully retracted from the catheter but still over the guide wire.
Figure 19D:
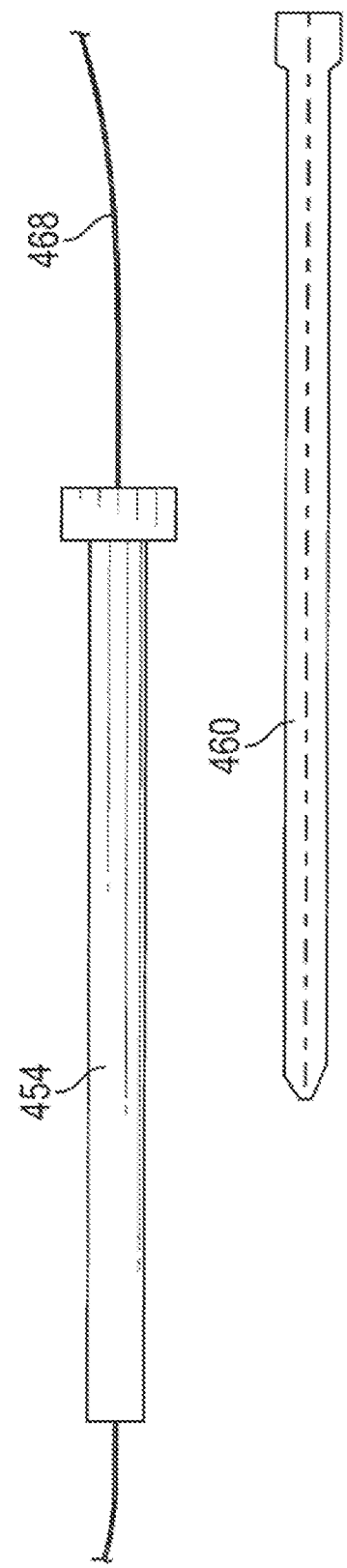
FIG. 19D shows the dilator fully removed from the catheter and the guide wire, leaving the catheter and guide wire unmoved from their position within the vasculature.

Referring to FIG. 19B, following trans vascular advance of the catheter and dilator assembly to the desired intravascular location, the dilator 460 may be proximally removed leaving the catheter 452 in place. Desirably, the guide wire 468 may remain unmoved in position at the target vascular site while removing the dilator 460, preferably without the need for a proximal guide wire extension. For this purpose, the guide wire 460 may be laterally progressively removed from the dilator at a parting point 473 that advances axially along the split 472, as the dilator 460 is proximally retracted from the catheter 452 and guidewire 468.

Once the tapered tip 466 has been proximally retracted from the catheter, the guide wire 468 may be grasped between the dilator 460 and the catheter 462, and the dilator 460 may be proximally removed from the catheter 452 and from the guide wire 468. This allows removal of the dilator without disturbing the position of the catheter or the guide wire, which are thereafter available for a subsequent intravascular procedure.

Figure 20A:
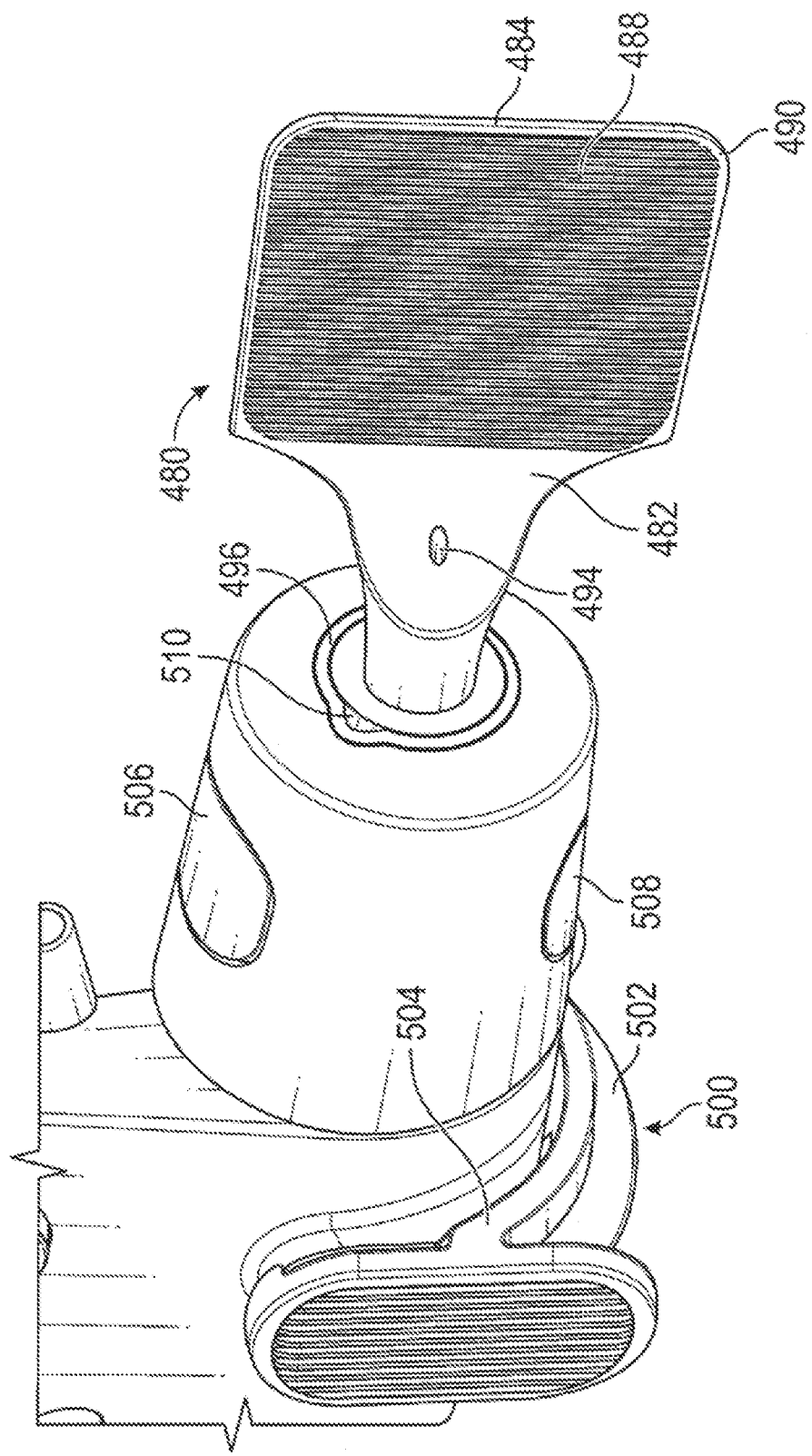
FIGS. 20A-20C show a proximal handle for a dilator.
Figure 20B:
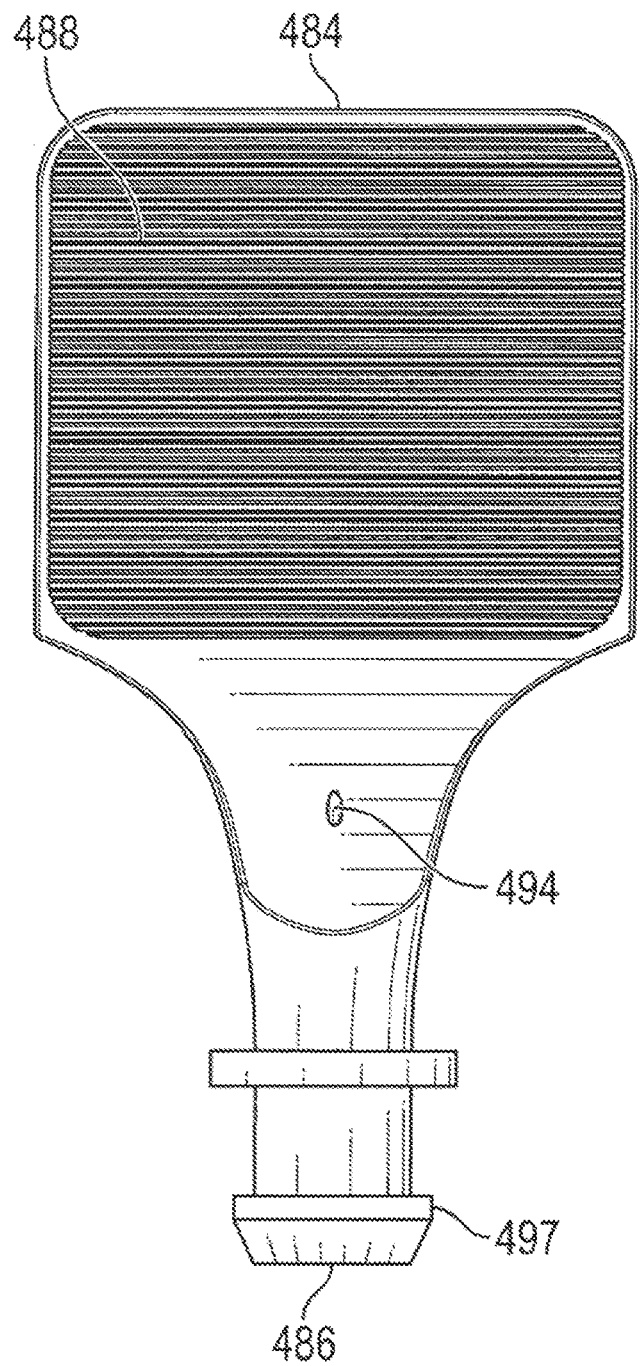
Figure 20C:
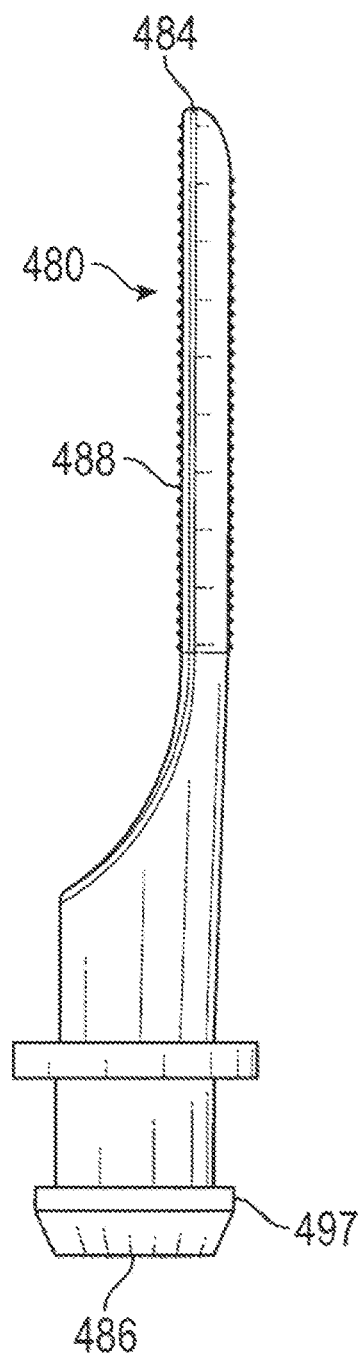

Referring to FIGS. 20A and 20B, there is illustrated a proximal dilator handle 480. The handle 480 comprises a body 482 having a proximal end 484 a distal end 486 and a longitudinal axis. At least a first proximal gripping surface 488 is carried by the body. In the illustrated implementation, a first gripping surface 488 is provided on at least one side of a paddle shaped grip 490, configured to be held between a thumb and forefinger. A second gripping surface 492 may be provided on an opposing side of the handle. Gripping surfaces may be provided with a friction enhancing surface structures such as a plurality of ridges oriented transverse to the longitudinal axis of the dilator handle 480.

A proximal exit port 494 in communication with the dilator guidewire lumen is oriented along the longitudinal axis of the dilator handle 480, such that a guide wire extending out of the exit port 494 lies along the first gripping surface 488. This allows a clinician to pin the guide wire to the gripping surface 488 using a finger such as a thumb, thereby enabling the dilator and the guide wire to be moved as a unit using one hand.

The dilator may be removably secured to the catheter such as by a retention clip 496 carried by the proximal end of the handle. A release such as a button or deformable interference snap fit may be provided to unlock the dilator handle from the housing, enabling the dilator to be proximally withdrawn from the catheter. In the illustrated implementation, a retention surface such as a proximal surface of a retention ring 497 carried by proximal end 486 of the body 482 provides an interference fit with the retention clip 496. This combines the dilator and handle/catheter into a single system. The paddle may be released from the retention clip by depressing at least a first button 506 and as illustrated also a second button 508 carried on the upper and lower sides of the retention clip housing, and proximally withdrawing the paddle.

This is the same connection and release dock for use with a thrombus engagement tool such as engagement tool 400 discussed in connection with FIGS. 16A and 16B. A distal limit safety feature on the thrombus engagement tool 400 fits into the retention clip 496, ensuring that the distal tip of the tool 400 can not be advanced forward beyond the distal tip of the catheter without both aligning a projection on the tool 400 with the rotational key 502 and intentionally advancing the tool 400 through the retention clip while depressing at least the first button 506 or other unlock control.

Once the distal limit has been released, the tip 410 may be distally advanced no more than about 4 cm and generally about 1 cm to 2 cm beyond the distal end of the catheter. This is intended to be accomplished once the thrombus engagement tool has been withdrawn from the patient, to allow visual inspection of the tip 410.

The engagement tool 400 may also be proximally retracted within the catheter, typically for less than about 3 cm or less than about 2 cm, and may be provided with a spring bias to return to approximate axial alignment between the distal end of the tip 410 and the distal end of the catheter.

A hemostasis clamp 500 may be provided, to hold the hemostasis valve open such as during shipping, or during the advance or withdrawal of devices therethrough. The hemostasis valve is opened by depressing at least a first control button, and in the illustrated implementation first and second control buttons positioned on opposing sides of the handle. The hemostasis clamp comprises a generally U shaped body 502 having a first arm 504 configured to depress a first button, and a second opposing arm (not illustrated) configured to depress a second button on an opposite side of the handle. The hemostasis clamp 500 may be removably retained on the handle by a friction fit, or an interference fit between the handle and the body which can be overcome by plastic deformation as the body is pulled away from the handle to release the hemostasis control buttons.

Figure 21:
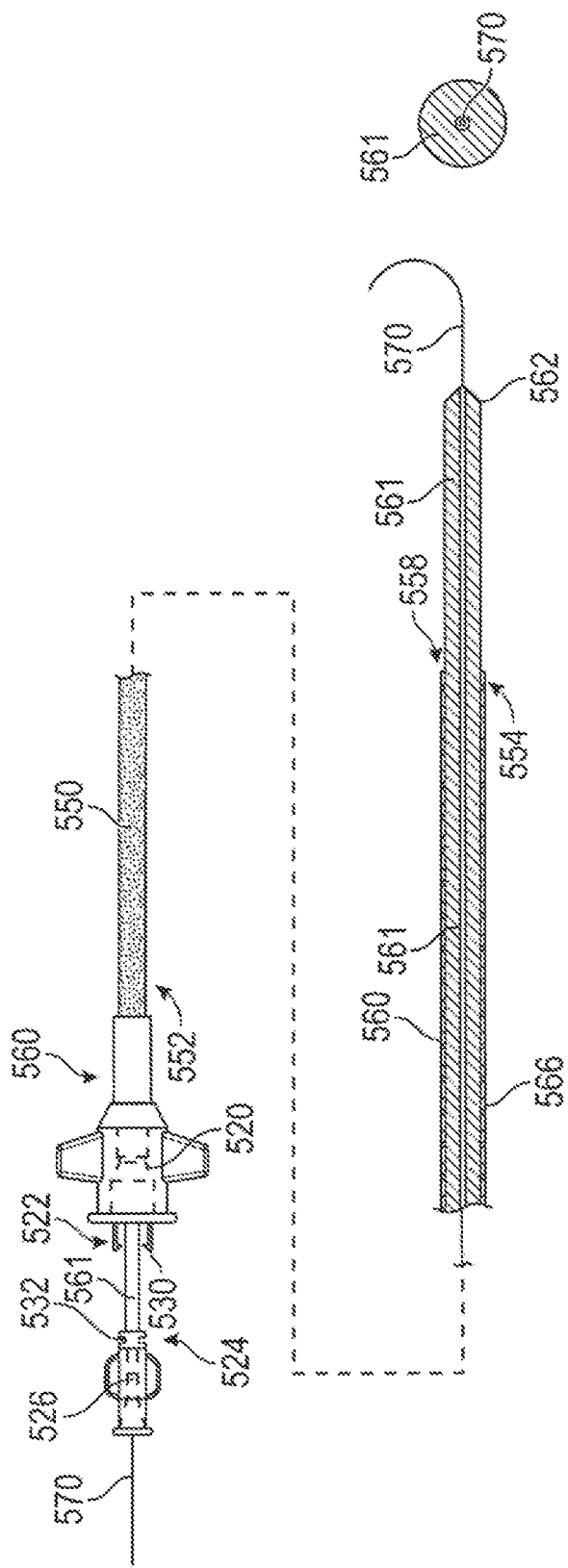
FIG. 21 is a side elevational partial cross section of a catheter having a cannulated guide rail extending therethrough over a guidewire.

Referring to FIG. 21, an elongate flexible cannulated rail or dilator 561 is shown extending over the guidewire 570 and occupying the space between the guidewire 570 and the large inside diameter of the central lumen 558 of the large diameter catheter 560 to provide support to the catheter and/or an atraumatic tip during delivery.

This catheter-cannulated rail-guidewire assembly is intended to easily track through anatomical challenges more easily than the catheter. The catheter-rail-guidewire assembly then acts as a first stage of the catheter delivery system and enables the large diameter catheter or catheter system to be inserted and independently advanced over this first stage into a blood vessel (e.g., the femoral vein) percutaneously over a guidewire and advanced through potentially tortuous vasculature to the remote target location of interest without requiring advanced skills or causing kinking of the catheter.

The cannulated rail 561 may comprise a soft flexible cylindrical body having a guidewire lumen with a diameter of no more than about 0.040" and an outside diameter no less than about 0.025" or about 0.010" smaller than the inner diameter of the large diameter catheter. Thus the wall thickness of the cannulated rail 561 is typically at least about 0.010" less than the radius of the large diameter catheter and in some implementations at least about 0.120" or more, depending upon the size of the annular space between the inside diameter of the catheter and the outside diameter of the guidewire.

The cannulated rail 561 may have an elongated tapered distal tip 562 that may project beyond the distal end 554 of the catheter 560. The thick sidewall of the cannulated rail 561 may comprise one or more flexible polymers, and may have one or more embedded column strength enhancing features such as axially extending wires, metal or polymeric woven or braided sleeve or a metal tube, depending upon the desired pushability and tracking performance along the length of the dilator.

Optionally, the proximal segment of the rail or dilator which is not intended to extend out of the distal end of the catheter may be a structure which is not coaxial with the guidewire, but a control wire which extends alongside the guidewire in the catheter and allows the distal tubular telescoping segment of the rail or dilator to be retracted or extended. (analogous to rapid exchange catheters) without the entire length of the rail structure being over the wire. This allows removal or insertion of the rail or dilator over a shorter guidewire because of the shorter coaxial segment tracking over the guidewire.

Catheter 560 may be provided with a proximal hub 520, having a port for axially movably receiving the rail 561 therethrough. The hub 520 may be provided with an engagement structure such as a first connector 522 for releasably engaging a second complementary connector 524 on a hub 526 on the proximal end of the rail 561. First connector 522 may comprise an interference structure such as at least one radially moveable projection 530, for releasably engaging a complementary engagement structure such as a recess 532 (e.g., an annular ridge or groove) on the hub 526. Distal advance of the rail 561 into the catheter 560 causes the projection 530 to snap fit into the recess 532, axially locking the catheter 560 and rail 561 together so that they may be manipulated as a unit.

The dilator is inserted through the hemostasis valve in the hub 520 of a large bore (e.g., 24F) catheter 560 and advanced through the catheter until the retention clip on the dilator hub 526 or catheter hub 520 snaps into the complementary recess on the other hub. In this engaged configuration, an advance segment along the flexible distal end of the 24F rail dilator 561 will extend at least about 5 cm or 10 cm, and in some implementations at least about 15 cm or 20 cm beyond the distal end 554 of the 24F catheter 560. The rail dilator and 24F catheter system are thereafter distally advanced over a previously placed guidewire and into the introducer sheath.

The dilator and catheter combination of the present invention differentiate over prior systems both because of the flexibility of a distal zone of the dilator and greater length of the dilator than the corresponding catheter. Typically, a dilator is a uniform stiffness and length-matched to its catheter, with only a short atraumatic tip of the dilator extending beyond the distal end of the catheter. The dilator of the present invention has a supportive proximal end and a flexible distal end, with a total dilator length much longer than the catheter 60 to enable, as an example, the following procedure.

In use, a guidewire 570 such as an 0.035" guidewire is advanced under fluoroscopy using conventional techniques into a selected vessel. The cannulated rail 561, optionally with the catheter 560 mounted thereon, is loaded over the proximal end of the guidewire 570 and advanced distally over the wire until the distal end of the rail is in position at the target site.

The 24F catheter 560 is thereafter unlocked from the rail 561 and advanced over the rail 561 to the desired site, supported by the rail 561 and guidewire 570 combination. Because the uncovered advance section of the rail has already traversed the challenging tortuosity through the heart, the catheter 561 now just slides over the advance section of the rail for easy passage to the final target location. The supportive proximal zone and flexible distal advance section of the rail enables ease of delivery through the most challenging anatomy in, for example, a PE procedure going from the vena cava through the tricuspid and pulmonary valves of the heart into the central pulmonary artery without concern about damaging the tissue (atraumatic, flexible tip) or damaging the dilator (high kink resistance due to flexible, high wall thickness "solid" dilator construction.

The cannulated rail 561, or the cannulated rail 561 and the guidewire 570 combination, may thereafter be proximally withdrawn, leaving the large bore catheter 560 in position to direct a procedure catheter such as any of the aspiration catheters disclosed elsewhere herein to the target site.

Figure 22:
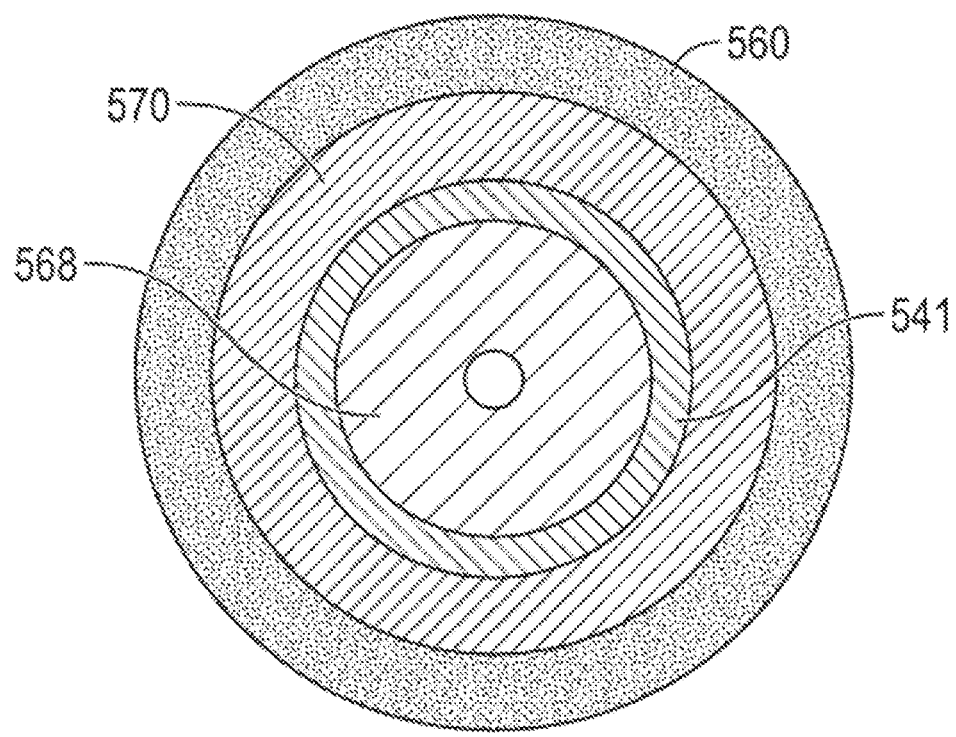
FIG. 22 is a cross sectional view through a dual dilator system such as that shown in FIG. 23.
Figure 23:
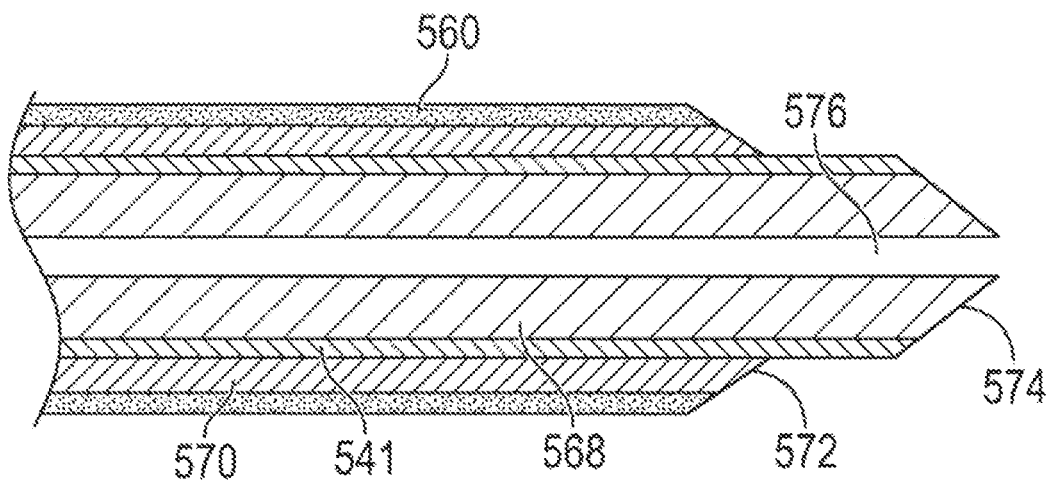
FIG. 23 is a side elevational cross section of a distal portion of a dual dilator system of the present invention.

Referring to FIG. 22, the large diameter (LD) catheter 560 may in some situations have a smaller diameter (SD) catheter though its central lumen for the purposes of introducing an additional functionality (e.g., clot grabber catheter 562, imaging catheter 10, or mechanical thrombectomy tool 66) and/or telescoping the SD catheter to more distal locations in the anatomy. In order to enable delivery of the LD catheter 560 and SD catheter as a single system, the SD catheter may have a core dilator 568 for support, and the gap between the outer diameter of the SD catheter and inner diameter of the LD catheter 560 may be maintained or supported by a second, tubular dilator 571. The tubular dilator 571 may have a shaped distal tip 572 for a smooth tapered transition from the SD catheter 541 to the LD catheter 540. The distal end 534 of the core dilator may be provided with a complementary taper to the distal taper of the thin wall SD dilator (FIG. 23) or may end at the distal end of the LD catheter (FIG. 24).

The core dilator 568 inside the SD catheter 541 and tubular dilator 570 between the two catheters may have an interlocking feature to create a single (SD+LD) catheter+(core+tubular) dilator system. For example, complementary connectors may be provided on hubs on the proximal ends of the system components.

Figure 24:
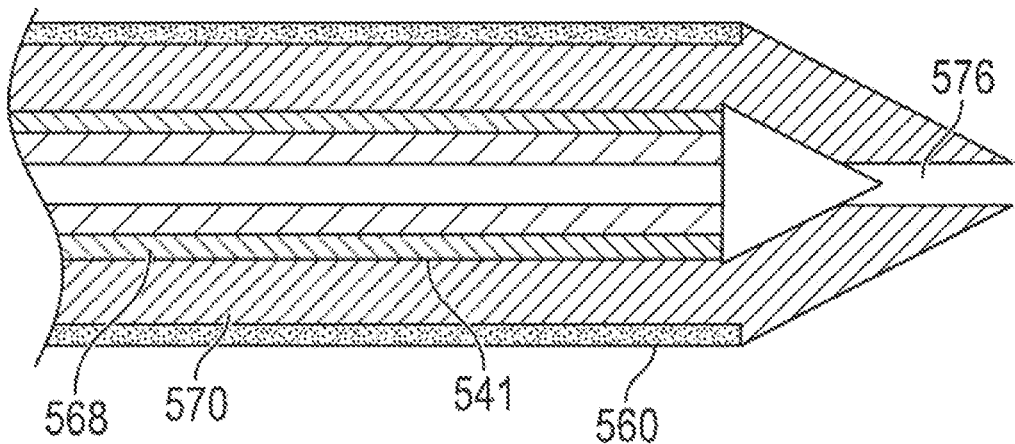
FIG. 24 is a cross section as in FIG. 23, with a distal tip formed by the tubular dilator.

Referring to FIG. 24, the tip of the tubular dilator 570 may be configured to taper to the guidewire lumen 576, thus covering and extending distally beyond the small diameter catheter 541 if it is in place. The tip of the tubular dilator 570 may be provided with a longitudinally extending slit 578, scored or perforated one or more times to allow the tip to split longitudinally and be pulled back into the space between the LD and SD catheters and fully expose the distal end of the small diameter catheter 541. See FIG. 25.

Figure 25:
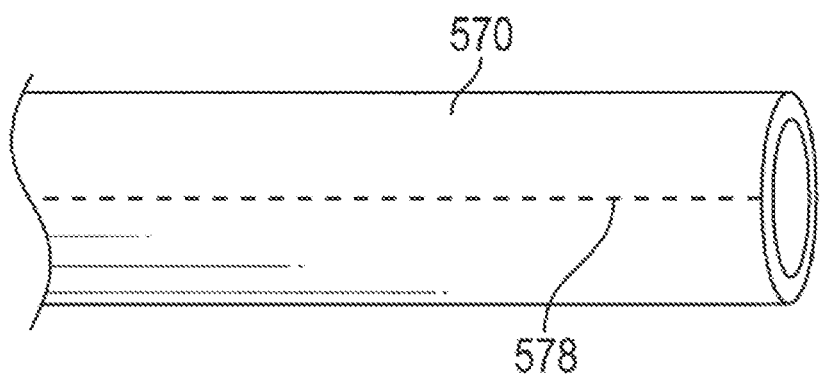
FIG. 25 is a side elevational view of a portion of a tubular dilator having a separation line to allow longitudinal splitting of the sidewall during proximal retraction.

The single (SD+LD) catheter+(core+tubular) dilator system may be pre-assembled and detachably interlocked at the proximal hub. Additional tubular dilators having a series of outside diameters and wall thicknesses may be provided such that the SD catheter may be used in combination with different diameter LD catheters. A LD catheter may be used with different SD catheters by providing tubular dilators having the same OD but a series of different inside diameters. The core+tubular dilators may simply be pulled proximally to withdraw both dilators as a single system, or the tubular dilator may be configured with a tab or handle at the proximal end and a slit, scoring, perforation or other mechanism so as to split, peel, or tear it along the longitudinal axis during withdrawal to allow the tubular dilator to peel from the SD catheter as it slides proximally out of the space between the LD and SD catheters. (FIG. 25).

Example Embodiments

An aspiration system with accelerated response, comprising one or more of the following:

an aspiration pump in communication with a first chamber;

an aspiration catheter configured for placement into fluid communication with the first chamber by way of an aspiration tube;

a second chamber in between the aspiration tube and the catheter; and a valve between the second chamber and the aspiration catheter;

wherein upon opening of the valve with negative pressure in the first and second chambers, resistance to fluid flow between the second chamber and the distal end of the catheter is less than the resistance to fluid flow between the second chamber and the first chamber, causing a rapid aspiration into the second chamber.

An aspiration system as described in any embodiment herein, further comprising a handle on the aspiration catheter, and the second chamber is carried by the handle.

An aspiration system as described in any embodiment herein, further comprising a first control on the handle for opening the valve.

An aspiration system as described in any embodiment herein, wherein the valve is normally closed and actuation of the control momentarily opens the valve.

An aspiration system as described in any embodiment herein, further comprising a second control for activating the pump.

An aspiration system as described in any embodiment herein, further comprising a hemostasis valve carried by the handle.

An aspiration system as described in any embodiment herein, wherein the hemostasis valve comprises a collapsible tubular sidewall defining a valve lumen, and a filament formed into a loop around the tubular sidewall and configured to collapse the valve lumen.

An aspiration system as described in any embodiment herein, wherein the hemostasis valve further comprises a frame and a lever, and the filament has at least a first tail portion extending away from the loop, around a first fulcrum on the lever and is secured against axial movement with respect to the frame.

An aspiration system as described in any embodiment herein, wherein the first tail portion is connected to the frame.

An aspiration system as described in any embodiment herein, further comprising a second lever, and the filament further comprises a second tail portion extending from the loop, around a second fulcrum on the second lever and is connected to the frame.

An aspiration system as described in any embodiment herein, wherein the aspiration tube is at least about 50 inches long.

An aspiration system as described in any embodiment herein, wherein the second chamber is configured to capture clot aspirated by the catheter.

An aspiration system as described in any embodiment herein, wherein at least a portion of the second chamber is removably carried by the handle.

An aspiration system as described in any embodiment herein, wherein the second chamber comprises a filter membrane spaced apart from a transparent wall.

An aspiration system as described in any embodiment herein, comprising a tubular filter membrane, spaced radially inwardly apart from a transparent outer tubular wall.

An aspiration system as described in any embodiment herein, further comprising an operator actuated control, configured to toggle a flow regulator between a default low flow mode, and a momentary, operator initiated high flow override mode.

An aspiration system as described in any embodiment herein, wherein the second chamber is configured for location within a sterile field, and the first chamber is configured for location outside of the sterile field.

An aspiration system as described in any embodiment herein, further comprising a handle on the aspiration catheter, a tube between the handle and the second chamber, and the tube is no more than about 20 inches long.

A split dilator aspiration system, comprising one or more of the following:

a catheter, having an elongate, flexible tubular body with a proximal end, a distal end, a side wall defining a central lumen, and a handle on the proximal end; and a dilator, advanceable through the central lumen, the dilator having an elongate body, cannulated to receive a guidewire, and an axially extending split along at least a portion of the elongate body, configured to allow removal of a portion of the dilator laterally from the guidewire.

A split dilator aspiration system as described in any embodiment herein, wherein the handle comprises a first engagement surface, and the dilator has a proximal hub with a second engagement surface configured to engage the first engagement surface to releasably secure the dilator within the catheter.

A split dilator aspiration system as described in any embodiment herein, comprising a retention clip carried by the proximal end of the catheter handle.

A split dilator aspiration system as described in any embodiment herein, further comprising a retention surface carried by the grip body.

A split dilator aspiration system as described in any embodiment herein, wherein the retention surface is on a retention ring configured to engage the retention clip.

A split dilator aspiration system as described in any embodiment herein, further comprising a release control, for disengaging the grip body from the catheter handle.

A split dilator aspiration system as described in any embodiment herein, wherein the release control comprises at least one push button.

A split dilator aspiration system as described in any embodiment herein, further comprising a clot container on the handle.

A split dilator aspiration system as described in any embodiment herein, further comprising a hemostasis valve on the handle.

A split dilator aspiration system as described in any embodiment herein, wherein the split comprises a weakening in the wall to permit the progressive formation of a slit through the wall to allow lateral escape of the guidewire.

A split dilator aspiration system as described in any embodiment herein, wherein the split comprises a pre formed slit completely through the wall.

A split dilator aspiration system as described in any embodiment herein, wherein the split extends to a distal endpoint spaced proximally apart from the distal end of the catheter.

A split dilator aspiration system as described in any embodiment herein, wherein the distal endpoint is spaced proximally apart within the range of from about 5 cm to about 40 cm from the distal end of the catheter.

A split dilator aspiration system as described in any embodiment herein, further comprising a proximal handle on the dilator.

A split dilator aspiration system as described in any embodiment herein, wherein the handle comprises a grip body having a first gripping surface and a guidewire exit port configured to direct a guidewire along the first gripping surface.

A split dilator aspiration system as described in any embodiment herein, wherein the body comprises a paddle shape with the first gripping surface on a first side and configured to be held between a thumb and forefinger such that a guidewire can be pinned between the thumb and the first gripping surface.

A split dilator aspiration system as described in any embodiment herein, further comprising friction enhancing surface structures on the first gripping surface.

A split dilator aspiration system as described in any embodiment herein, wherein the friction enhancing surface structures comprise a plurality of ridges.

A hemostasis valve, comprising one or more of the following:
  a support;
  at least a first lever, pivotably carried with respect to the support;
  a collapsible tubular sidewall defining a valve lumen carried by the support;
  a filament formed into a loop around the tubular sidewall, the filament having at least a first tail portion extending away from the loop to the first lever; and
  a first spring configured to move the first lever in a direction that pulls the first tail portion away from the tubular sidewall, reducing the diameter of the valve lumen in response to reducing the diameter of the loop.

A hemostasis valve as described in any embodiment herein, further comprising a second lever pivotably carried with respect to the support.

A hemostasis valve as described in any embodiment herein, further comprising a second tail portion extending away from the loop and to the second lever.

A hemostasis valve as described in any embodiment herein, wherein the first tail portion, second tail portion and loop are one continuous filament.

A hemostasis valve as described in any embodiment herein, further comprising a lubricious coating on the filament.

A hemostasis valve as described in any embodiment herein, wherein the lubricious coating comprises silicone oil.

A hemostasis valve as described in any embodiment herein, wherein the first and second levers are biased in a direction that places the first and second tail portions under sufficient tension to reduce the diameter of the valve lumen and provide a seal around a device extending through the valve.

A hemostasis valve as described in any embodiment herein, wherein the first and second levers are biased in a direction that places the first and second tail portions under sufficient tension to close the valve.

A hemostasis valve as described in any embodiment herein, wherein the first tail portion is attached to the first lever.

A hemostasis valve as described in any embodiment herein, wherein the first tail portion slidably extends around a first fulcrum on the first lever, and is attached to the frame.

A hemostasis valve as described in any embodiment herein, wherein the second tail portion slidably extends around a second fulcrum on the second lever, and is attached to the frame.

A hemostasis valve as described in any embodiment herein, wherein the first and second fulcrums comprise pins.

A hemostasis valve as described in any embodiment herein, mounted on the proximal end of a catheter.

A hemostasis valve as described in any embodiment herein, further comprising a connector in communication with the valve lumen, configured for connection to a source of vacuum.

A vacuum aspiration system, comprising:
  a housing;
  a fluid flow path extending through the housing;
  a first catheter in fluid communication with the flow path and a connector configured to place a source of aspiration in communication with the flow path;
  a clot container carried by the housing; and
  a hemostasis valve in the housing, configured to receive a second catheter and direct the second catheter through the first catheter.

A vacuum aspiration system as described in any embodiment herein, further comprising a flow regulator, configured to regulate fluid flow through the flow path.

A vacuum aspiration system as described in any embodiment herein, wherein at least a portion of the clot container is removably carried by the housing.

A vacuum aspiration system as described in any embodiment herein, wherein the clot container comprises a filter membrane spaced apart from a transparent wall.

A vacuum aspiration system as described in any embodiment herein, comprising a tubular filter membrane, spaced radially inwardly apart from a transparent outer tubular wall.

A vacuum aspiration system as described in any embodiment herein, further comprising an operator actuated control, configured to toggle the flow regulator between a default low flow mode, and a momentary, operator initiated high flow override mode.

A vacuum aspiration system as described in any embodiment herein, wherein the operator actuated control comprises a momentary control that places the system into the high flow override mode only when actuated by the operator.

A vacuum aspiration system as described in any embodiment herein, further comprising an on-off control which toggles between an off mode and the low flow mode.

A vacuum aspiration system as described in any embodiment herein, further comprising a side wall containing the flow path, and an optically transparent window in the side wall.

A vacuum aspiration system as described in any embodiment herein, wherein the flow regulator comprises a variable constriction in the flow path.

A vacuum aspiration system as described in any embodiment herein, wherein the flow regulator comprises a flexible flow path side wall and an actuator configured to compress the flexible side wall.

A vacuum aspiration system as described in any embodiment herein, comprising a flexible filament surrounding the side wall and at least one lever configured to place the filament under tension and close the valve by reducing the diameter of the side wall.

A vacuum aspiration system as described in any embodiment herein, further comprising at least one spring, biasing the lever in a direction that closes the valve.

A vacuum aspiration system as described in any embodiment herein, wherein the flow regulator comprises a tubing having an inside diameter and length to provide a desired flow rate.

A vacuum aspiration system as described in any embodiment herein, wherein the low flow mode aspirates fluid at a rate of no more than about 10 cc/second and the high flow mode aspirates fluid at a rate of at least about 15 cc/second in an unobstructed aspiration.

A vacuum aspiration system, comprising:
a housing;
a fluid flow path extending through the housing;
a first catheter in fluid communication with the flow path and a connector configured to place a source of aspiration in communication with the flow path;
a flow regulator, configured to regulate fluid flow through the flow path;
a first operator actuated control, configured to toggle the flow regulator between a default, low flow mode, and a momentary, operator initiated high flow override mode; and
a second operator actuated control, configured to turn the fluid flow off.

A vacuum aspiration system as described in any embodiment herein, further comprising a port on the housing, in communication with the first connector and configured to guide a second catheter through the housing and into and through the first catheter.

A vacuum aspiration system as described in any embodiment herein, further comprising a hemostasis valve carried by the housing, in communication with the port.

A vacuum aspiration system as described in any embodiment herein, further comprising a reservoir carried by the housing, for receiving thrombus and blood retrieved through the first catheter.

A vacuum aspiration system as described in any embodiment herein, wherein the reservoir comprises a transparent tubular wall releasably carried by the housing.

What is claimed is:

1. A split dilator aspiration system, comprising:
a catheter, having an elongate, flexible tubular body with
   a proximal end, a distal end, a side wall defining a central lumen, and a handle on the proximal end;
a dilator advanceable through the central lumen, the dilator having:
   an elongate body cannulated to receive a guidewire, and
   an axially extending split along at least a portion of the elongate body, the split configured to allow removal of a portion of the dilator laterally from the guidewire; and
a clot container on the handle.

2. A split dilator system as in claim 1, wherein the handle comprises a first engagement surface, and the dilator has a proximal hub with a second engagement surface configured to engage the first engagement surface to releasably secure the dilator within the catheter.

3. A split dilator system as in claim 2, comprising a retention clip carried by the proximal end of the catheter handle.

4. A split dilator system as in claim 3, further comprising a retention surface carried by the proximal hub of the dilator.

5. A split dilator system as in claim 4, wherein the retention surface is on a retention ring configured to engage the retention clip.

6. A split dilator system as in claim 4, further comprising a release control, for disengaging the proximal hub of the dilator from the catheter handle.

7. A split dilator system as in claim 6, wherein the release control comprises at least one push button.

8. A split dilator system as in claim 1, further comprising a hemostasis valve on the handle.

9. A split dilator system as in claim 1, wherein the split comprises a weakening in a wall of the elongate body to permit the progressive formation of a slit through the wall to allow lateral escape of the guidewire.

10. A split dilator system as in claim 1, wherein the split comprises a pre formed slit completely through the wall.

11. A split dilator system as in claim 1, wherein the split extends to a distal endpoint spaced proximally apart from the distal end of the catheter.

12. A split dilator system as in claim 11, wherein the distal endpoint is spaced proximally apart within the range of from about 5 cm to about 40 cm from the distal end of the catheter.

13. A split dilator system as in claim 1, further comprising a proximal handle on the dilator.

14. A split dilator system as in claim 13, wherein the handle comprises a grip body having a first gripping surface and a guidewire exit port configured to direct a guidewire along the first gripping surface.

15. A split dilator system as in claim 14, wherein the grip body comprises a paddle shape with the first gripping surface on a first side and configured to be held between a thumb and forefinger such that a guidewire can be pinned between the thumb and the first gripping surface.

16. A split dilator system as in claim 15, further comprising friction enhancing surface structures on the first gripping surface.

17. A split dilator system as in claim 16, wherein the friction enhancing surface structures comprise a plurality of ridges.

18. A split dilator system, comprising:
a catheter, having an elongate, flexible tubular body with
   a proximal end, a distal end, a side wall defining a central lumen, and a handle on the proximal end; and
a dilator advanceable through the central lumen, the dilator having:
   an elongate body cannulated to receive a guidewire, and
   an axially extending split along at least a portion of the elongate body, the split configured to allow removal of a portion of the dilator laterally from the guidewire,
wherein the split extends to a distal endpoint spaced proximally apart from the distal end of the catheter.

19. A split dilator system as in claim 18, wherein the handle comprises a first engagement surface, and the dilator has a proximal hub with a second engagement surface configured to engage the first engagement surface to releasably secure the dilator within the catheter.

20. A split dilator system as in claim 19, comprising a retention clip carried by the proximal end of the catheter handle.

21. A split dilator system as in claim 20, further comprising a retention surface carried by the proximal hub of the dilator.

22. A split dilator system as in claim 21, wherein the retention surface is on a retention ring configured to engage the retention clip.

23. A split dilator system as in claim 21, further comprising a release control, for disengaging the proximal hub of the dilator from the catheter handle.

24. A split dilator system as in claim 23, wherein the release control comprises at least one push button.

25. A split dilator system as in claim 18, further comprising a hemostasis valve on the handle.

26. A split dilator system as in claim 18, wherein the split comprises a weakening in a wall of the elongate body to permit the progressive formation of a slit through the wall to allow lateral escape of the guidewire.

27. A split dilator system as in claim 18, wherein the split comprises a pre formed slit completely through the wall.

28. A split dilator system as in claim 18, wherein the distal endpoint is spaced proximally apart within the range of from about 5 cm to about 40 cm from the distal end of the catheter.

29. A split dilator system as in claim 18, further comprising a proximal handle on the dilator.

30. A split dilator system as in claim 29, wherein the handle comprises a grip body having a first gripping surface and a guidewire exit port configured to direct a guidewire along the first gripping surface.

31. A split dilator system as in claim 30, wherein the grip body comprises a paddle shape with the first gripping surface on a first side and configured to be held between a thumb and forefinger such that a guidewire can be pinned between the thumb and the first gripping surface.

32. A split dilator system as in claim 31, further comprising friction enhancing surface structures on the first gripping surface.

33. A split dilator system as in claim 32, wherein the friction enhancing surface structures comprise a plurality of ridges.

34. A split dilator system, comprising:
  a catheter, having an elongate, flexible tubular body with a proximal end, a distal end, a side wall defining a central lumen, and a handle on the proximal end;
  a dilator advanceable through the central lumen, the dilator having:
    an elongate body cannulated to receive a guidewire, and
    an axially extending split along at least a portion of the elongate body, the split configured to allow removal of a portion of the dilator laterally from the guidewire; and
  a proximal handle on the dilator, the handle comprising a grip body having a first gripping surface and a guidewire exit port configured to direct a guidewire along the first gripping surface.

35. A split dilator system as in claim 34, wherein the handle comprises a first engagement surface, and the dilator has a proximal hub with a second engagement surface configured to engage the first engagement surface to releasably secure the dilator within the catheter.

36. A split dilator system as in claim 35, comprising a retention clip carried by the proximal end of the catheter handle.

37. A split dilator system as in claim 36, further comprising a retention surface carried by the proximal hub of the dilator.

38. A split dilator system as in claim 37, wherein the retention surface is on a retention ring configured to engage the retention clip.

39. A split dilator system as in claim 37, further comprising a release control, for disengaging the proximal hub of the dilator from the catheter handle.

40. A split dilator system as in claim 39, wherein the release control comprises at least one push button.

41. A split dilator system as in claim 34, further comprising a hemostasis valve on the handle.

42. A split dilator system as in claim 34, wherein the split comprises a weakening in a wall of the elongate body to permit the progressive formation of a slit through the wall to allow lateral escape of the guidewire.

43. A split dilator system as in claim 34, wherein the split comprises a pre formed slit completely through the wall.

44. A split dilator system as in claim 34, wherein the distal endpoint is spaced proximally apart within the range of from about 5 cm to about 40 cm from the distal end of the catheter.

45. A split dilator system as in claim 34, wherein the grip body comprises a paddle shape with the first gripping surface on a first side and configured to be held between a thumb and forefinger such that a guidewire can be pinned between the thumb and the first gripping surface.

46. A split dilator system as in claim 45, further comprising friction enhancing surface structures on the first gripping surface.

47. A split dilator system as in claim 46, wherein the friction enhancing surface structures comprise a plurality of ridges.

* * * * *